(12) United States Patent
Cleland et al.

(10) Patent No.: US 12,121,585 B2
(45) Date of Patent: *Oct. 22, 2024

(54) DENDRIMER COMPOSITIONS AND METHODS FOR DRUG DELIVERY TO THE EYE

(71) Applicant: Ashvattha Therapeutics, Inc., Redwood City, CA (US)

(72) Inventors: Jeffrey L. Cleland, Redwood City, CA (US); Rishi Sharma, Redwood City, CA (US); Santiago Appiani, Redwood City, CA (US)

(73) Assignee: Ashvattha Therapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,636

(22) Filed: Jan. 26, 2023

(65) Prior Publication Data

US 2024/0058459 A1 Feb. 22, 2024

Related U.S. Application Data

(63) Continuation of application No. 17/112,255, filed on Dec. 4, 2020, now Pat. No. 11,612,660.

(60) Provisional application No. 63/108,234, filed on Oct. 30, 2020, provisional application No. 63/021,023, filed on May 6, 2020, provisional application No. 62/943,724, filed on Dec. 4, 2019.

(51) Int. Cl.
| | |
|---|---|
| *A61K 47/59* | (2017.01) |
| *A61K 31/404* | (2006.01) |
| *A61K 49/00* | (2006.01) |
| *A61P 27/02* | (2006.01) |
| *C08G 73/02* | (2006.01) |

(52) U.S. Cl.
CPC .......... *A61K 47/595* (2017.08); *A61K 31/404* (2013.01); *A61K 49/0034* (2013.01); *A61K 49/0054* (2013.01); *A61P 27/02* (2018.01); *C08G 73/028* (2013.01)

(58) Field of Classification Search
CPC ..... A61K 47/56; A61K 27/02; A61K 49/0054
See application file for complete search history.

(56) References Cited

U.S. PATENT DOCUMENTS

| | | | |
|---|---|---|---|
| 4,507,466 | A | 3/1985 | Tomalia et al. |
| 4,558,120 | A | 12/1985 | Tomalia et al. |
| 4,568,737 | A | 2/1986 | Tomalia et al. |
| 4,587,329 | A | 5/1986 | Tomalia et al. |
| 5,714,166 | A | 2/1998 | Tomalia et al. |
| 5,968,979 | A | 10/1999 | Brusilow |
| 6,624,245 | B2 | 9/2003 | Wallace et al. |
| 7,674,781 | B2 | 3/2010 | Sheardown et al. |
| 8,148,356 | B2 | 4/2012 | Pavliv |
| 8,399,445 | B2 | 3/2013 | Pavliv |
| 8,404,215 | B1 | 3/2013 | Scharschmidt et al. |
| 8,427,225 | B2 | 4/2013 | Nakatake et al. |
| 8,642,012 | B2 | 2/2014 | Scharschmidt |
| 8,653,061 | B2 | 2/2014 | Pavliv |
| 8,722,738 | B2 | 5/2014 | Pavliv et al. |
| 8,889,101 | B2 | 11/2014 | Kannan et al. |
| 9,095,559 | B2 | 8/2015 | Scharschmidt et al. |
| 9,526,794 | B2 | 12/2016 | Rangaramanujam et al. |
| 10,369,124 | B2 | 8/2019 | Rangaramanujam et al. |
| 10,561,673 | B2 | 2/2020 | Rangaramanujam et al. |
| 11,160,881 | B2 | 11/2021 | Rangaramanujam et al. |
| 11,446,238 | B2 | 9/2022 | Rangaramanujam et al. |
| 11,612,660 | B2 | 3/2023 | Cleland et al. |
| 2002/0068795 | A1 | 6/2002 | Won et al. |
| 2002/0192843 | A1 | 12/2002 | Kaganove et al. |
| 2003/0180250 | A1 | 9/2003 | Chauhan et al. |
| 2004/0151754 | A1 | 8/2004 | Ashton |
| 2006/0041058 | A1 | 2/2006 | Yin et al. |
| 2006/0204443 | A1 | 9/2006 | Kobayashi et al. |
| 2006/0240110 | A1 | 10/2006 | Kiick et al. |
| 2007/0088014 | A1 | 4/2007 | Edelman et al. |
| 2007/0128681 | A1 | 6/2007 | Barman et al. |

(Continued)

FOREIGN PATENT DOCUMENTS

| | | |
|---|---|---|
| CA | 2777682 A1 | 5/2011 |
| EP | 1639029 B1 | 7/2007 |

(Continued)

OTHER PUBLICATIONS

International Search Report and Written Opinion for Application No. PCT/US2015/028386 mailed Apr. 30, 2015.
International Preliminary Report on Patentability for Application No. PCT/US2015/028386 mailed Nov. 10, 2016.
International Search Report and Written Opinion for Application No. PCT/US2020/063347 mailed Jul. 16, 2021.
International Preliminary Report on Patentability for Application No. PCT/US2020/063347 mailed Jun. 16, 2022.
[No Author Listed], Ciba® IRGACURE® 2959 Photoinitiator product information. Ciba Specialty Chemicals Inc. Published Jun. 29, 2011. Accessed Apr. 29, 2022. 3 pages.

(Continued)

*Primary Examiner* — James W Rogers
(74) *Attorney, Agent, or Firm* — Wolf, Greenfield & Sacks, P.C.

(57) ABSTRACT

Dendrimer compositions and methods for the treatment of one or more inflammatory and/or angiogenic diseases and/or disorders of the eye include hydroxyl-terminated dendrimers complexed or conjugated with one or more active agents for the treatment or alleviation of one or more symptoms of the diseases of the eye, and/or for diagnosing the diseases and/or disorders of the eye. The dendrimers may include one or more ethylene diamine-core poly(amidoamine) (PAMAM) hydroxyl-terminated generation-4, 5, 6, 7, 8, 9, or 10 dendrimers. The active agents may be VEGFR tyrosine kinase inhibitors including sunitinib or analogues thereof. Preferably, the compositions are suitable for administration via a systemic route to target activated microglia/macrophages in retina/choroid.

20 Claims, 13 Drawing Sheets

(56) References Cited

U.S. PATENT DOCUMENTS

| | | |
|---|---|---|
| 2007/0298006 A1 | 12/2007 | Tomalia et al. |
| 2008/0031848 A1 | 2/2008 | Konradi et al. |
| 2009/0104123 A1 | 4/2009 | Yang et al. |
| 2010/0015231 A1 | 1/2010 | Lu |
| 2010/0160299 A1 | 6/2010 | Baker, Jr. et al. |
| 2011/0034422 A1 | 2/2011 | Kannan et al. |
| 2011/0189291 A1 | 8/2011 | Yang et al. |
| 2011/0189299 A1 | 8/2011 | Okubo et al. |
| 2012/0003155 A1 | 1/2012 | Kannan et al. |
| 2012/0177593 A1 | 7/2012 | Baker, Jr. et al. |
| 2012/0197060 A1 | 8/2012 | Ray et al. |
| 2012/0263672 A1 | 10/2012 | Artzi et al. |
| 2013/0123330 A1 | 5/2013 | Lu et al. |
| 2013/0136697 A1 | 5/2013 | Kannan et al. |
| 2013/0165771 A1 | 6/2013 | Ni et al. |
| 2015/0352230 A1 | 12/2015 | Mullen et al. |
| 2016/0279054 A1 | 9/2016 | Rangaramanujam et al. |
| 2017/0028075 A1 | 2/2017 | Rangaramanujam et al. |
| 2017/0119899 A1 | 5/2017 | Kannan et al. |
| 2017/0216200 A1 | 8/2017 | Rangaramanujam et al. |
| 2018/0256480 A1 | 9/2018 | Deng et al. |
| 2020/0022938 A1 | 1/2020 | Rangaramanujam et al. |
| 2021/0170040 A1 | 6/2021 | Cleland et al. |
| 2021/0252153 A1 | 8/2021 | Mangraviti et al. |

FOREIGN PATENT DOCUMENTS

| | | |
|---|---|---|
| WO | WO 00/18394 A1 | 4/2000 |
| WO | WO 2003/080121 A1 | 10/2003 |
| WO | WO 2004/041310 A1 | 5/2004 |
| WO | WO 2004/058272 A1 | 7/2004 |
| WO | WO 2004/106411 A2 | 12/2004 |
| WO | WO 2005/055926 A2 | 6/2005 |
| WO | WO 2006/033766 A2 | 3/2006 |
| WO | WO 2006/115547 A2 | 11/2006 |
| WO | WO 2007/089607 A2 | 8/2007 |
| WO | WO 2008/068531 A2 | 6/2008 |
| WO | WO 2009/046446 A2 | 4/2009 |
| WO | WO 2009/142754 A1 | 11/2009 |
| WO | WO 2010/147831 A1 | 12/2010 |
| WO | WO 2011/011384 A2 | 1/2011 |
| WO | WO 2011/123591 A1 | 10/2011 |
| WO | WO 2012/037457 A1 | 3/2012 |
| WO | WO 2012/142470 A1 | 10/2012 |
| WO | WO 2014/026283 A1 | 2/2014 |
| WO | WO 2014/109927 A1 | 7/2014 |
| WO | WO 2014/178892 A1 | 11/2014 |
| WO | WO 2014/197909 A1 | 12/2014 |
| WO | WO 2015/027068 A1 | 2/2015 |
| WO | WO 2015/038493 A1 | 3/2015 |
| WO | WO 2015/168347 A1 | 11/2015 |
| WO | WO 2016/025741 A1 | 2/2016 |
| WO | WO 2016/025745 A1 | 2/2016 |
| WO | WO 2017/074993 A1 | 5/2017 |
| WO | WO 2017/139341 A1 | 8/2017 |
| WO | WO 2019/094952 A1 | 5/2019 |

OTHER PUBLICATIONS

[No Author Listed], Contraceptive, cholesterol-lowering drugs used to treat cancer. University of Birmingham. ScienceDaily, https://www.sciencedaily.com/releases/2015/05/150514102813.htm, [last accessed May 2015].

Alizadeh, et al., "Tumor-associated macrophages are predominant carriers of cyclodextrin-based nanoparticles into gliomas", Nanomedicine, 6:382-90 (2010). Author Manuscript.

Almutairi, et al., "Biodegradable dendritic position emitting nanoprobes for the noninvasive Imaging of angiogenesis", PNAS, 106(3):685-90 (2009).

Almutairi, et al., "Monitoring the biodegradation of dendritic near-infrared nanoprobes by in vivo fluorescence imaging", Mol Pharm., 5(6):1103-10 (2008). Author Manuscript.

Alving, et al., "Therapy of leishmaniasis: Superior efficacies of liposome-encapsulated drugs", PNAS, 75(6):2959-63 (1978).

Ambati et al., Age-related macular degeneration: etiology, pathogenesis, and therapeutic strategies. Surv Ophthalmol. May-Jun. 2003;48(3):257-93. doi: 10.1016/s0039-6257(03)00030-4.

Aslam, et al., "Antibacterial and antifungal activity of cicerfuran and related 2-arylbenzofurans and stilbenes", Microbial Res., 164:191-5 (2009).

Augustin, et al., "Effects Of Allopurinol And Steroids On Inflammation And Oxidative Tissue Damage In Experimental Lens Induced Uveitis: A Biochemical And Morphological Study," Br. J. Ophthalmol. 80(5):451-7 (1996).

Bagul, et al., "Heterolayered hybrid dendrimers with optimized sugar head groups for enhancing carbohydrate-protein interactions", Polymer Chemistry, 8(35):5354-5366 (2017).

Balakrishnan, et al., "Nanomedicine in cerebral palsy", Intl J Nanomedicine, 8:4183-95 (2013).

Ballatori, "N-Acetyl cysteine as an antidote in methyl mercury poisoning", EnViron. Health Perspect., 106 (5):267-71 (1998).

Barrett, et al., "Dendrimers in medical nanotechnology", Eng Med Biol Mag., 28(1):12-22 (2009).

Bhutto et al., Transport and microglia uptake of dendrimers in normal and ischemia/reperfusion injury retina. Investigative Ophthalmology & Visual Science. Apr. 2014;55:1448. Abstract. 2 pages.

Bosnjkovic, "A dendrimer-based immunosensor for improved capture and detection of tumor necrosis factor-alpha cytokine", Analytical Achiica Acta, 720: 118-25 (2012). Author Manuscript.

Bourges, et al., "Ocular Drug Delivery Targeting The Retina And Retinal Pigment Epithelium Using Polylactide Nanoparticles," Invest. Opthalmol. & Vis. Sci., 44:3562-9 (2003).

Bracci, et al., "Synthetic peptides in the form of dendrimers become resistant to protease activity", J Biol Chem.,278:46590-5 (2003).

Bravo-Osuna, et al., "Interfacial Interaction between Transmembrane Ocular Mucins and Adhesive Polymers and Dendrimers Analyzed by surface Plasmon Resonance", Pharmaceutical Research, 29(8):2329-2340 (2012). Author Manuscript.

Calabretta, et al., "Antibacterial activities of poly(amidoamine) dendrimers terminated with amino and poly(ethylene glycol) groups", Biomacromolecules, 8:1807-11 (2007). Author Manuscript.

Caminade et al., Dendrimers for drug delivery. J Mater Chem B. Jul. 14, 2014;2(26):4055-4066. doi: 10.1039-c4tb00171k. Epub Jun. 2, 2014.

Carbonell, et al., "Migration of perilesional microglia after focal brain injury and modulation by CC chemokine receptor 5: an in situ time-lapse confocal imaging study", J Neurosci., 27:30):7040-7 (2005).

Chauhan, et al., "Strategies for advancing cancer nanomedicine", Nature Materials, 12:958-62 (2013). Author Manuscript.

Chertok, et al., "Glioma Selectivity of Magnetically Targeted Nanoparticles: A Role of Abnormal Tumor Hydrodynamics", J Controlled Release, 122(3):315-23 (2007). Author Manuscript.

Chertok, et al., "Substantiating in vivo magnetic brain tumor targeting of cationic iron oxide nanocarriers via adsorptive surface masking", Biomaterials, 30:6780-7 (2009). Author Manuscript.

Choi, et al., "Dynamic fluorescence imaging for multiparametric measurement of tumor vasculature", J Biomedical Optics, 16(4):046008 (2011).

Choi, et al., "Renal clearance of quantum dots", Nature Biotechnology, 25(10):1165-70 (2007). Author Manuscript.

Chouinard-Pelletier, et al., "Use of inert gas jets to measure the forces required for mechanical gene transfection", BioMedical Eng Online, 11 (67):1-12 (2012).

Cleland et al., Suppression of Murine Choroidal Neovascularization After Systemic Administration of a Targeted Anti-VEGF Therapy. Invest. Ophthalmol. Vis. Sci. 2020;61(7):3974.

Curthoys, et al., "Proximal Tubule Function and Response to Acidosis", Clin J Am Soc Nephrol, 9: 1627-38 (2014 ).

Da Fonseca, et al., "Microglia and Macrophages in Malignant Gliomas: Recent Discoveries and Implications for Promising Therapies", Clin Dev Immunol., Article ID 264124: 1-5 (2013).

Dai, et al., "Intrinsic targeting of inflammatory cells in the brain by polyamidoamine dendrimers upon subarachnoid administration", Nanomedicine 5(9): 1317-29 (2010). Author Manuscript.

(56) References Cited

OTHER PUBLICATIONS

Dekhuijzen, "Antioxidant properties of N-acetyl cysteine. their relevance in relation to chronic obstructive pulmonary disease", Eur Respir J., 23:629-36 (2004).
Desai, et al., "Synthesis and characterization of photocurable polyamidoamine dendrimer hydrogels as a versatile platform for tissue engineering and drug delivery", Biomacromolecules, 11 (3):666-73 (2010). Author Manuscript.
Dinkel et al., "Novel Glucocorticoid Effects On Acute Inflammation In The CNS," J.Neurochem. 84(4):705-16 (2003).
Dolman et al., Dendrimer-based macromolecular conjugate for the kidney-directed delivery of a multitargeted sunitinib analogue. Macromol Biosci. Jan. 2012;12(1):93-103. doi: 10.1002-mabi.201100277. Epub Oct. 13, 2011.
Downs, et al., "Long-Term Safety of Repeated Blood-Brain Barrier Opening via Focused Ultrasound with Microbubbles in Non-Human Primates Performing a Cognitive Task", Plos One, 10(5):e0125911 (2015).
Dumont, et al., "Bezafibrate administration improves behavioral deficits and tau pathology in P301S mice", Hum Mal Genet., 21(23):5091-5105 (2012).
Dunlap, et al., "Nanoscopic structure of DNA condensed for gene delivery", Nucleic Acids Res,. 25(15):3095-101 (1997).
Ellison, et al., "Damage of the outer membrane of enteric gram-negative bacteria by lactoferrin and transferrin", Infect Immun., 56:2774-81 (1988).
Esfand et al., Poly(amidoamine) (PAMAM) dendrimers: from biomimicry to drug delivery and biomedical applications. Drug Discov Today. Apr. 1, 2001;6(8):427-436. doi: 10.1016-s1359-6446(01)01757-3.
Ferrari, et al., "N-acetylcysteine (D- and L-stereoisomers) prevents apoptotic death of neuronal cells", J Neurosci., 15:2857-66 (1995).
Filipovska, et al., "Delivery of antisense peptide nucleic acids (PNAs) to the cytosol by disulphide conjugation to a lipophilic cation", FEBS Lett., 556:180-6 (2004).
Fujiki, et al., "Peroxisome biogenesis in mammalian cells", Front Physiol., 5:307 (2014).
Gabrusiewicz, et al., "Characteristics of the Alternative Phenotype of Microglia-Macrophages and its Modulation in Experimental Gliomas", PLoS One, 6(8): e23902 1-12 pages (2011).
Gondcaille et al., "Phenylbutyrate up-regulates the adrenoleukodystrophy-related gene as a nonclassical peroxisome proliferator", J Cell Biol., 169(1):93-104 (2005).
Gonzalez et al., "Glucocorticoids Antagonize AP-1 By Inhibiting The Activation-Phosphorylation Of JNK Without Affecting Its Subcellular Distribution," J.Cell Biol. 150(5):1199-208 (2000).
Grinstaff, "Designing hydrogel adhesives for corneal wound repair", Biomaterials, 28(35):5205-14 (2007). Author Manuscript, 18 pages.
Haga, et al., "Involvement of the Multidrug Resistance Protein 3 in Drug Sensitivity and Its Expression in Human Glioma", Jp J Cancer Res., 92:211-19 (2001).
Han, et al., "Multifunctional Dendrimer-Templated Antibody Presentation on Biosensor Surfaces for Improved Biomarker Detection", Adv. Funct. Mater., 20:409-21 (2010). Author Manuscript, 29 pages.
Hashemian et al., Comparison of different doses of subconjunctival sunitinib with bevacizumab in the treatment of corneal neovascularization in experimental rats. J Res Med Sci. Feb. 16, 2017;22:16. doi: 10.4103-1735-1995.200266.
Heath, et al., "Nanotechnology and Cancer", Ann Rev Med., 59:251-65 (2008). Author Manuscript, 16 pages.
Heier, et al., "VBP15, a novel anti-inflammatory and membrane-stabilizer, improves muscular dystrophy without side effects", EMBO Mol Med., 5(10): 1569-85 (2013).
Helander, et al., "Fluorometric assessment of gram-negative bacterial permeabilization", J Appl Microbiol, 88:213-9 (2000).
Hobbs, et al., "Regulation of transport pathways in tumor vessels: Role of tumor type and microenvironment", PNAS, 95:4607-12 (1998).

Huang, et al., "Efficient gene delivery targeted to the brain using a transferrin-conjugated polyethyleneglycol-modified polyamidoamine dendrimer", FASEB, 21(4):1117-25 (2007).
Huang, et al., "Size-Dependent Localization and Penetration of Ultrasmall Gold Nanoparticles in Cancer Cells, Multicellular Spheroids, and Tumors in Vivo", ACS Nano, 6(5):4483-93 (2012). Author Manuscript, 17 pages.
Hussain, et al., "The role of human glioma-infiltrating microglia-macrophages in mediating antitumor immune responses", Neuro-Oncology, 8:261-79 (2006).
Iacobazzi et al., Targeting human liver cancer cells with lactobionic acid-G(4)-PAMAM-FITC sorafenib loaded dendrimers. Int J Pharm. Aug. 7, 2017;528(1-2):485-497. doi: 10.1016-j.ijpharm.2017.06.049. Epub Jun. 15, 2017.
Iezzi, et al., "Dendrimer-based targeted intravitreal therapy for sustained attenuation of neuroinflammation in retinal degeneration", Biomaterials, 33(3):979-988 (2012).
Jaffe, et al., "Safety and Pharmacokinetics of an Intraocular Fluocinolone Acetonide Sustained Delivery Device," Invest. Ophthalmol. & Vis. Sci. 41:3569-75 (2000).
Jain, et al. "Delivering nanomedicine to solid tumors", Ntl Rev Clinical Oncology, 7(11):653-64 (2010). Author Manuscript, 24 pages.
Jiang, et at., "Tumor Imaging by Means of Proteolytic Activation of Cell-Penetrating Peptides", PNAS, vol. 101(51):17867-72 (2004).
Jonas, et al., "Intravitreal triamcinolone acetonide for exudative age related macular degeneration", Br J Ophthalmol., 87(4):462-8 (2003).
Jones, et al., "Cationic PAMAM dendrimers aggressively initiate blood clot formation", ACS Nano, 6:9900-10 (2012). Author Manuscript, 20 pages.
Jones, et al., "Cationic PAMAM dendrimers disrupt key platelet functions", Mol Pharma., 9:1599-611 (2012b). Author Manuscript, 23 pages.
Jou, et al., "Gangliosides Trigger Inflammatory Responses Via TLR4 In Brain Glia," Am. J. Pathol., 168:1619-30 (2006).
Kambhampati, et al., "Intracellular delivery of dendrimer triamcinolone acetonide conjugates into microglial and human retinal pigment epithelial cells", Eur. J. Pharm. Biopharm., 95(Pt B):239-49 (2015).
Kambhampati, et al., "Systemic and Intravitreal Delivery of Dendrimers to Activated Microglia/Macrophage in Ischemia/Reperfusion Mouse Retina", Retinal Cell Biology, 56(8):4413-24 (2015).
Kannan et al., Emerging concepts in dendrimer-based nanomedicine: from design principles to clinical applications. J Intern Med. Dec. 2014;276(6):579-617. doi: 10.1111-joim.12280. Epub Jul. 31, 2014.
Kannan, et al., "Dendrimer-based postnatal therapy for neuroinflammation and cerebral palsy in a rabbit model", Sci Trans Med., 4(130) (2012). Author Manuscript, 21 pages.
Kannan, et al., "Magnitude of [(11)C] PK11195 binding is related to severity of motor deficits in a rabbit model of cerebral palsy induced by intrauterine endotoxin exposure", Dev Neurosci., 33:231-40 (2011).
Kannan, et al., "Microglial activation in perinatal rabbit brain induced by intrauterine inflammation detection with 11C-(R)-PK11195 an6 small-animal PE1", J. Nucl Med., 48(6):946-54 (2007).
Kapadia, et al., "Mechanisms of anti-inflammatory and neuroprotective actions of PPAR-gamma agonists", Front Biosci., 13:1813-26 (2009). Author Manuscript, 22 Pages.
Katai, et al., "Caspase-like Proteases Activated In Apoptotic Photoreceptors Of Royal College Of Surgeons Rats," Invest. Ophthalmol. Vis. Sci., 40:1802-7 (1999).
Kenny, et al., "Multifunctional receptor-targeted nanocomplexes for the delivery of therapeutic nucleic acids to the brain", Biomaterials, 34(36):9190-200 (2013).
Khan, et al., "In vivo biodistribution of dendrimers and dendrimer nanocomposites implications for cancer imaging and therapy", Tech Cancer Res Treat., 4(6):603-13 (2005).
Khan, et al., "Very long-chain fatty acid accumulation causes lipotoxic response via 5-lipoxygenase in cerebral adrenoleukodystrophy", J Lipid Res., 51(7):1685-95 (2010).
Khandare et al., Synthesis, cellular transport, and activity of polyamidoamine dendrimer-methylprednisolone conjugates. Bioconjug

(56) References Cited

OTHER PUBLICATIONS

Chem. Mar.-Apr. 2005;16(2):330-7. doi: 10.1021/bc0498018. Erratum in: Bioconjug Chem. Jul.-Aug. 2005;16(4):1049.

Kim, et al., "Systematic investigation of polyamidoamine dendrimers surface-modified with poly(ethylene glycol) for drug delivery applications: synthesis, characterization, and evaluation of cytotoxicity", Bioconjug Chem., 19:1660-72 (2008). Author Manuscript, 28 pages.

Kim, et al., "Use of single-site-functionalized PEG dendrons to prepare gene vectors that penetrate human mucus barriers", Angew Chem Int Ed Engl., 52(14):3985-8 (2013). Author Manuscript, 11 pages.

Kirpotin, et al., "Antibody targeting of long-circulating lipidic nanoparticles does not increase tumor localization but does increase internalization in animal models", Cancer Res., 66:6732-40 (2006).

Kobayashi, et al., "Multimodal nanoprobes for radionuclide and five color near infrared optical lymphatic imaging", ACS Nano, 1(4):258-64 (2007). Author Manuscript, 13 pages.

Kobayashi, et al., "Renal tubular damage detected by dynamic micro-MRI with a dendrimer-based magnetic resonance contrast agent", Kidney Int.,61(6):1980-5 (2002).

Kobayashi, et al., "3D-Micro-MR Angiography of Mice Using Macromolecular MR Contrast Agents With Polyamidoamine Dendrimer Core With Reference to Their Pharmacokinetic Properties", Magnetic Resonance in Medicine, 45:454-60 (2001b).

Kolhe, et al., "Drug complexation, in vitro release and cellular entry of dendrimers and hyperbranched polymers", Int. J. Pharmaceutics, 259:143-60 (2003).

Kostarelos, et al., "Binding and Interstitial Penetration of Liposomes within Avascular Tumor Spheroids", Intl J Cancer, 112:713-21 (2004).

Kukowska-Latallo, et al., "Intravascular and endobronchial DNA delivery to murine lung tissue using a novel, nonviral vector", Hum Gene Ther, 11(10):1385-95 (2000).

Kukowska-Latallo, et al., "Nanoparticle targeting of anticancer drug improves therapeutic response in animal model of human epithelial cancer", Cancer Res., 65:5317-24 (2005).

Kukowska-Latallo, et al., "Efficient transfer of genetic material into mammalian cells using starburst polyamidoamine dendrimers", PNAS, 93:4897-902 (1996).

Kurtoglu et al., Drug release characteristics of PAMAM dendrimer-drug conjugates with different linkers. Int J Pharm. Jan. 15, 2010;384(1-2):189-94. doi: 10.1016-j.ijpharm.2009.10.017. Epub Oct. 13, 2009.

Kurtoglu, et al., "Poly(amidoamine) dendrimer-drug conjugates with disulfide linkages for intracellular drug delivery", Biomaterials, 30, 2112-21 (2009) Author Manuscript, 26 pages.

Landers, et al., Prevention of Influenza Pneumonitis by Sialic Acid-conjugated Dendritic Polymers, J. of Infectious Diseases, 186:1222-30 (2002).

Lee, et al., "A single dose of doxorubicin functionalized bow-tie dendrimer cures mice bearing C-26 colon carcinomas'", PNAS, 103:16649-56 (2006).

Lee, et al., "Blood Volume in the Rat", J Nuclear Med., 25:72-6 (1985).

Lentz, et al., "Viral vectors for gene delivery to the central nervous system", Neurobiol Dis, 48(2):179-188 (2012). Author Manuscript, 22 pages.

Lesniak et al., Biodistribution of fluorescently labeled PAMAM dendrimers in neonatal rabbits: effect of neuroinflammation. Mol Pharm. Dec. 2, 2013;10(12):4560-71. doi: 10.1021-mp400371r. Epub Oct. 30, 2013. Author Manuscript, 25 pages.

Lesniak, et al., "Synthesis and characterization of PAMAM dendrimer based multifunctional nanodevices for targeting alphavbeta3 integrins", Bioconjug Chem., 18(4):1148-54 (2007). Author Manuscript, 21 pages.

Lessio, et al., "Cyclosporine A and NAC on the inducible nitric oxide synthase expression and nitric oxide synthesis in rat renal artery cultured cells", Kidney Int., 68:2508-16 (2005).

Li, et al., "Peroxynitrite generated by inducible nitric oxide synthase and NADPH oxidase mediates microglial toxicity to oligodendrocytes", PNAS, 102:9936-41 (2005).

Li, et al., "The molecular profile of microglia under the influence of glioma", Neuro-Oncology, 14(8):958-78 (2012).

Liang, et al., "Long-Term Protection Of Retinal Structure But Not Function Using RAAV.CNTF In Animal Models Of Retinitis Pigmentosa," Mol. Ther. 4(5):461-72 (2001).

Liang, et al., "PAMAM Dendrimers and Branched Polyethyleneglycol (nanoparticles) Prodrugs of (-)-[beta]-D-(2R, 4R)-Dioxolane-Thymine (DOT) and Their Anti-HIV Activity", Antiviral Chemistry and Chemotherapy, 17(6) 321-9 (2006).

Liebner, et al., "Claudin-1 and claudin-5 expression and tight junction morphology are altered in blood vessels of human glioblastoma multiforme", Acta Neuropathol., 100:323-31 (2000).

Ling, Fluorescent probe for detection of intracellular hydrogen peroxide. Scientific and Technological Innovation. 2007;9. English language summary. 2 pages.

Liu et al., Loading IR820 Using Multifunctional Dendrimers with Enhanced Stability and Specificity. Pharmaceutics. 2018;10(77):12 pages.

Locke, et al., "PET imaging of tumor associated macrophages using mannose coated 64Cu liposomes", Biomaterials, 33:7785-93 (2012).

Loes, et al., "Adrenoleukodystrophy: a scoring method for brain MR observations", AJNR Am J Neuroradiol, 15:1761-6 (1994).

Lopez-Erauskin, et al., "Antioxidants halt axonal degeneration in a mouse model of X-adrenoleukodystrophy", Annals of neurology, 70(1):84-92 (2011).

Lu, et al., "YC-1 attenuates LPS-induced proinflammatory responses and activation of nuclear factor-kB in microglia", Br J Pharmacol. ,151:396-405 (2007).

Madaan, et al., "Dendrimers in drug delivery and targeting: Drug-dendrimer interactions and toxicity issues", Journal of pharmacy & bioallied sciences, 6.3: 139 (2014).

Makki, et al., "Intrauterine administration of endotoxin leads to motor deceits in a rabbit model: a link between prenatal infection and cerebral palsy", Am. J. Obstet. Gynecol. , 199: 651-1651 (2008).

Mallard, et al., "Astrocytes and microglia in acute cerebral injury underlying cerebral palsy associated with preterm birth", Pediatr Res., 75:234-40 (2014).

Marano, et al., "Dendrimer Delivery Of An Anti-VEGF Oligonucleotide Into The Eye: A Long-Term Study Into Inhibition Of Laser-Induced CNV, Distribution, Uptake And Toxicity," Nature Gene Therapy 12:1544-50 (2005).

Marchetti, et al., "Mitochondrial Permeability Transition Is A Central Coordinating Event Of Apoptosis," J. Exp. Med., 184(3):1155-60 (1996).

Markovic, et al., "Minocycline reduces glioma expansion and invasion by attenuating microglial MT1-MMP expression", Brain, Behavior, Immunity, 25:624-8 (2011).

Marneros, Increased VEGF-A promotes multiple distinct aging diseases of the eye through shared pathomechanisms. EMBO Mol Med. Mar. 1, 2016;8(3):208-31. doi: 10.15252-emmm.201505613.

Marquet, et al., "Noninvasive, transient and selective blood-brain barrier opening in non-human primates in vivo", Plos One, 6(7): ):e22598. doi: 10.1371 (2011).

Mayhan and Heistad, "Permeability of blood-brain barrier to various sized molecules", Am J Physiol., 248:H712-8 (1985).

Menjoge et al., "Dendrimer-based drug and imaging conjugates design considerationsfor nanomedical applications", Drug Deliv Today, 15(5-6):171-85 (2010).

Menjoge, et al., "Transfer of PAMAM dendrimers across human placenta: Prospects of its use as drug carrier during pregnancy", J Controlled Release, 150(3):326-38 (2011).

Menjoge, et al., "Transport and bio distribution of dendrimers across human fetal membranes Implications for intravaginal administration of dendrimer-drug conjugates", Biomaterials, 31(18):50107-21 (2010b).

Meyer-Luehmann, et al., "Rapid appearance and local toxicity of amyloid-beta plaques in a mouse model of Alzheimer's disease", Nature; 451:720-4 (2008).

(56) References Cited

OTHER PUBLICATIONS

Meyers, et al., "Nanoparticles for imaging and treating brain cancer", Nanomedicine (Lond), 8(1):123-43 (2013).
Mignani, et al., "Expand classical drug administration ways by emerging routes using dendrimer drug delivery systems: A concise overview", Adv Drug Delivery Rev., 65(10):1316-30 (2013).
Mishra, et al., "Dendrimer brain uptake and targeted therapy for brain injury in a largeanimal model of hypothermic circulatory arrest", ACS Nano, 8:2134-47 (2014).
Morato, et al., "Activation of sirtuin 1 as therapy for the peroxisomal disease adrenoleukodystrophy", Cell Death Differ., 22:1742-53 (2015).
Morato, et al., "Pioglitazone halts axonal degeneration in a mouse model of X-linked adrenoleukodystrophy", Brain, 136(Pt 8):2432-43 (2013).
Mumper, et al., "Formulating a sulfonated antiviral dendrimer in a vaginal microbicidal gel having dual mechanisms of action", Drug Dev Ind Pharma., 35:515-24 (2009).
Myers, "The Effect of Hydroxyl Ion Concentration on the Thermal Death Rate of Bacterium Coli", J Bacteria, 15:341-56 (1928).
Mythri, et al., "Novel mucoadhesive polymers—A Review", J App Pharma Sci., 1(8):37-42 (2011).
Nance et al., Nanoscale effects in dendrimer-mediated targeting of neuroinflammation. Biomaterials. Sep. 2016;101:96-107. doi: 10.1016-j.biomaterials.2016.05.044. Epub May 26, 2016. Author Manuscript.
Nance, et al., "A dense poly(ethylene glycol) coating improves penetration of large polymeric nanoparticles within brain tissue", Sci Transl Med,, 4:149ra119 (2012).
Nance, et al., "Brain-penetrating nanoparticles improve paclitaxel efficacy in malignant glioma following local administration", ACS Nano., 8(10):10655-64 (2014).
Nance, et al., "Systemic dendrimer-drug treatment of ischemia-induced neonatal white matter injury", Journal of Controlled Release, 214:112-120 (2015).
Navath, et al., "Amino acid-functionalized dendrimers with heterobifunctional chemoselective peripheral groups for drug delivery applications", Biomacromolecules, 11(6):1544-63 (201Gb).
Navath, et al., "Dendrimer-drug conjugates for tailored intracellular drug release based on glutathione levels", Bioconjugate Chem., 19(12):2446-53 (2008).
Navath, et al., "Injectable PAMAM dendrimer-PEG hydrogels for the treatment of genital infections: formation and in vitro and in vivo evaluation", Molecular Pharma, 8(4):1209-23 (2011).
Navath, et al., "Stimuli-responsive star polyethylene glycol) drug conjugates for improved intracellular delivery of the drug in neuroinflammation", J Controlled Release, 142(3):447-56 (2010).
Neal, et al., "Discovery and validation of a new class of small molecule toll-like receptor 4 (TLR4) inhibitors", Plos One, 8(6):e65779 (2013).
Neeves, et al., "Dilation and degradation of the brain extracellular matrix enhances penetration of infused polymer nanoparticles", Brain Res., 11BO:121-32 (2007).
Nigavekar, et al., "3H dendrimer nanoparticle organ-tumor distribution", Pharm Res., 21(3):476-83 (2004).
Noell, et al., "Selective enrichment of hypericin in malignant glioma: Pioneering in vivo results", Intl J Oncology, 38: 1343-8 (2011 ).
Oh, et al., "Synthesis, Characterization, and Surface Immobilization of Metal Nanoparticles Encapsulated within Bifunctionalized Dendrimers", Langmuir,19(24):10420-5 (2003).
Okada, et al., Tumor-associated macrophage-microglia infiltration in human gliomas is correlated with MCP-3, but not MCP-1, Intl J Oncology, 34:1621-7 (2009).
Olivas, "ReveraGen BioPharma Announces Start of Phase 1 Clinical Trial of VBP15 Dissociative Steroid Drug," http:--www.prnewswire.com-news-releases-reveragen- biopharma-announces-start-of-phase-1-clinical-trial-of-vbp15-dissociative-steroid- drug-300037964.html,media release, (Feb. 18, 2015).
Orr, et al., "Adenosine A2A receptor mediates microglial process retraction", Nat Neurosci., 12(7):872-8 (2009).
Oupicky, et al., "Laterally stabilized complexes of DNA with linear reducible polycations: strategy for triggered intracellular activation of DNA delivery vectors", J.Am Chem. Soc., 124:, 8-9 (2002).
Palmer, et al., "S-Nitrosothiols signal hypoxia-mimetic vascular pathology", J ClinInvest., 117:2592-601 (2007).
Pardridge, "Drug transport across the blood-brain barrier", J Cereb Blood Flow Metab, 32:1959-72 (2012).
Park et al., Effect of sorafenib on experimental choroidal neovascularization in the rat. Clin Exp Ophthalmol. Oct. 2010;38(7):718-26. doi: 10.1111-j.1442-9071.2010.02328.x. Epub Jul. 9, 2010.
Parney, et al., "Flow cytometry and in vitro analysis of human glioma-associated macrophages", J Neurosurg., 110(3):572-82 (2009).
Patel et al., "Polymeric nanoparticles for drug delivery to the central nervous system", Adv Drug Delivery Rev, 64(7):701-5 (2012).
Patil, et al., "Internally cationic polyamidoamine PAMAM-OH dendrimers for siRNA delivery: effect of the degree of quaternization and cancer targeting", Biomacromolecules, 10:258-66 (2009).
Perez-Martinez, et al., "The use of nanoparticles for gene therapy in the nervous system", J Alzheimers Dis, 31(4):697-710 (2012).
Perez-Santonja et al., Inhibition of corneal neovascularization by topical bevacizumab (Anti-VEGF) and Sunitinib (Anti-VEGF and Anti-PDGF) in an animal model. Am J Ophthalmol. Oct. 2010; 150(4):519-528.e1. doi: 10.1016-j.ajo.2010.04.024. Epub Jun. 29, 2010.
Perumal, et al., "Effects of branching architecture and linker on the activity of hyperbranched polymer-drug conjugates", Bioconjugates Chem., 20(5):842-96 (2009).
Petrovski et al., Clearance of dying ARPE-19 cells by professional and nonprofessional phagocytes in vitro—implications for age-related macular degeneration (AMD). Acta Ophthalmol. Feb. 2011;89(1):e30-4. doi: 10.1111/j.1755-3768.2010.02047.x. Epub Nov. 23, 2010.
Pikkemaat, et al., "Dendritic PARAS EST Contrast Agents for Magnetic Resonance Imaging", Contrast Media Mol. Imaging, 2:229-39 (2007).
Polam, "Effect of Chorioamnionitis on Neurodevelopmental Outcome in Preterm Infants", Arch Pediatrics Adolesc. Med., 159(11 ): 1004-1085 (2005).
Powers, et al., "The dorsal root ganglia in adrenomyeloneuropathy: neuronal atrophyand abnormal mitochondria", J Neuropathol Exp Neural., 60(5):493-501 (2001).
Pujol, et al., "Late onset neurological phenotype of the X-ALD gene inactivation inmice: a mouse model for adrenomyeloneuropathy", Hum Mol Gene, 11(5):499-505 (2002).
Pyo, et al., "Gangliosides Activate Cultured Rat Brain Microglia," J.Biol. Chem., 274:34584-9 (1999).
Qi, et al., "PEG-conjugated PAMAM Dendrimers Mediate Efficient Intramuscular GeneExpression", Aaps J, 11(3):395-405 (2009).
Rajaguru, et al., "Development of improved retinal prosthesis, using local release polymer coatings and sustained release dendrimer-drug nanodevices", Am Inst of Chem Engineers, Annual meeting Session# 447d-(22b), Nov. 2006.
Regina, et al., "Antitumour activity of ANG1005, a conjugate between paclitaxel andthe new brain delivery vector Angiopep-2", Br. J. Pharmacol., 155(2):185-97 (2008).
Ren et al., The Effect of CM082, an Oral Tyrosine Kinase Inhibitor, on Experimental Choroidal Neovascularization in Rats. J Ophthalmol. 2017;2017:6145651. doi: 10.1155-2017-6145651. Epub Oct. 22, 2017.
Rippe, et al., "Effects of glomerular filtration rate on Ficoll sieving coefficients {theta) in rats", Kidney Intl, 69: 1326-32 (2006).
Romero, et al. "Micronutrients and intrauterine infection, preterm birth and the fetalinflammatory response syndrome", J Nutrition, 16685-16735 (2003).
Roy, et al., "Oral gene delivery with chitosan-DNA nanoparticles generates immunologicprotection in a murine model of peanut allergy", Nature Med., 5:387-91 (1999)., Free Radie Biol Med., 45:686-99 (1999).
Saad, et al., "Receptor targeted polymers, dendrimers, liposomes: which nanocarrier isthe most efficient for tumor-specific treatment and imaging", J Control Release, 130(2):107-14 (2008).

(56) References Cited

OTHER PUBLICATIONS

Saadani-Makki, et al, "Intrauterine administration of endotoxin leads to motor deficitsin a rabbit model: a link between prenatal infection and cerebral palsy", Am J Obstet Gynecol., 199(6):651-9 (2009b).

Saadani-Makki, et al., "Intrauterine endotoxin administration leads to white matterdiffusivity changes in newborn rabbits", J. Child Neural., 24:1179-89 (2009).

Sadekar, et al., "Comparative Biodistribution of Pamam Dendrimers and HPMA Copolymers in Ovarian Tumor-Bearing Mice", Biomacromolecules, 12(1):88-96 (2011).

Sadekar, et al., "Comparative pharmacokinetics of PAMAM-OH dendrimers and HPMA copolymers in ovarian tumor-bearing mice", Drug Deliv Transl Res., 3(3):260-71 (2013).

Sadekar, et al., "Transepithelial transport and toxicity of PAMAM dendrimers for oral drug delivery", Adv Drug Del Rev., 64:571-88 (2012).

Sahoo, et al., "Residual Polyvinyl Alcohol Associated With Poly (D,L-Lactide-Co-Glycolide) Nanoparticles Affects Their Physical Properties And Cellular Uptake," J. Control. Release, 82:105-14 (2002).

Sanvicens, et al., "Oxidative Stress-Induced Apoptosis In Retinal Photoreceptor Cells Is Mediated By Calpains And Caspases And Blocked By The Oxygen Radical Scavenger CR-6," J. Biol. Chem. 279(38):39268-78 (2004).

Sarin, et al., "Effective transvascular delivery of nanoparticles across the blood-braintumor barrier into malignant glioma cells", J Trans Med., 6(80):1-15 (2008).

Sarin, et al., "Physiologic upper limit of pore size in the blood-tumor barrier of malignant solid tumors", J Translational Medicine, 7(51):1-12 (2009).

Sato, et al., "Pharmacokinetics and enhancement patterns of macromolecular MR contrast agents with various sizes of polyamidoamine dendrimer cores", Magn Reson Med., 46:1169-73 (2001).

Sato, et at., "Tumor Targeting and Imaging of intraperitoneal Tumors by Use of Antisense Oligo-DNA Complexed with Dendrimers and-or Avidin in Mice1", ClinicalCancer Research, 7:3606-12 (2001b).

Schonenberger and Kovacs, "Hypoxia signaling pathways: modulators of oxygen-related organelles", Front Cell Dev Biol., 3:42-19 (2015).

Seo et al., Inhibition of corneal neovascularization in rats by systemic administration of sorafenib. Cornea. Aug. 2012;31(8):907-12. doi: 10.1097-ICO.0b013e31823f8b9c.

Shafie et al., Sorafenib-loaded PAMAM dendrimer attenuates liver fibrosis and its complications in bile-duct-ligated rats. Can J Physiol Pharmacol. Aug. 2019;97(8):691-698. doi: 10.1139-cjpp-2019-0141. Epub May 9, 2019.

Sharma et al., A fast track strategy toward highly functionalized dendrimers with different structural layers: an "onion peel approach". Polym Chem. Jan. 16, 2015;6(9):1436-44.

Sharma et al., Combined $A^3$ Coupling and Click Chemistry Approach for the Synthesis of Dendrimer-Based Biological Tools. ACS Macro Lett. Oct. 2014;3(10):1079-1083. doi.org-10.1021-mz5006298.

Sharma et al., Design and synthesis of multifunctional traceable dendrimers for visualizing drug delivery. RSC Adv. 2014; 4(37):19242-19245. doi.org-10.1039-C4RA02713B.

Shi, et al., "Dendrimer-entrapped gold nanoparticles as a platform for cancer-cell targeting and imaging", Small, 3:1245-52 (2007).

Shiao, et al., "Synthesis of Dense and Chiral Dendritic Polyols Using Glyconanosynthon Scaffolds", Molecules Online, 21 (4 ):448 (2016).

Siegal et al., Doxorubicin encapsulated in sterically stabilized liposomes for the treatment of a brain tumor model: biodistribution and therapeutic efficacy. J Neurosurg. Dec. 1995;83(6):1029-37. doi: 10.3171/jns.1995.83.6.1029.

Siegal, "Which drug or drug delivery system can change clinical practice for brain tumor therapy", Neuro-Oncology, 15(6):656-69 (2013).

Sieving, et al., "Ciliarophic factor (CNTF) for human retinal degeneration phase 1 trial of CNTF delivered by encapsulated cell intraocular implants", PNAS, 103(10):3896-901 (2006).

Soiberman et al., Subconjunctival injectable dendrimer-dexamethasone gel for the treatment of corneal inflammation. Biomaterials. May 2017;125:38-53. doi: 10.1016/j.biomaterials. 2017.02.016. Epub Feb. 16, 2017.

Southam et al., Drug Redeployment to Kill Leukemia and Lymphoma Cells by Disrupting SCD1-Mediated Synthesis of Monounsaturated Fatty Acids. Cancer Res. Jun. 15, 2015;75(12):2530-40. doi: 10.1158/0008-5472.CAN-15-0202. Epub May 5, 2015.

Steffensen and Simanek, "Synthesis and manipulation of orthogonally protecteddendrimers: building blocks for library synthesis", Angew. Chem., 116:5290-2 (2004).

Steinberg, et al., "Peroxisome biogenesis disorders", Biochim Biophys Acta., 1763(12):1733-48 (2006).

Stolp, et al., "Effects of neonatal systemic inflammation on blood-brain barrier permeability and behaviour in juvenile and adult rats", Cardiovasc Psychiatry Neural.,2011:469046 (2011).

Suzuki, et al., "Regulation of cell migration and cytokine production by HGF-like protein (HLP)-macrophage stimulating protein (MSP) in primary microglia", Biomed Res., 29(2):77-84 (2008).

Sykova, and Nicholson, "Diffusion in brain extracellular space", Physiol Rev, 88(4):1277-340 (2008).

Tang, et al., "Size-Dependent Tumor Penetration and in Vivo Efficacy of Monodisperse Drug-Silica Nanoconjugates", Mol Pharma., 10:883-92 (2013).

Tang, et al., "Synthesis and Biological Response of Size-Specific, Monodisperse Drug-Silica Nanoconjugates", ACS Nano, 6(5):3954-66 (2012).

Tanito, et al., "Cytoprotective effects of geranylgeranylacetone against retinal photooxidative damage", J Neurosci., 25(9):2396-404 (2005).

Tao, et al., "Encapsulated cell-based delivery of CNFT reduces photoreceptor degeneration in animal models of retinitis pigmentosa", Invest Opthalmol Vis Sci., 43(10):3292-8 (2002).

Tepel, et al., "Prevention of radiographic-contrast-agent-induced reductions in renal function by acetylcysteine", NEJM, 343:180-4 (2000).

Thorne and Nicholson, "In vivo diffusion analysis with quantum dots and dextrans predicts the width of brain extracellular space", PNAS, 103(14):5567-72 (2006).

Till, et al., "Pexophagy: the selective degradation of peroxisomes", Int. J. Cell Biol. 2012:512721 (2012).

Tolar, et al.,, "N-acetyl-L-cysteine improves outcome of advanced cerebral adrenoleukodystrophy", Bone Marrow Transplant, 39(4), 211-215 (2007).

Tomalia et al., Dendrimers as multi-purpose nanodevices for oncology drug delivery and diagnostic imaging. Biochem Soc Trans. Feb. 2007;35(Pt 1):61-7. doi: 10.1042-BST0350061.

Tso, et al., "Apoptosis Leads To Photoreceptor Degeneration In Inherited RetinalDystrophy Of RCS Rats," Invest. Ophthalmol. Vis. Sci., 35(6):2693-9 (1994).

Tzeng, et al., "Therapeutic nanomedicine for brain cancer", Therapeutic Delivery, 4(6):1-29 (2013).

Vale et al., Paracetamol (acetaminophen) poisoning. Lancet. Aug. 26, 1995;346(8974):547-52. doi: 10.1016/s0140-6736(95)91385-8.

Van Schayck, et al., "Are anti-oxidant and anti-inflammatory treatments effective in different subgroups of COPD A hypothesis", Respir Med., 92:1259-64 (1998).

Vandamme, et al., "Poly(amidoamine) dendrimers as ophthalmic vehicles for ocular delivery of pilocarpine nitrate and tropicamide", J. Control. Rel., 102:23-28 (2005).

Viers, et al., "Hydrogels formed by Endlinking Peg to dendrimer crosslink agents", Polymer Reprints, 41(1):729 (2000).

Vincent, et al., "Efficacy of Dendrimer-Mediated Angiostatin and Timp-2 Gene Delivery on Inhibition of Tumor Growth and Angiogenesis: In Vitro and In Vivo Studies",Int. J. Cancer, 105:419-29 (2003).

Waite, et al., "Acetylation of PAMAM dendrimers for cellular delivery of siRNA", BMC Biotechnol., 9:38 (2009).

Wang et al., Inhibition of bacterial growth and intraamniotic infection in a guinea pig model of chorioamnionitis using PAMAM

(56) References Cited

OTHER PUBLICATIONS dendrimers. Int J Pharm. Aug. 16, 2010;395(1-2):298-308. doi: 10.1016/j.ijpharm.2010.05.030. Epub May 24, 2010. Author Manucript, 23 pages.

Wang, et al., "Anti-inflammatory and anti-oxidant activity of anionic dendrimer-N-acetylcysteine conjugates in activated microglial cells", Intl J Pharma, 377(1-2):159-68 (2009).

Waseem, et al., "Exogenous ghrelin modulates release of pro-inflammatory and anti-inflammatory cytokines in LPS stimulated macrophages through distinct signaling pathways", Surgery, 143(3):334-42 (2008).

Wells, et al., "Neuroprotection by minocycline facilitates significant recovery from spinal cord injury in mice", Brain, 126:162-37 (2003).

Wenzel, et al., "Prevention Of Photoreceptor Apoptosis By Activation Of The Glucocorticoid Receptor," Invest. Ophthalmol. Vis. Sci., 42(7):1653-9 (2001).

Wheeler, et al., "A defect of sphingolipid metabolism modifies the properties of normal appearing white matter in multiple sclerosis", Brain, 131:3092-3102 (2008).

Wiesinger, et al., "The genetic landscape of X-linked adrenoleukodystrophy: inheritance, mutations, modifier genes, and diagnosis", Appl Clin Genet., 8:109-21 (2015).

Wipf, et al., "Synthesis of anti-inflammatory a-and 13-linked acetamidopyranosides as inhibitors of toll-like receptor 4 (TLR4)", Tetrahedron Ltr., 56(23):3097-3100 (2015).

Wolf, et al., "OARS-associated leukoencephalopathy can mimic a steroid-responsive neuroinflammatory disorder", Neurology, 84(3):226-30 (2015).

Wong, et al., "Multistage nanoparticle delivery system for deep penetration into tumor tissue", PNAS, 108(6):2426-31 (2011).

Writer, et al., "Lipid peptide nanocomplexes for gene delivery and magnetic resonance imaging in the brain", J Control Release, 162(2):340-8 (2012).

Xu, et al., "Effect of N-acetylcysteine on lipopolysaccharide-induced intra-uterine fetal death and intra-uterine growth retardation in mice", Toxicol. Sci., 8B:525-33 (2005).

Yabroff, et al., "Patterns of care and survival for patients with glioblastoma multiforme diagnosed during 2006", Neuro-Oncology, 14(3):351-9 (2012).

Yang, et al., "Fas And Activation-Induced Fas Ligand Mediate Apoptosis of T Cell Hybridomas: Inhibition Of Fas Ligand Expression By Retinoic Acid And Glucocorticoids," J. Exp. Med., 181:1673-82 (1995).

You et al., Reducible poly(2-dimethylaminoethyl methacrylate): synthesis, cytotoxicity, and gene delivery activity. J Control Release. Oct. 8, 2007;122(3):217-225. doi: 10.1016/j.jconrel.2007.04.020. Epub May 10, 2007.

Zeng, et al., "Identification Of Sequential Events And Factors Associated With Microglial Activation, Migration, And Cytotoxicity In Retinal Degeneration In rd Mice," Invest. Ophthalmol. Vis. Sci. 46(8):2992-9 (2005).

Zhai, et al., "Microglia-Macrophages Promote Glioma Progression", Glia, 59(3):472-85 (2011).

Zhang, et al., "Neuroprotection Of Photoreceptors By Minocycline In Light-InducedRetinal Degeneration," Invest. Ophthalmol. Vis. Sci., 45:2753-9 (2004).

Zhang, et al., "Uniform brain tumor distribution and tumor associated macrophage targeting of systemically administered dendrimers", Biomaterials, 52:507-16 (2015).

Zhou, et al., "Highly penetrative, drug-loaded nanocarriers improve treatment of glioblastoma", PNAS, 110(29): 11751-6 (2013).

Zhu, et al., "Systemic Delivery of Neutralizing Antibody Targeting CCL2 for Glioma Therapy", J Neurooncol, 104(1):83-92 (2011).

Zhu, et al., Targeting of Tumor-Associated Macrophages Made Possible by PEG-Sheddable, Mannose-Modified Nanoparticles, Mol Pharma., 10:3525-30 (2013).

Zimmermann, et al., "Extracellular matrix of the central nervous system: from neglect to challenge", Histochem Cell Biol, 130(4):635-53 (2008).

9, N,N Didesethyl Sunitinib azide amide linker

Dendrimer-Didesethyl Sunitinib Amide-conjugate

DENDRIMER COMPOSITIONS AND METHODS FOR DRUG DELIVERY TO THE EYE

CROSS-REFERENCE TO RELATED APPLICATIONS

This application is a continuation of U.S. application Ser. No. 17/112,255, filed Dec. 4, 2020, which claims the benefit under 35 U.S.C. § 119(e) of U.S. Provisional Application No. 62/943,724, filed Dec. 4, 2019, U.S. Provisional Application No. 63/021,023, filed May 6, 2020, and U.S. Provisional Application No. 63/108,234, filed Oct. 30, 2020, each of which is incorporated by reference herein in its entirety.

FIELD OF THE INVENTION

The invention is generally in the field of drug delivery, and in particular, a method of delivering drugs selectively to activated immune cells within the eye and surrounding tissue.

BACKGROUND OF THE INVENTION

The development of neuroinflammatory changes in the retina is a significant factor in the pathogenesis of multiple retinal disorders including glaucoma, diabetic retinopathy, and age-related macular degeneration. Abnormal immune responses arising from physiological changes in microglia, the primary resident innate immune cell in the retina, are thought to drive aspects of disease progression, including neuronal degeneration and pathological neovascularization (Karlstetter et al., 2015; Silverman and Wong, 2018). Microglia are activated due to a complex interplay between the different cell types of the retina and diverse pathological pathways. Following activation, microglia cells lose their ramified protrusions, proliferate and rapidly migrate to the damaged areas and resolve tissue damage. However, sustained presence of tissue stress primes microglia to become over-reactive and results in the excessive production of pro-inflammatory mediators that favor retinal degenerative changes. A chronic pro-inflammatory environment is a hallmark of retinal degenerative diseases and neurological disorders that affect vision. Activation of retinal microglia also occurs in a mouse model of ischemia/reperfusion injury (I/R), as occurs in inflammatory diseases of the eye, including glaucoma, age related macular degeneration (AMD), diabetic retinopathy and branch vein occlusion. Retinal vascular occlusion, be it by high intra-ocular pressure in the I/R model or thrombus in BVO, causes a decrease in blood flow within the eye, resulting in retinal ischemia. This causes death of neurons initiating further activation of microglia.

Enhanced production of pro-inflammatory and angiogenic factors induces the formation and growth of new blood vessels from the choroid into the subretinal space, mimicking features of exudative AMD in a laser-induced CNV mouse model (Lambert V, et al., Nat. Protoc. 8, 2197-2211 (2013)). Several circumstances, such as ischemia, hypoxia or inflammation, can promote neovascularization. Pathological ocular angiogenesis, particularly in the retina and choroid, can lead to significant visual impairment. Diabetic retinopathy, neovascular age-related macular degeneration (AMD), retinopathy of prematurity, and retinal vessel occlusion are major causes of angiogenesis-related vision loss.

Exudative (wet form) AMD is characterized by serous or hemorrhagic separation of the retinal pigment epithelium or neurosensory layer. Patients may develop choroidal neovascularization (CNV), which is manifested as fluid accumulation, hemorrhage, and/or lipid exudation. The earliest stage of diabetic retinopathy (DR) is characterized by retinal vascular abnormalities including microaneurysms (saccular out-pouchings from the capillary wall), intraretinal hemorrhages, and cotton-wool spots (nerve fiber layer infarctions). As the disease progresses, the gradual closure of retinal vessels results in retinal ischemia, giving rise to signs including venous abnormalities (beading, loops), intraretinal microvascular abnormalities, and increasing retinal hemorrhage and exudation. Non-proliferative DR is graded as mild, moderate, severe, and very severe according to the presence and extent of the above lesions. The more advanced stage of DR involves the formation of new blood vessels, induced by the retinal ischemia, which spreads out either from the disc (neovascularization of the disc, NVD) or from elsewhere in the retina (neovascularization elsewhere, NVE). New vessels extending into the vitreous can cause vitreous hemorrhage, and tractional retinal detachments associated with accompanying contractile fibrous tissue.

To date, the only treatment conclusively demonstrated to be of long-term benefit for DR is focal laser photocoagulation. The standard treatment for patients with AMD is intravitreal injections of anti-VEGF into the eye to slow disease progression, and there have been studies that have shown that anti-VEGF therapy may be useful in diabetic macular edema (DME). However, there are at present no systemic treatments available for ischemic retinopathies or AMD. These would involve less frequent injections due to retention in microglia and ability to delivery systemically, avoiding frequent intraocular injections as in current anti-VEGF therapies.

Therefore, it is an object of the invention to provide compositions and methods for effective therapies for one or more inflammatory and/or angiogenic diseases of the eye, particularly DME, DR and AMD.

It is another object of the invention to provide compositions and methods for targeted delivery of one or more active agents to the diseased tissues/cells in the eye via systemic administration with increased efficacy and reduced side effects.

It is a further object to provide compositions and methods for targeted delivery of one or more active agents to activated microglia associated with one or more inflammatory and/or angiogenic diseases of the eye.

It is also an object to provide compositions and methods effective for inhibiting or reducing pro-inflammatory and/or angiogenic factors associated with one or more inflammatory and/or angiogenic diseases of the eye.

SUMMARY OF THE INVENTION

Compositions and methods for selective delivery of one or more therapeutic, prophylactic and/or diagnostic agents to treat and/or diagnose one or more diseases and/or disorders of the eye have been developed. The compositions deliver one or more therapeutic, prophylactic and/or diagnostic agents selectively to activated microglial cells to treat and/or diagnose diseases tissues/cells of the eye.

Compositions include hydroxyl-terminated dendrimer complexed, covalently conjugated or intra-molecularly dispersed or encapsulated with one or more receptor tyrosine kinase inhibitors in an amount effective to reduce the number or activity of the activated microglia and macrophages in the retina and/or the choroid in a subject in need thereof. In some embodiments, the receptor tyrosine kinase inhibitor is an inhibitor of vascular endothelial growth factor receptors such as sunitinib, sorafenib, pazopanib, vandetanib, axitinib, cediranib, vatalanib, dasatinib, nintedanib, motesanib, and analogues thereof. Preferably, the receptor tyrosine kinase inhibitor is sunitinib or an analogue thereof. In some embodiments, the diagnostic agents are dyes, such as fluorescent dyes, Near infra-red dyes, SPECT imaging agents, PET imaging agents and radioisotopes. Preferably, the diagnostic agent is the fluorescent dye indocyanine green (ICG).

In some embodiments, the dendrimer is a generation 4, generation 5, generation 6, generation 7, generation 8, generation 9, or generation 10 PAMAM dendrimer. In some embodiments, the one or more therapeutic, prophylactic and/or diagnostic agents are covalently conjugated to the dendrimers.

In some embodiments, the one or more therapeutic, prophylactic and/or diagnostic agents are at a concentration by weight of agent to dendrimer conjugate of between about 0.01% weight to weight (w/w) to about 30% w/w, about 1% w/w to about 25% w/w, about 5% w/w to about 20% w/w, and about 10% w/w to about 15% w/w.

In some embodiments, one or more spacers or linkers between a dendrimer and an agent are added to provide a releasable (or cleavable) or non-releasable (or non-cleavable) form of the dendrimer-agent complexes in vivo. In some embodiments, the attachment occurs via an appropriate spacer that provides an ester bond between the agent and the dendrimer. In some embodiments, the attachment occurs via an appropriate spacer that provides an ether bond between the agent and the dendrimer. In some embodiments, the attachment occurs via an appropriate spacer that provides an amide bond between the agent and the dendrimer. In preferred embodiments, one or more spacers/linkers between a dendrimer and an agent are tailored to achieve desired and effective release kinetics in vivo.

The compositions are suitable for treating and/or diagnosing one or more inflammatory and/or angiogenic diseases of the eye, for example, age-related macular degeneration (AMD), retinitis pigmentosa, optic neuritis, uveitis, retinal detachment, temporal arteritis, retinal ischemia, arteriosclerotic retinopathy, hypertensive retinopathy, retinal artery blockage, retinal vein blockage, diabetic retinopathy, macular edema, retinal neovascularization, and choroidal neovascularization.

Methods of making the dendrimer compositions are provided. Dosage forms and pharmaceutical formulations including an effective amount of the dendrimer compositions for administration to a subject in need thereof are also provided.

Methods of treating and/or diagnosing one or more diseases and/or disorders of the eye by administering to a subject in need thereof an effective amount of the compositions are described. The methods are effective in treating and/or diagnosing one or more diseases and/or disorders of the eye, including age-related macular degeneration (AMD), retinitis pigmentosa, optic neuritis, uveitis, retinal detachment, temporal arteritis, retinal ischemia, arteriosclerotic retinopathy, hypertensive retinopathy, retinal artery blockage, retinal vein blockage, diabetic retinopathy, macular edema, retinal neovascularization, and choroidal neovascularization. In particular, the methods are effective for treating and/or diagnosing one or more diseases and/or disorders of the eye associated with activated microglia within the eye and surrounding tissue. Typically, the compositions are administered in an amount effective to target the activated microglia, retinal pigment epithelia (RPE) cells, and/or choroidal neovascular (CNV) lesions, and/or to alleviate one or more symptoms of the one or more one or more diseases and/or disorders of the eye.

Methods of administering the compositions and pharmaceutical formulations are also provided. Typically, the compositions and pharmaceutical formulations are administered via one or more systemic routes daily, weekly, biweekly, monthly, bimonthly, or less frequently. In some embodiments, the compositions and pharmaceutical formulations are administered via one or more systemic routes once every four weeks or less frequently. In preferred embodiments, the compositions and pharmaceutical formulations are administered via the intravenous, subcutaneous, or oral route.

DETAILED DESCRIPTION OF THE INVENTION

I. Definitions

Figure 1A:
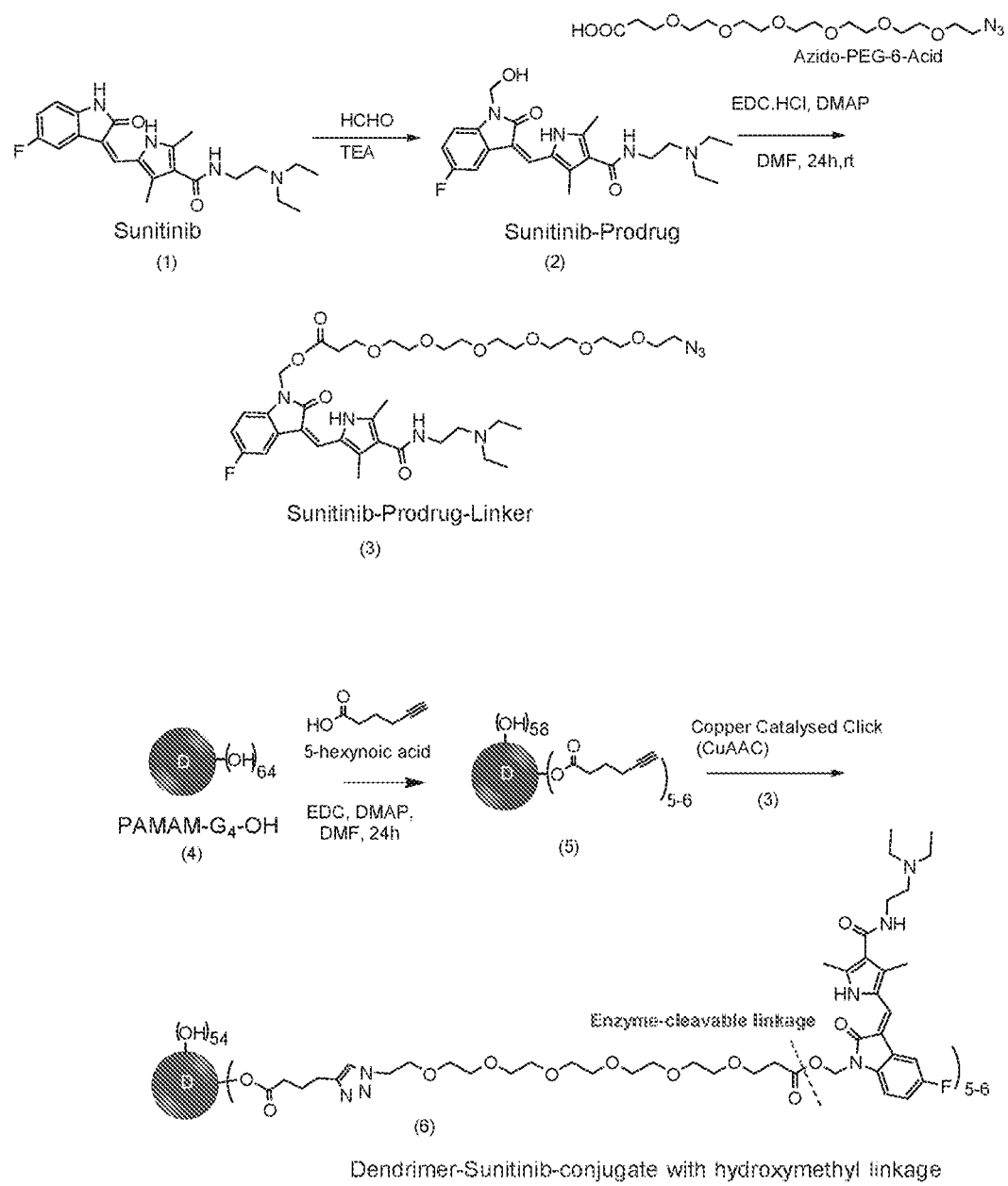
FIGS. 1A and 1B are schemes showing chemical reaction steps for the synthesis of a dendrimer-sunitinib conjugate. Sunitinib is conjugated to the dendrimer via a hydroxymethyl linkage (FIG. 1A), and an amide linkage (FIG. 1B), respectively.

The terms "active agent" or "biologically active agent" are therapeutic, prophylactic or diagnostic agents used interchangeably to refer to a chemical or biological compound that induces a desired pharmacological and/or physiological effect, which may be prophylactic, therapeutic or diagnostic. These may be a nucleic acid, a nucleic acid analog, a small molecule having a molecular weight less than 2 kDa, more typically less than 1 kDa, a peptidomimetic, a protein or peptide, carbohydrate or sugar, lipid, or surfactant, or a combination thereof. The terms also encompass pharmaceutically acceptable, pharmacologically active derivatives of active agents, including, but not limited to, salts, esters, amides, prodrugs, active metabolites, and analogs.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphemethylamine;

The term "therapeutic agent" refers to an active agent that can be administered to treat one or more symptoms of a disease or disorder.

The term "diagnostic agent" refers to an active agent that can be administered to reveal, pinpoint, and define the localization of a pathological process. The diagnostic agents can label target cells that allow subsequent detection or imaging of these labeled target cells. In some embodiments, diagnostic agents can, via dendrimer or suitable delivery vehicles, target/bind activated microglia, activated macrophages, and/or RPE cells.

The term "prophylactic agent" refers to an active agent that can be administered to prevent disease or to prevent certain conditions.

The phrase "pharmaceutically acceptable", or "biocompatible" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "therapeutically effective amount" refers to an amount of the therapeutic agent that, when incorporated into and/or onto dendrimers, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of one or more eye diseases or disorders, such as reducing inflammation by reducing or inhibiting one or more pro-inflammatory cytokines and/cells associated with the diseased tissues/cells in the eye. In the case of retinal and/or choroidal neovascularization, an effective amount of the drug may have the effect in reducing retinal and/or choroidal angiogenesis; inhibiting to some extent vascular endothelial cell growth/proliferation; and/or relieving to some extent one or more of the symptoms associated with the disorder. An effective amount can be administered in one or more administrations.

The terms "inhibit" or "reduce" in the context of inhibition, mean to reduce or decrease in activity and quantity. This can be a complete inhibition or reduction in activity or quantity, or a partial inhibition or reduction. Inhibition or reduction can be compared to a control or to a standard level. Inhibition can be 5, 10, 25, 50, 75, 80, 85, 90, 95, 99, or 100%. For example, dendrimer compositions including one or more therapeutic agents may inhibit or reduce the activity and/or quantity of activated microglia and macrophages in the diseased retina and/or choroid of a subject by about 10%, 20%, 30%, 40%, 50%, 75%, 85%, 90%, 95%, or 99% from the activity and/or quantity of the same cells in equivalent diseased tissues of subjects that did not receive, or were not treated with the dendrimer compositions (i.e., un-conjugated active agents). In some embodiments, the inhibition and reduction are compared at mRNAs, proteins, cells, tissues and organs levels. For example, an inhibition and/or reduction in pro-inflammatory cytokines (e.g., TNF-α, interleukin-1β (IL-1β), or interferon-γ (IFN-γ)) secreted by the activated microglia and macrophages in the diseased retina and/or choroid.

The term "treating" or "preventing" a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. Desirable effects of treatment include decreasing the rate of disease progression, ameliorating or palliating the disease state, and remission or improved prognosis. For example, an individual is successfully "treated" if one or more symptoms associated with an eye disease or disorder are mitigated or eliminated, including, but are not limited to, reducing the proliferation of pro-inflammatory cells, decreasing symptoms resulting from the disease, enhancing or restoring vision, decreasing the extent and rate of vision loss, increasing the quality of life of those suffering from the disease, decreasing the dose of other medications required to treat the disease, delaying the progression of the disease, and/or prolonging survival of individuals.

The term "biodegradable" refers to a material that will degrade or erode under physiologic conditions to smaller units or chemical species that are capable of being metabolized, eliminated, or excreted by the subject. The degradation time is a function of composition and morphology.

The term "dendrimer" includes, but is not limited to, a molecular architecture with an interior core, interior layers (or "generations") of repeating units regularly attached to this initiator core, and an exterior surface of terminal groups attached to the outermost generation.

The term "functionalize" means to modify a compound or molecule in a manner that results in the attachment of a functional group or moiety. For example, a molecule may be functionalized by the introduction of a molecule which makes the molecule a strong nucleophile or strong electrophile.

The term "targeting moiety" refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type or cell activation state, or a subcellular compartment. In some embodiments, the targeting moiety directs the localization of an active agent.

The term "prolonged residence time" refers to an increase in the time required for an agent to be cleared from a patient's body, or organ or tissue of that patient. In certain embodiments, "prolonged residence time" refers to an agent that is cleared with a half-life that is 10%, 20%, 50% or 75% longer than a standard of comparison such as a comparable agent without conjugation to a delivery vehicle such as a dendrimer. In certain embodiments, "prolonged residence time" refers to an agent that is cleared with a half-life of 2, 5, 10, 20, 50, 100, 200, 500, 1000, 2000, 5000, or 10000 times longer than a standard of comparison such as a comparable agent without a dendrimer that specifically target specific cell types associated with tumors.

The terms "incorporated" and "encapsulated" refer to incorporating, formulating, or otherwise including an active agent into and/or onto a composition that allows for release, such as sustained release, of such agent in the desired application. The active agent or other material can be incorporated into a dendrimer, including to one or more surface functional groups of such dendrimer (by covalent, ionic, or other binding interaction), physical admixture, enveloping the agent within the dendritic structure, encapsulated inside the dendritic structure, etc.

II. Compositions

Dendrimer complexes suitable for delivering one or more active agent, particularly one or more active agents to prevent, treat or diagnose one or more diseases or disorders of the eye.

Compositions of dendrimer complexes include one or more prophylactic, therapeutic, and/or diagnostic agents encapsulated, associated, and/or conjugated in the dendrimer complex at a concentration by weight of about 0.01% weight to weight (w/w) to about 30% w/w, about 1% w/w to about 25% w/w, about 5% w/w to about 20% w/w, and about 10% w/w to about 15% w/w. In some embodiments, prophylactic, therapeutic, and/or diagnostic agents are covalently conjugated to the dendrimer via one or more linkages selected from disulfide, ester, ether, thioester, carbamate, carbonate, hydrazine, and amide, optionally via one or more spacers. Preferably, hydroxyl groups of hydroxyl-terminated dendrimers are covalently conjugated to one or more active agents via at least one ether linkage, optionally via one or more linkers/spacers. In preferred embodiments, surface groups of hydroxyl-terminated dendrimers are modified via etherification reaction prior to conjugation to one or more linkers and the active agent. Where one or more linkers are present between dendrimers and active agents, the covalent bond between the surface groups of dendrimers and the linkers are ether bonds. In other embodiments, at dendrimer generation 3.5, alkyne functional groups are introduced using a polyethyl glycol (PEG) linker with an amine at one end and a hexyne at the other end to produce a generation 4 bifunctional dendrimer. An exemplary bifunctional dendrimer is shown as compound 1 in FIG. 11 with 7 alkyne arms and 57 hydroxyl groups on the surface.

In some embodiments, the spacer is a prophylactic, therapeutic, and/or diagnostic agent, such as sunitinib. Exemplary active agents include antiangiogenic agents, anti-inflammatory drugs, and anti-infective agents.

The presence of the additional agents can affect the zeta-potential, or the surface charge of the particle. In one embodiment, the zeta potential of the dendrimers is −100 mV and 100 mV, between −50 mV and 50 mV, between −25 mV and 25 mV, between −20 mV and 20 mV, between −10 mV and 10 mV, between −10 mV and 5 mV, between −5 mV and 5 mV, or between −2 mV and 2 mV. In a preferred embodiment, the surface charge is neutral or near-neutral. The range above is inclusive of all values from −100 mV to 100 mV.

A. Dendrimers

Dendrimers are three-dimensional, hyperbranched, monodispersed, globular and polyvalent macromolecules having a high density of surface end groups (Tomalia, D. A., et al., Biochemical Society Transactions, 35, 61 (2007); and Sharma, A., et al., ACS Macro Letters, 3, 1079 (2014)). Due to their unique structural and physical features, dendrimers are useful as nano-carriers for various biomedical applications including targeted drug/gene delivery, imaging and diagnosis (Sharma, A., et al., RSC Advances, 4, 19242 (2014); Caminade, A.-M., et al., Journal of Materials Chemistry B, 2, 4055 (2014); Esfand, R., et al., Drug Discovery Today, 6, 427 (2001); and Kannan, R. M., et al., Journal of Internal Medicine, 276, 579 (2014)).

Dendrimer surface groups have a significant impact on their biodistribution (Nance, E., et al., Biomaterials, 101, 96 (2016)). Hydroxyl terminated generation 4 PAMAM dendrimers (~4 nm size) without any targeting ligand cross the impaired BBB upon systemic administration in a rabbit model of cerebral palsy (CP) significantly more (>20 fold) as compared to healthy controls, and selectively target activated microglia and astrocytes (Lesniak, W. G., et al., Mol Pharm, 10 (2013)).

The term "dendrimer" includes a molecular architecture with an interior core and layers (or "generations") of repeating units which are attached to and extend from this interior core, each layer having one or more branching points, and an exterior surface of terminal groups attached to the outermost generation. In some embodiments, dendrimers have regular dendrimeric or "starburst" molecular structures.

Generally, dendrimers have a diameter from about 1 nm up to about 50 nm, more preferably from about 1 nm to about 20 nm, from about 1 nm to about 10 nm, or from about 1 nm to about 5 nm. In some embodiments, the diameter is between about 1 nm to about 2 nm. Conjugates are generally in the same size range, although large proteins such as antibodies may increase the size by 5-15 nm. In general, agent is encapsulated in a ratio of agent to dendrimer of between 1:1 to 4:1 for the larger generation dendrimers. In preferred embodiments, the dendrimers have a diameter effective to penetrate ocular tissue and to be retained in target cells for a prolonged period of time.

In some embodiments, dendrimers have a molecular weight between about 500 Daltons to about 100,000 Daltons, preferably between about 500 Daltons to about 50,000 Daltons, most preferably between about 1,000 Daltons to about 20,000 Dalton.

Suitable dendrimers scaffolds that can be used include poly(amidoamine), also known as PAMAM, or STARBURST™ dendrimers; polypropylamine (POPAM), polyethylenimine, polylysine, polyester, iptycene, aliphatic poly (ether), and/or aromatic polyether dendrimers. The dendrimers can have carboxylic, amine and/or hydroxyl terminations. In preferred embodiments, the dendrimers have hydroxyl terminations. Each dendrimer of the dendrimer complex may be same or of similar or different chemical nature than the other dendrimers (e.g., the first dendrimer may include a PAMAM dendrimer, while the second dendrimer may be a POPAM dendrimer).

The term "PAMAM dendrimer" means poly(amidoamine) dendrimer, which may contain different cores, with amidoamine building blocks, and can have carboxylic, amine and hydroxyl terminations of any generation including, but not limited to, generation 1 PAMAM dendrimers, generation 2 PAMAM dendrimers, generation 3 PAMAM dendrimers, generation 4 PAMAM dendrimers, generation 5 PAMAM dendrimers, generation 6 PAMAM dendrimers, generation 7 PAMAM dendrimers, generation 8 PAMAM dendrimers, generation 9 PAMAM dendrimers, or generation 10 PAMAM dendrimers. In the preferred embodiment, the dendrimers are soluble in the formulation and are generation ("G") 4, 5 or 6 dendrimers. In preferred embodiments, dendrimers have a plurality of hydroxyl groups attached to their functional surface groups.

Methods for making dendrimers are known to those of skill in the art and generally involves a two-step iterative reaction sequence that produces concentric shells (generations) of dendritic β-alanine units around a central initiator core (e.g., ethylenediamine-cores). Each subsequent growth step represents a new "generation" of polymer with a larger molecular diameter, twice the number of reactive surface sites, and approximately double the molecular weight of the preceding generation. Dendrimer scaffolds suitable for use are commercially available in a variety of generations. Preferable, the dendrimeric compounds are based on generation 0, 1, 2, 3, 4, 5, 6, 7, 8, 9, or 10 dendrimeric scaffolds. Such scaffolds have, respectively, 4, 8, 16, 32, 64, 128, 256, 512, 1024, 2048, and 4096 reactive sites. Thus, the dendrimeric compounds based on these scaffolds have the corresponding number of combined targeting moieties and modulators.

In some embodiments, the dendrimers include a plurality of hydroxyl groups. Some exemplary high-density hydroxyl groups-containing dendrimers include commercially available polyester dendritic polymer such as hyperbranched 2,2-Bis(hydroxyl-methyl)propionic acid polyester polymer (for example, hyperbranched bis-MPA polyester-64-hydroxyl, generation 4), dendritic polyglycerols.

In some embodiments, the high-density hydroxyl groups-containing dendrimers are oligo ethylene glycol (OEG)-like dendrimers. For example, a generation 2 OEG dendrimer (D2-OH-60) can be synthesized using highly efficient, robust and atom economical chemical reactions such as Cu (I) catalyzed alkyne-azide click and photo catalyzed thiolene click chemistry. Highly dense polyol dendrimer at very low generation in minimum reaction steps can be achieved by using an orthogonal hypermonomer and hypercore strategy, for example as described in WO 2019094952. In some embodiments, dendrimer backbone has non-cleavable polyether bonds throughout the structure to avoid the disintegration of dendrimer in vivo, and to allow the elimination of such dendrimers as a single entity from the body (non-biodegradable).

In some embodiments, the dendrimer is able to specifically target a particular tissue region and/or cell type, preferably activated microglia and macrophages associated with one or more eye diseases. In preferred embodiments, the dendrimer is able to specifically target a particular tissue region and/or cell type without addition of a targeting moiety.

In preferred embodiments, the dendrimers have a plurality of hydroxyl (—OH) groups on the surface of the dendrimers. The preferred surface density of hydroxyl (—OH) groups is at least 1 OH group/nm$^2$ (number of hydroxyl surface groups/surface area in nm$^2$). For example, in some embodiments, the surface density of hydroxyl groups is more than 2, 3, 4, 5, 6, 7, 8, 9, 10; preferably at least 10, 15, 20, 25, 30, 35, 40, 45, 50, or more than 50 surface groups/surface area in nm$^2$. In further embodiments, the surface density of hydroxyl (—OH) groups is between about 1 and about 50, preferably 5-20 OH group/nm$^2$ (number of hydroxyl surface groups/surface area in nm$^2$) while having a molecular weight of between about 500 Da and about 10 kDa. In preferred embodiments, the percentage of free, i.e., un-conjugated hydroxyl groups out of total surface groups (conjugated and un-conjugated) on the dendrimer is more than 70%, 75%, 80%, 85%, 90%, 95%, and/or less than 100%. In the case of generation 4 PAMAM dendrimers, the preferred number of free, i.e., un-conjugated hydroxyl groups is more than 50, 51, 52, 53, 54, 55, 56, 57, 58, 59, 60, 61, 62, or 63 out of total 64 surface terminals/groups. In further embodiments, the hydroxyl terminated dendrimers have an effective number of free hydroxyl groups for selective targeting to activated microglia, activated microphages, and/or RPE cells associated with one or more diseases and/or disorders of the eye.

In some embodiments, the dendrimers may have a fraction of the hydroxyl groups exposed on the outer surface, with the others in the interior core of the dendrimers. In preferred embodiments, the dendrimers have a volumetric density of hydroxyl (—OH) groups of at least 1 OH group/$nm^3$ (number of hydroxyl groups/volume in $nm^3$). For example, in some embodiments, the volumetric density of hydroxyl groups is 2, 3, 4, 5, 6, 7, 8, 9, 10, or more than 10, 15, 20, 25, 30, 35, 40, 45, and 50 hydroxyl groups/volume in $nm^3$. In some embodiments, the volumetric density of hydroxyl groups is between about 4 to about 50 hydroxyl groups/$nm^3$, preferably between about 5 to about 30 hydroxyl groups/$nm^3$, more preferably between about 10 to about 20 hydroxyl groups/$nm^3$.

B. Coupling Agents and Spacers

Dendrimer complexes can be formed of therapeutically active agents or compounds conjugated or attached to a dendrimer, a dendritic polymer or a hyperbranched polymer. Optionally, the active agents are conjugated to the dendrimers via one or more spacers/linkers via different linkages such as disulfide, ester, carbonate, carbamate, thioester, hydrazine, hydrazides, and amide linkages. The one or more spacers/linkers between a dendrimer and an agent can be designed to provide a releasable (or cleavable) or non-releasable (or non-cleavable) form of the dendrimer-active complexes in vivo. In some embodiments, the attachment occurs via an appropriate spacer that provides an ester bond between the agent and the dendrimer. In some embodiments, the attachment occurs via an appropriate spacer that provides an amide bond between the agent and the dendrimer. In preferred embodiments, one or more spacers/linkers between a dendrimer and an agent are added to achieve a desired and effective release kinetics in vivo. In further embodiments, the conjugation of dendrimer and/or linker does not significantly affect the activities of the active agents. For example, in the case of VEGFR TKR inhibitors, they retain their binding affinity towards one or more of VEGFR TKR after conjugation to dendrimers at a level comparable to unconjugated VEGFR TKR inhibitors.

The term "spacer" includes moieties and compositions used for linking a therapeutically active agent to the dendrimer. The spacer can be either a single chemical entity or two or more chemical entities linked together to bridge the dendrimer and the active agent. The spacers can include any small chemical entity, peptide or polymers having sulfhydryl, thiopyridine, succinimidyl, maleimide, vinylsulfone, and carbonate terminations.

The spacer can be chosen from among a class of compounds terminating in sulfhydryl, thiopyridine, succinimidyl, maleimide, vinylsulfone and carbonate group. The spacer can include thiopyridine terminated compounds such as dithiodipyridine, N-Succinimidyl 3-(2-pyridyldithio)-propionate (SPDP), Succinimidyl 6-(3-[2-pyridyldithio]-propionamido)hexanoate LC-SPDP or Sulfo-LC-SPDP. The spacer can also include peptides wherein the peptides are linear or cyclic essentially having sulfhydryl groups such as glutathione, homocysteine, cysteine and its derivatives, arg-gly-asp-cys (RGDC), cyclo(Arg-Gly-Asp-d-Phe-Cys) (c(RGDfC)), cyclo(Arg-Gly-Asp-D-Tyr-Cys), and cyclo(Arg-Ala-Asp-d-Tyr-Cys). In some embodiments, the spacer includes a mercapto acid derivative such as 3 mercapto propionic acid, mercapto acetic acid, 4 mercapto butyric acid, thiolan-2-one, 6 mercaptohexanoic acid, 5 mercapto valeric acid and other mercapto derivatives such as 2 mercaptoethanol and 2 mercaptoethylamine. In some embodiments, the spacer includes thiosalicylic acid and its derivatives, (4-succinimidyloxycarbonyl-methyl-alpha-2-pyridylthio)toluene, (3-[2-pyridithio]propionyl hydrazide. In some embodiments, the spacer includes maleimide terminations wherein the spacer includes polymer or small chemical entity such as bis-maleimido diethylene glycol and bis-maleimido triethylene glycol, Bis-Maleimidoethane, and bismaleimidohexane. In some embodiments, the spacer includes vinylsulfone such as 1,6-Hexane-bis-vinylsulfone. In some embodiments, the spacer includes thioglycosides such as thioglucose. In other embodiments, the spacer includes reduced proteins such as bovine serum albumin and human serum albumin, any thiol terminated compound capable of forming disulfide bonds. In particular embodiments, the spacer includes polyethylene glycol having maleimide, succinimidyl and thiol terminations.

The therapeutically active agent, imaging agent, and/or targeting moiety can be either covalently attached or intramolecularly dispersed or encapsulated. The dendrimer is preferably a PAMAM dendrimer of generation 1 (G1), G2, G3, G4, G5, G6, G7, G8, G9 or G10, having carboxylic, hydroxyl, or amine terminations. In preferred embodiments, the dendrimer is linked to active agents via a spacer ending in ether or amide bonds.

In some embodiments, a non-releasable form of the dendrimer/active agent complex provides enhanced therapeutic efficacy as compared to a releasable or cleavable form of the same dendrimer/active agent complex. Therefore, in some embodiments, one or more active agent(s) is conjugated to the dendrimer via a spacer that is attached to the dendrimer in a non-releasable manner, for example, by an ether or amide bond. In some embodiments, one or more active agent(s) is attached to the spacer in a non-releasable manner, for example, by an ether or amide bond. Therefore, in some embodiments, one or more active agent(s) is attached to the dendrimer via a spacer that is attached to the dendrimer, and to the active agent(s) in a non-releasable manner. In an exemplary embodiment, one or more active agent(s) is attached to the dendrimer via a spacer that is attached to the dendrimer and the active agent(s) via amide and/or ether bonds. An exemplary spacer is polyethylene glycol (PEG).

1. Dendrimer Conjugation to Active Agents Via Ether Linkages

In some embodiments, the compositions include a hydroxyl-terminated dendrimer conjugated to an active agent via an ether linkage, optionally with one or more linkers/spacers.

In preferred embodiments, the covalent bonds between the surface groups of the dendrimers and the linkers, or the dendrimers and the active agent (if conjugated without any linking moieties) are stable under in vivo conditions, i.e., minimally cleavable when administered to a subject and/or excreted intact from the body. For example, in preferred embodiments, less than 10%, 5%, 4%, 3%, 2%, 1%, 0.5%, 0.4%, 0.3%, 0.2%, 0.1%, or less than 0.1% of the total dendrimer complexes have active agent cleaved within 24 hours, or 48 hours, or 72 hours after in vivo administration. In one embodiment, the covalent bonds are ether bonds. In further preferred embodiments, the covalent bond between the surface groups of the dendrimers and the linkers, or the dendrimers and the active agent (if conjugated without any linking moieties), are not hydrolytically or enzymatically cleavable bonds, such as ester bonds.

In some embodiments, one or more hydroxyl groups of hydroxyl-terminated dendrimers conjugate to one or more linking moieties and one or more active agents via one or more ether bonds as shown in Formula (I) below.

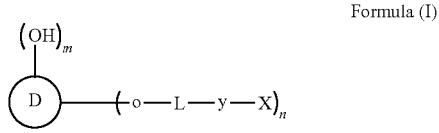

Formula (I)

wherein D is a G2 to G10 poly(amidoamine) (PAMAM) dendrimer; L is one or more linking moieties or spacers; X is an active agent or analog thereof; n is an integer from 1 to 100; and m is an integer from 16 to 4096; and Y is a linker selected from secondary amides (—CONH—), tertiary amides (—CONR—), sulfonamide (—S(O)$_2$—NR—), secondary carbamates (—OCONH—; —NHCOO—), tertiary carbamates (—OCONR—; —NRCOO—), carbonate (—O—C(O)—O—), ureas (—NHCONH—; —NRCONH—; —NHCONR—, —NRCONR—), carbinols (—CHOH—, —CROH—), disulfide groups, hydrazones, hydrazides, and ethers (—O—), wherein R is an alkyl group, an aryl group, or a heterocyclic group. Preferably, Y is a bond or linkage that is minimally cleavable in vivo.

In some embodiments, X is an inhibitor of vascular endothelial growth factor receptor (VEGFR) and/or TIE2 receptor tyrosine kinases.

In a preferred embodiment, Y is a secondary amide (—CONH—).

In one embodiment, D is a generation 4 PAMAM dendrimer; L is one or more linking or spacer moieties; X is sunitinib, or analog thereof; n is about 5-15; m is an integer about 49-59; and where n+m=64.

In another embodiment, D is a generation 4 PAMAM dendrimer; L is one or more linking or spacer moieties; X is N,N-didesethyl sunitinib; Y is a secondary amide (—CONH—); n is about 5-15; m is an integer about 49-59; and where n+m=64.

In a specific embodiment, the Formula I has the following structure (also referred to as D-4517.2):
Structure I: Chemical Structure of D-4517.2 the same dendrimers. In some embodiments, one or more types of active agents are encapsulated, complexed or conjugated to the dendrimer. In another embodiment, the dendrimers are covalently linked to at least one detectable moiety, in an amount effective to detect one or more diseased or injured cells/tissues in the subject. In particular embodiments, the dendrimer composition has multiple agents, such as an immunotherapeutic agent, an anti-seizure agent, a steroid to decrease swelling, an antibiotic, an anti-angiogenic agent, and/or a diagnostic agent, complexed with or conjugated to the dendrimers. In some embodiment, the dendrimers are complexed with or conjugated to two or more different classes of active agents, providing simultaneous delivery with different or independent release kinetics at the target site. For example, both sunitinib and an anti-inflammatory agent can be conjugated onto the same dendrimer for delivery to target cells/tissues. In a further embodiment, dendrimer complexes each carrying different classes of active agents are administered simultaneously for a combination treatment. In some embodiments, one or more therapeutic agents targeting the underlying cause of the disease or condition, and one or more therapeutic agents relieving one or more symptoms of the disease or condition.

Suitable active agents include therapeutic, diagnostic, and/or prophylactic agents. The agent can be a biomolecule, such as an enzyme, protein, polypeptide, or nucleic acid or a small molecule agent (e.g., molecular weight less than 2000 Dalton, preferably less than 1500 Dalton, more preferably 300-700 Dalton), including organic, inorganic, and organometallic agents. The agent can be encapsulated within the dendrimers, dispersed within the dendrimers, and/or associated with the surface of the dendrimer, either covalently or non-covalently. Exemplary therapeutic agents include anti-inflammatory drugs, anti-angiogenic agents, anti-oxidants, vasodilators, neuroactive agents, neuroprotective agents and anti-infective agents. In some embodiments, the dendrimer is linked to the targeting moiety, imaging agents, and/or therapeutic agents via a linker or spacer ending in disulfide, ester, ether, thioester, carbamate, carbonate, hydrazine, or amide bonds.

The dendrimers can be used to deliver one or more additional active agents, particularly one or more active agents to prevent or treat one or more symptoms of the eye diseases. Exemplary therapeutic agents administered with dendrimers include tyrosine kinase inhibitors such as

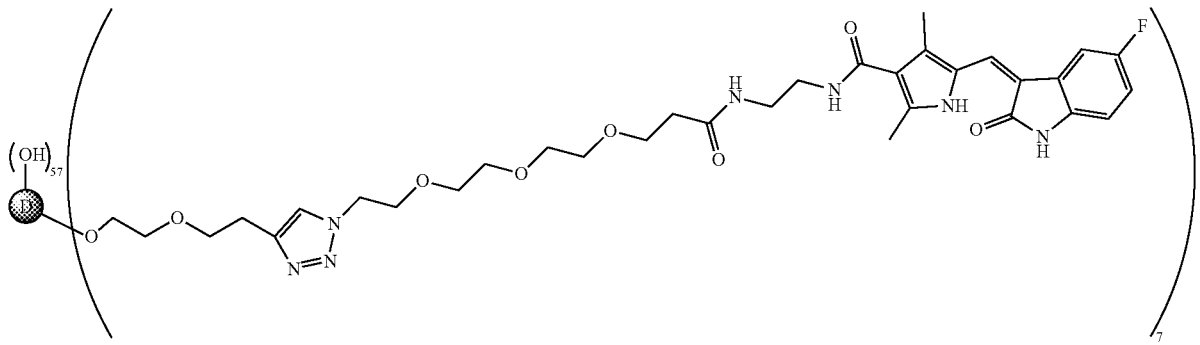

D-4517.2

C. Therapeutic, Prophylactic and Diagnostic Agents

Dendrimers have the advantage that multiple therapeutic, prophylactic, and/or diagnostic agents can be delivered with VEGFR tyrosine kinase inhibitors. In a preferred embodiment, the agents are small molecule tyrosine kinase inhibitors.

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Other active agents suitable for anti-angiogenic therapies include those targeting members of the platelet-derived growth factor family, epidermal growth factor family, fibroblast growth factor family, transforming growth factor-β superfamily (TGF-β1, activins, follistatin and bone morphogenetic proteins), angiopoietin-like family, galectins family, integrin superfamily, as well as pigment epithelium derived factor, hepatocyte growth factor, angiopoietins, endothelins, hypoxia-inducible factors, insulin-like growth factors, cytokines, matrix metalloproteinases and their inhibitors and glycosylation proteins.

Tyrosine Kinase Inhibitor

In some embodiments, the dendrimers are complexed or conjugated with one or more tyrosine kinase inhibitors.

Tyrosine kinases are important cellular signaling proteins that have a variety of biological activities including cell proliferation and migration. Multiple kinases are involved in angiogenesis, including receptor tyrosine kinases such as the vascular endothelial growth factor receptor (VEGFR). Anti-angiogenic tyrosine kinase inhibitors in clinical development primarily target VEGFR-1, -2, -3, epidermal growth factor receptor (EGFR), platelet-derived growth factor receptor (PDGFR), PDGFR-β, KIT, fms-related tyrosine kinase 3 (FLT3), colony stimulating factor-1 receptor (CSF-1R), Raf, and RET.

VEGFR Inhibitor

In some embodiments, the dendrimers are complexed or conjugated with one or more VEGFR tyrosine kinase inhibitors. The VEGFR family includes three related receptor tyrosine kinases, known as VEGFR-1, -2, and -3, which mediate the angiogenic effect of VEGF ligands (Hicklin D J, Ellis L M. J Clin Oncol. (2005), 23(5):1011-27). The VEGF family encoded in the mammalian genome includes five members: VEGF-A, VEGF-B, VEGF-C, VEGF-D, and placental growth factor (PlGF). VEGFs are important stimulators of proliferation and migration of endothelial cells. Increased expression of the angiogenic factor VEGF-A promotes three common aging-related eye conditions—"wet" and "dry" forms of age-related macular degeneration and also cataracts in an animal model (Marneros A G, EMBO Molecular Medicine, 2016; 8 (3): 208). Thus, in some embodiments, dendrimers are conjugated to one or more active agents effective in reducing the quantity and/or activity of one or more of VEGF-A, VEGF-B, VEGF-C, VEGF-D, and placental growth factor (PlGF).

Most notable angiogenesis inhibitors target the vascular endothelial growth factor signaling pathway, such as the monoclonal antibody bevacizumab (AVASTIN®, Genentech/Roche) and two kinase inhibitors sunitinib (SU11248, SUTENT®, Pfizer) and sorafenib (BAY43-9006, NEXAVAR®, Bayer). Bevacizumab was the first angiogenesis inhibitor that was clinically approved, initially for treatment of colorectal cancer and recently also for breast cancer and lung cancer. Another anti-VEGF agent clinically available is pegaptanib sodium, an aptamer for neovascular AMD. Unlike bevacizumab, which binds all VEGF isoforms, pegaptanib targets only VEGF165, the isoform responsible for pathological ocular neovascularization. In some embodiments, dendrimers are conjugated to one or more VEGF inhibitors including bevacizumab and pegaptanib sodium.

The small-molecule tyrosine kinase inhibitors sunitinib and sorafenib target the VEGF receptor (VEGFR), primarily VEGFR-2. Both drugs have shown benefit in patients with renal cell cancer (Motzer R J, Bukowski R M, J Clin Oncol. (2006); 24(35):5601-8). Sunitinib is a potent inhibitor of angiogenesis, with a rabbit model of corneal neovascularization suggesting topical sunitinib is almost three times as effective as bevacizumab (Pérez-Santonja J J et al., Am J Ophthalmol. 2010 October; 150(4):519-528). Sorafenib inhibits Raf serine kinase. Cediranib is an oral tyrosine kinase inhibitor of VEGF receptor (VEGFR).

Figure 1B:
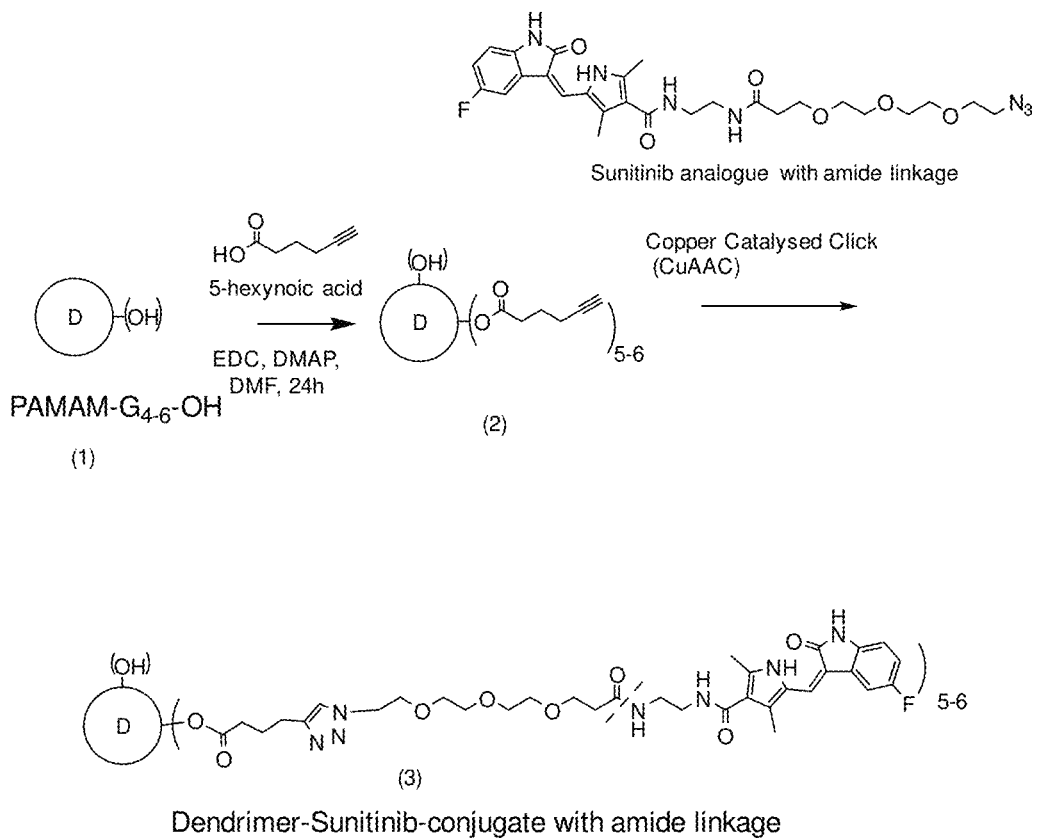

In some embodiments, dendrimers are conjugated to one or more VEGF receptor inhibitors including Sunitinib (SU11248; SUTENT®), Sorafenib (BAY439006; NEXAVAR®), Pazopanib (GW786034; VOTRIENT®), Vandetanib (ZD6474; ZACTIMA®), Axitinib (AG013736), Cediranib (AZD2171; RECENTIN®), Vatalanib (PTK787; ZK222584), Dasatinib, Nintedanib, and Motesanib (AMG706). In preferred embodiments, the VEGF receptor inhibitors can be functionalized with one or more spacers/linkers, for example with ether, ester, or amide linkage, for ease of conjugation with the dendrimers and/or for desired release kinetics. For example, sunitinib can be modified to sunitinib with an ester linkage, or with an amide linkage (FIGS. 1A and 1B). Exemplary conjugation of a VEGF receptor inhibitor, e.g., sunitinib to a dendrimer is shown in FIG. 1A (via a hydroxymethyl linkage) and FIG. 1B (via an amide linkage). In preferred embodiments, the conjugation of dendrimer and/or one or more linkers does not significantly affect the activities of the active agents. In further preferred embodiments, a VEGF receptor inhibitor is conjugated to dendrimers with or without a spacer in such a way that it minimizes the reduction in inhibition, for example, less than 1-fold, 2-fold, 3-fold, 4-fold, 5-fold, 10-fold, 20-fold, 30-fold, 40-fold, 50-fold, and 100-fold. For example in the case of sunitinib, it retains its binding affinity towards one or more of VEGFR TKR after conjugation to dendrimers at a level comparable to unconjugated sunitinib.

Additional VEGF receptor inhibitors with a functional spacer/linkage are shown below.

Structure II a-b: Chemical Structures of Sorafenib Analogues
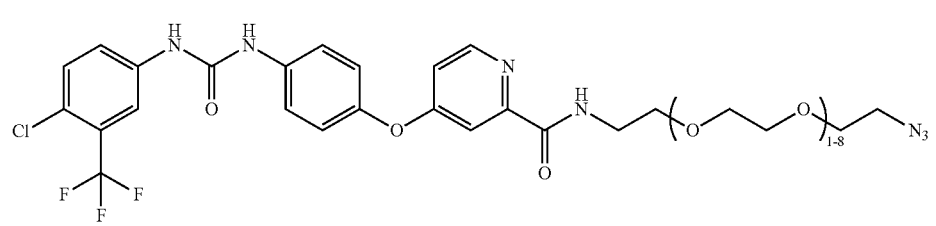
a
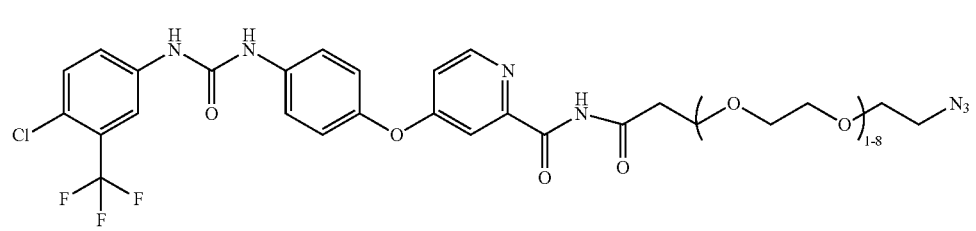
b
Structure III a-d: Chemical Structure of Nintedanib Analogue 1
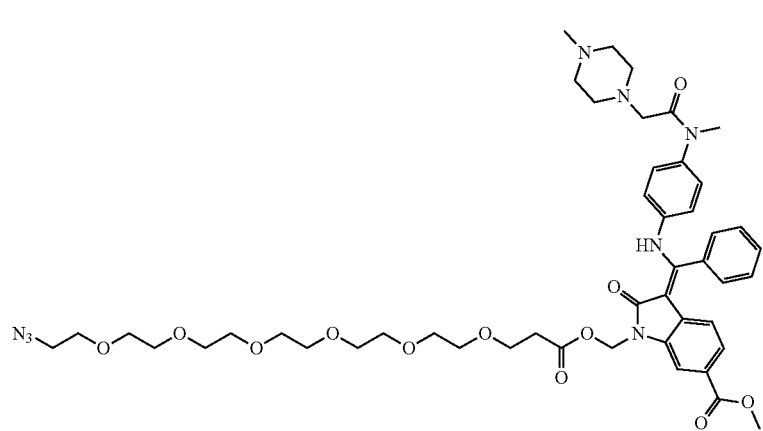
a
Nintedanib-hydromethyl-linker azide
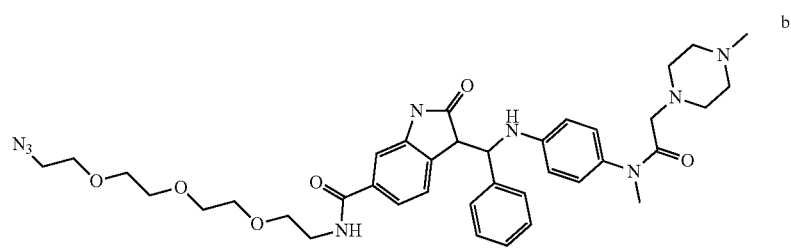
b
Nintedanib-amide-linker azide

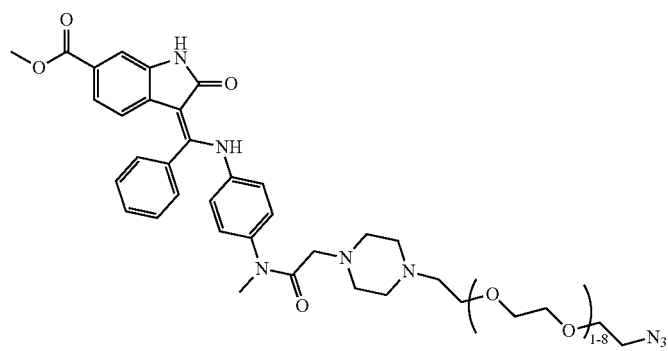

c

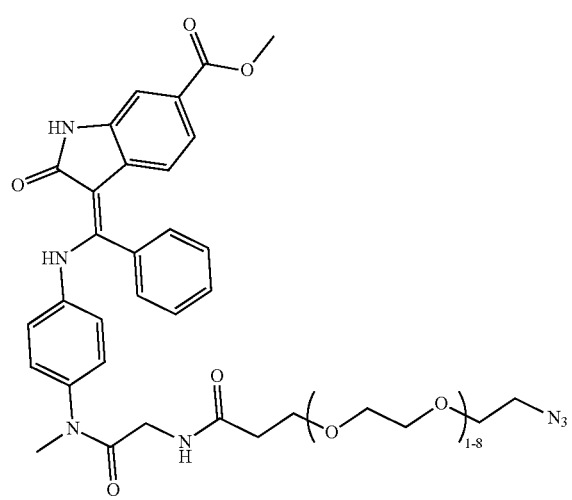

d

Structure IV: Chemical Structure of Orantinib Analogue

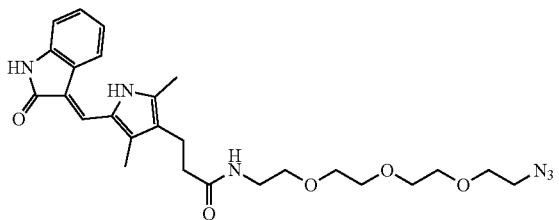 [SMILES: Cc1[nH]c(/C=C2/C(=O)Nc3ccccc32)c(C)c1CCC(=O)NCCOCCOCCOCCN=[N+]=[N-]]

Orantinib-Amide-Linker Azide

In some embodiments, the dendrimer complexes including one or more VEGF receptor inhibitors are administered in an amount effective to reduce or inhibit endothelial cells angiogenesis and/or vascular endothelial cell proliferation, to reduce retinal and/or choroidal angiogenesis and/or to relieve to one or more of the symptoms associated with the disease or disorder of the eye.

TIE II Antagonists

In some embodiments, the dendrimers are complexed or conjugated with one or more inhibitors of TIE II. Angiopoietin-1 receptor, also known as CD202B (cluster of differentiation 202B) and TIE II, is a protein that in humans is encoded by the TEK gene. TIE2 is an angiopoietin receptor. The angiopoietins are protein growth factors required for the formation of blood vessels (angiogenesis), which supports tumor growth and development. Therefore, in some embodiments, dendrimers are conjugated to one or more TIE II antagonists.

In some embodiments, the active agents are inhibitors of TIE II receptor tyrosine kinase. Exemplary inhibitors of VEGFR/TIE II include CEP-11981 and rebastinib. The TIE II antagonists can be functionalized, for example with ether, ester, ethyl, or amide linkage, for ease of conjugation with the dendrimers and/or for desired release kinetics. The chemical structure of an exemplary TIE II antagonist is shown below as Structure XXI. TIE II inhibition of the free TIE II antagonist (Structure V) has a dissociation constant, $K_d$, about 8.8 nm and the TIE II inhibition of dendrimer conjugated TIE II antagonist (Structure XXI) has a dissociation constant, $K_d$, about 25 nm. Thus, in preferred embodiments, TIE II antagonists are conjugated to dendrimers with or without a spacer in such a way that it minimizes the reduction in TIE II inhibition, for example, less than 1-fold, 2-fold, 3-fold, 4-fold, 5-fold, 10-fold, 20-fold, 30-fold, 40-fold, 50-fold, and 100-fold. In preferred embodiments, the active agents are inhibitor of vascular endothelial growth factor receptor (VEGFR) and TIE II receptor tyrosine kinases.

Structure V: TIE II Antagonist 1

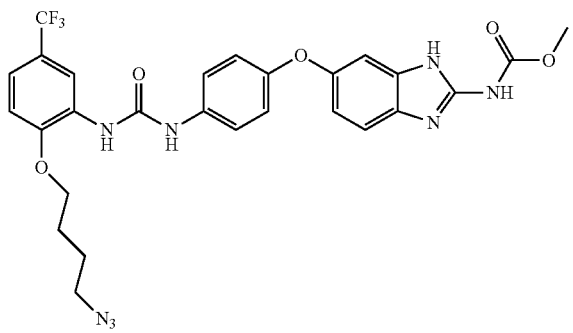 [SMILES: COC(=O)Nc1nc2ccc(Oc3ccc(NC(=O)Nc4cc(C(F)(F)F)ccc4OCCCCN=[N+]=[N-])cc3)cc2[nH]1]

Anti-Inflammatory Agents

In some embodiments, one or more active agents associated with or complexed to dendrimers are one or more anti-inflammatory agents. Anti-inflammatory agents reduce inflammation and include steroidal and non-steroidal drugs. Suitable steroidal active agents include glucocorticoids, progestins, mineralocorticoids, and corticosteroids. In some embodiments, one or more active agents are one or more corticosteroids.

Exemplary anti-inflammatory agents include triamcinolone acetonide, fluocinolone acetonide, methylprednisolone, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drugs (NSAIDs) include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone. In preferred embodiments, the active agent is triamcinolone acetonide, prednisolone, dexamethasone, or analogues thereof. Exemplary analogues of triamcinolone acetonide, prednisolone, and dexamethasone are shown below.

Structure VI a-f: Chemical Structure of Analogues of Triamcinolone Acetonide, Prednisolone, Dexamethasone a

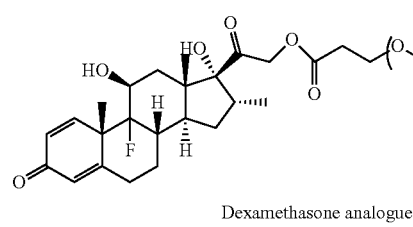

Dexamethasone analogue b

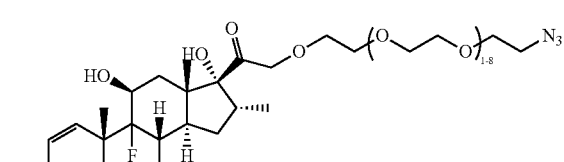

Dexamethasone analogue c

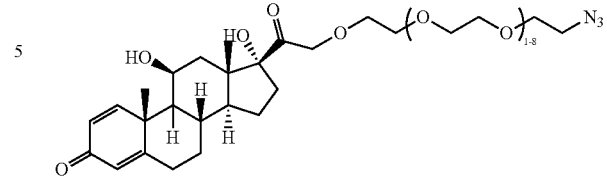

Prednisolone analogue d

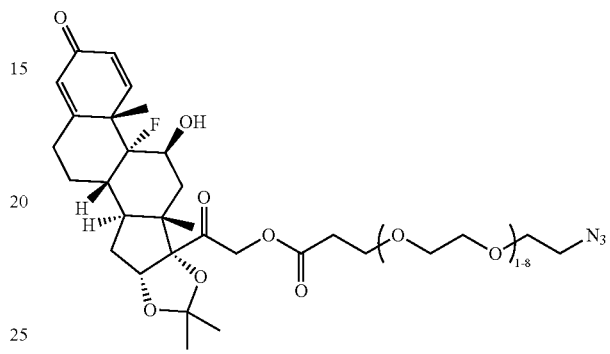

Triamcinolone acetonide analogue e

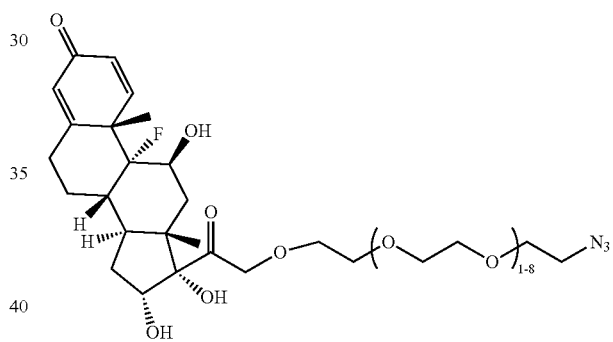

Triamcinolone acetonide analogue f

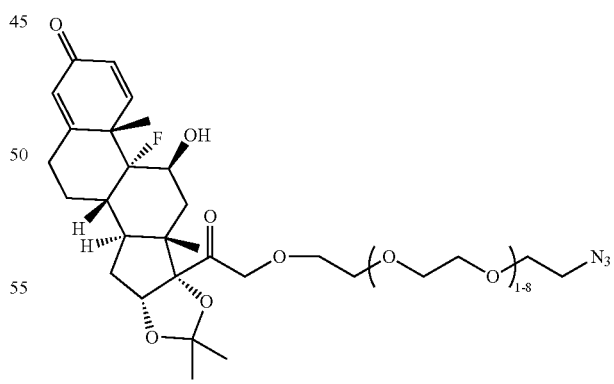

Triamcinolone acetonide analogue

Figure 14:
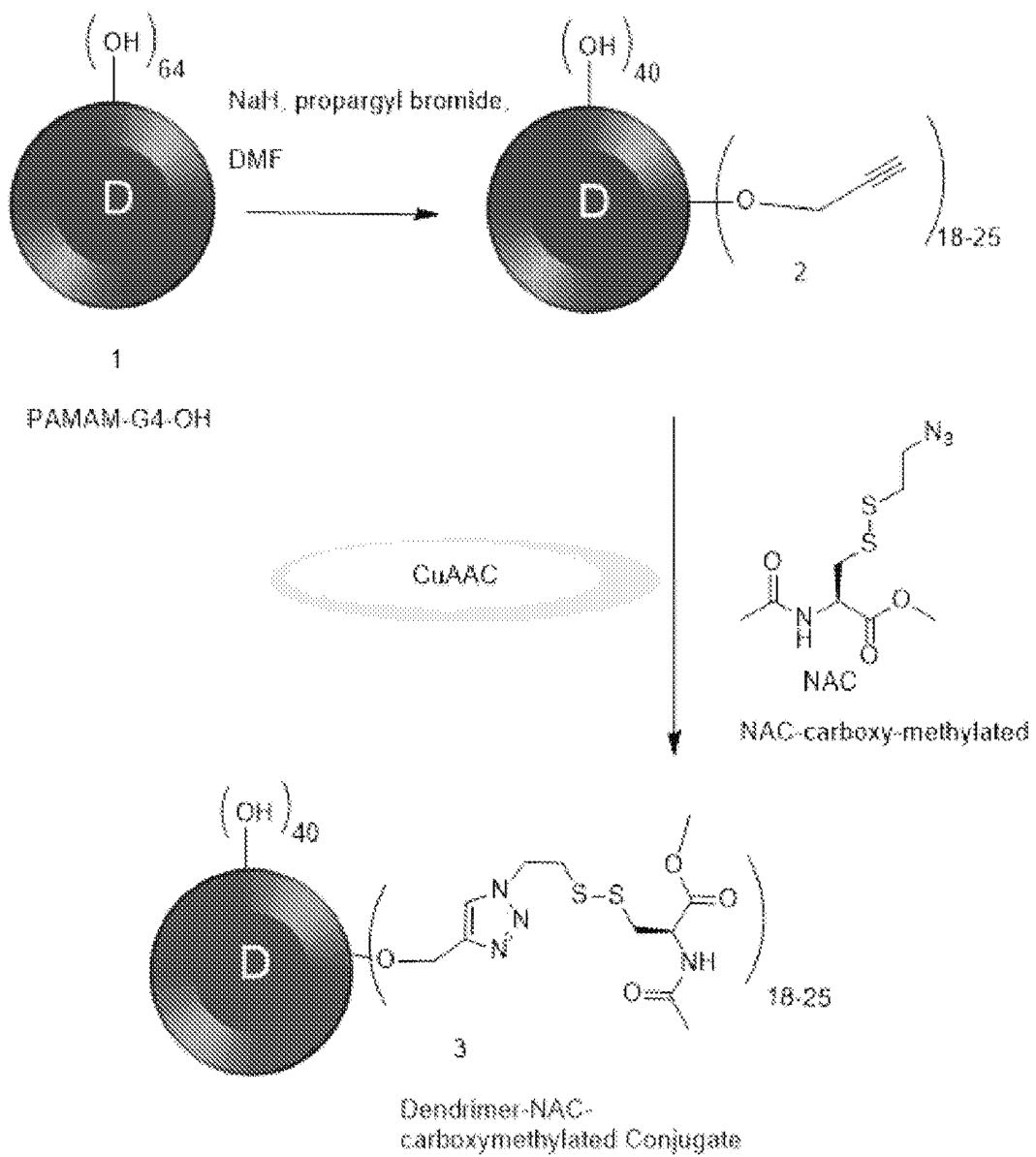
FIG. 14 is a synthesis scheme for Dendrimer-N-Acetyl-L-cysteine methyl ester conjugate (Dendrimer-NAC-carboxymethylated conjugate).

In some embodiments, the active agent is N-acetyl-L-cysteine, or a derivative or analogue or prodrug thereof. In a preferred embodiment, N-acetyl-L-cysteine is conjugated to a hydroxyl-terminated PAMAM dendrimer via non-cleavable linkage for minimal release of free N-acetyl-cysteine after in vivo administration. The synthesis route for an exemplary non-releasable (or non-cleavable) form of the dendrimer/N-acetyl-cysteine complexes is shown in FIG. 14. In one embodiment, the dendrimer complex is dendrimer-NAC-carboxymethylated conjugate as shown in FIG. 14. The non-releasable form of the dendrimer/N-acetyl-cysteine complex provides enhanced therapeutic efficacy as compared to a releasable or cleavable form of the dendrimer/N-acetyl-cysteine complex, for example, N-acetyl-L-cysteine conjugated to a hydroxyl-terminated PAMAM dendrimer via an ester linkage.

In some embodiments, one or more active agents are polysialic acid (e.g., low molecular weight polySia with an average degree of polymerization 20 (polySia avDP20)), Translocator Protein Ligands (e.g., Diazepam binding inhibitor (DBI)), Interferon-β (IFN-β), and minocycline.

In some cases, one or more active agents are anti-infective agents. Exemplary anti-infectious agents include antiviral agents, antibacterial agents, antiparasitic agents, and antifungal agents. Exemplary antibiotics include moxifloxacin, ciprofloxacin, erythromycin, levofloxacin, cefazolin, vancomycin, tigecycline, gentamycin, tobramycin, ceftazidime, ofloxacin, gatifloxacin; antifungals: amphotericin, voriconazole, natamycin.

Diagnostic Agents

Dendrimer nanoparticles can include diagnostic agents useful for determining the location of administered particles. These agents can also be used prophylactically. In some embodiments, dendrimers are conjugated to one or more diagnostic agents including indocyanine green, fluorescein (e.g., fluorescein isocyanate), boron-dipyrromethene, rhodamine, and rose Bengal. In preferred embodiments, the diagnostic agent is indocyanine green as shown below:

Structure VII: Chemical Structure of Indocyanine Green

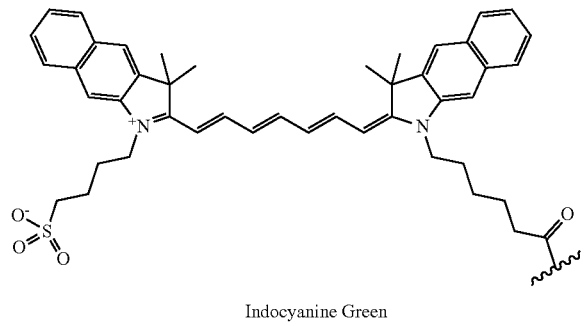 [SMILES: *C(=O)CCCCCN1/C(=C/C=C/C=C/C=C/C2=[N+](CCCCS(=O)(=O)[O-])c3cc4ccccc4cc3C2(C)C)C(C)(C)c2cc3ccccc3cc21]

Indocyanine Green

Additional examples of diagnostic agents include paramagnetic molecules, fluorescent compounds, magnetic molecules, and radionuclides, x-ray imaging agents, and contrast media. Examples of other suitable contrast agents include gases or gas emitting compounds, which are radioopaque. Dendrimer complexes can further include agents useful for determining the location of administered compositions. Agents useful for this purpose include fluorescent tags, radionuclides and contrast agents.

Exemplary diagnostic agents include dyes such as fluorescent dyes and near infra-red dyes, SPECT imaging agents, PET imaging agents and radioisotopes. Representative dyes include carbocyanine, indocarbocyanine, oxacarbocyanine, thüicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Exemplary SPECT or PET imaging agents include chelators such as diethylene tri-amine penta-acetic acid (DTPA), 1,4,7,10-tetra-azacyclododecane-1,4,7,10-tetraacetic acid (DOTA), di-amine dithiols, activated mercaptoacetyl-glycyl-glycyl-gylcine (MAG3), and hydrazidonicotinamide (HYNIC).

Exemplary isotopes include Tc-94m, Tc-99m, In-111, Ga-67, Ga-68, Gd3+, Y-86, Y-90, Lu-177, Re-186, Re-188, Cu-64, Cu-67, Co-55, Co-57, F-18, Sc-47, Ac-225, Bi-213, Bi-212, Pb-212, Sm-153, Ho-166, and Dy-166.

In preferred embodiments, the dendrimer complex includes one or more radioisotopes suitable for positron emission tomography (PET) imaging. Exemplary positron-emitting radioisotopes include carbon-11 ($^{11}$C), copper-64 ($^{64}$Cu), nitrogen-13 ($^{13}$N), oxygen-15 ($^{15}$O), gallium-68 ($^{68}$Ga), and fluorine-18 ($^{18}$F), e.g., 2-deoxy-2-$^{18}$F-fluoro-β-D-glucose ($^{18}$F-FDG).

In preferred embodiments, the one or more diagnostic agents can be functionalized with one or more spacers/linkers, for example with ether, ester, or amide linkage, for ease of conjugation with the dendrimers and/or for desired release kinetics.

In further embodiments, a singular dendrimer complex composition can simultaneously treat, and/or diagnose a disease or a condition at one or more locations in the body.

III. Pharmaceutical Formulations

Pharmaceutical compositions including one or more dendrimer complexes may be formulated in a conventional manner using one or more physiologically acceptable carriers including excipients and auxiliaries which facilitate processing of the active compounds into preparations which can be used pharmaceutically. Proper formulation is dependent upon the route of administration chosen. Pharmaceutical formulations contain one or more dendrimer complexes in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

In preferred embodiments, the compositions are formulated for parenteral delivery to the eye. In some embodiments, the compositions are formulated for subcutaneous or intravitreal injection. Typically the compositions will be formulated in sterile saline or buffered solution for injection into the tissues or cells to be treated. The compositions can be stored lyophilized in single use vials for rehydration immediately before use. Other means for rehydration and administration are known to those skilled in the art. Remington's Pharmaceutical Sciences, 20th ed., Lippincott Williams & Wilkins, Baltimore, MD, 2000, p. 704, provides suitable formulations and examples of ophthalmic drugs administered in the form of a pharmaceutically acceptable salt include timolol maleate, brimonidine tartrate, and sodium diclofenac.

The compositions are preferably formulated in dosage unit form for ease of administration and uniformity of dosage. The phrase "dosage unit form" refers to a physically discrete unit of conjugate appropriate for the patient to be treated. It will be understood, however, that the total single administration of the compositions will be decided by the attending physician within the scope of sound medical judgment. The therapeutically effective dose can be estimated initially either in cell culture assays or in animal models, usually mice, rabbits, dogs, or pigs. The animal model is also used to achieve a desirable concentration range and route of administration. Such information should then be useful to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

Pharmaceutical compositions formulated for administration by parenteral (intramuscular, intraperitoneal, intravenous or subcutaneous injection) and enteral routes of administration are described. In preferred embodiments, the compositions are administered via a systemic administration. In one embodiment, the compositions are administered via subcutaneous route. In another embodiment, the compositions are administered orally.

A. Parenteral Administration

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion. In some embodiments, the dendrimers are administered parenterally, for example, by subdural, intravenous, intrathecal, intraventricular, intraarterial, intra-amniotic, intraperitoneal, or subcutaneous routes. In preferred embodiments, the dendrimer compositions are administered via subcutaneous injection.

For liquid formulations, pharmaceutically acceptable carriers may be, for example, aqueous or non-aqueous solutions, suspensions, emulsions or oils. Parenteral vehicles include, for example, sodium chloride solution, Ringer's dextrose, dextrose and sodium chloride, lactated Ringer's and fixed oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media. The dendrimers can also be administered in an emulsion, for example, water in oil. Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Formulations suitable for parenteral administration can include antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous vehicles can include fluid and nutrient replenishers, electrolyte replenishers such as those based on Ringer's dextrose. In general, water, saline, aqueous dextrose and related sugar solutions, and glycols such as propylene glycols or polyethylene glycol are preferred liquid carriers, particularly for injectable solutions.

Injectable pharmaceutical carriers are well-known to those of ordinary skill in the art (see, e.g., Pharmaceutics and Pharmacy Practice, J. B. Lippincott Company, Philadelphia, PA, Banker and Chalmers, eds., pages 238-250 (1982), and ASHP Handbook on Injectable Drugs, Trissel, 15th ed., pages 622-630 (2009)).

B. Enteral Administration

In some embodiments, the compositions are formulated to be administered enterally. The carriers or diluents may be solid carriers such as capsule or tablets or diluents for solid formulations, liquid carriers or diluents for liquid formulations, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Vehicles include, for example, sodium chloride solution, Ringer's dextrose, dextrose and sodium chloride, lactated Ringer's and fixed oils. Formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Vehicles can include, for example, fluid and nutrient replenishers, electrolyte replenishers such as those based on Ringer's dextrose. In general, water, saline, aqueous dextrose and related sugar solutions are preferred liquid carriers. These can also be formulated with proteins, fats, saccharides and other components of infant formulas.

In preferred embodiments, the compositions are formulated for oral administration. Oral formulations may be in the form of chewing gum, gel strips, tablets, capsules or lozenges. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations.

IV. Methods of Making

A. Methods of Making Dendrimers

Dendrimers can be prepared via a variety of chemical reaction steps. Dendrimers are usually synthesized according to methods allowing controlling their structure at every stage of construction. The dendritic structures are mostly synthesized by two main different approaches: divergent or convergent.

In some embodiments, dendrimers are prepared using divergent methods, in which the dendrimer is assembled from a multifunctional core, which is extended outward by a series of reactions, commonly a Michael reaction. The strategy involves the coupling of monomeric molecules that possesses reactive and protective groups with the multifunctional core moiety which leads to stepwise addition of generations around the core followed by removal of protecting groups. For example, PAMAM-NH$_2$ dendrimers are first synthesized by coupling N-(2-aminoethyl) acryl amide monomers to an ammonia core.

In other embodiments, dendrimers are prepared using convergent methods, in which dendrimers are built from small molecules that end up at the surface of the sphere, and reactions proceed inward building inward and are eventually attached to a core.

Many other synthetic pathways exist for the preparation of dendrimers, such as the orthogonal approach, accelerated approaches the Double-stage convergent method or the hypercore approach, the hypermonomer method or the branched monomer approach, the Double exponential method; the Orthogonal coupling method or the two-step approach, the two monomers approach, AB$_2$—CD$_2$ approach.

In some embodiments, the core of the dendrimer, one or more branching units, one or more linkers/spacers, and/or one or more surface groups can be modified to allow conjugation to further functional groups (branching units, linkers/spacers, surface groups, etc.), monomers, and/or active agents via click chemistry, employing one or more Copper-Assisted Azide-Alkyne Cycloaddition (CuAAC), Diels-Alder reaction, thiol-ene and thiol-yne reactions, and azide-alkyne reactions (Arseneault M et al., Molecules. 2015 May 20; 20(5):9263-94). In some embodiments, premade dendrons are clicked onto high-density hydroxyl polymers. 'Click chemistry' involves, for example, the coupling of two different moieties (e.g., a core group and a branching unit; or a branching unit and a surface group) via a 1,3-dipolar cycloaddition reaction between an alkyne moiety (or equivalent thereof) on the surface of the first moiety and an azide moiety (e.g., present on a triazine composition) (or equivalent thereof) (or any active end group such as, for example, a primary amine end group, a hydroxyl end group, a carboxylic acid end group, a thiol end group, etc.) on the second moiety.

In some embodiments, dendrimer synthesis replies upon one or more reactions selected from thiol-ene click reactions, thiol-yne click reactions, CuAAC, Diels-Alder click reactions, azide-alkyne click reactions, Michael Addition, epoxy opening, esterification, silane chemistry, and a combination thereof.

Any existing dendritic platforms can be used to make dendrimers of desired functionalities, i.e., with a high-density of surface hydroxyl groups by conjugating high-hydroxyl containing moieties such as 1-thio-glycerol or pentaerythritol. Exemplary dendritic platforms such as polyamidoamine (PAMAM), poly (propylene imine) (PPI), poly-L-lysine, melamine, poly (etherhydroxylamine) (PE-HAM), poly (esteramine) (PEA) and polyglycerol can be synthesized and explored.

Still further, suitable dendrimers can be prepared by combining two or more dendrons. Dendrons are wedge-shaped sections of dendrimers with reactive focal point functional groups. Many dendron scaffolds are commercially available. They come in 1, 2, 3, 4, 5, and 6th generations with, respectively, 2, 4, 8, 16, 32, and 64 reactive groups. In certain examples, one type of active agents are linked to one type of dendron and a different type of active agents are linked to another type of dendron. The two dendrons are then connected to form a dendrimer. The two dendrons can be linked via click chemistry i.e., a 1,3-dipolar cycloaddition reaction between an azide moiety on one dendron and alkyne moiety on another to form a triazole linker.

Exemplary methods of making dendrimers are described in detail in International Patent Publication Nos. WO2009/046446, WO2015168347, WO2016025745, WO2016025741, WO2019094952, and U.S. Pat. No. 8,889,101.

B. Dendrimer Complexes

Dendrimer complexes can be formed of therapeutically active agents or compounds conjugated or attached to a dendrimer, a dendritic polymer or a hyperbranched polymer. Techniques for conjugation of one or more active agents to a dendrimer are known in the art, and are described in detail in U.S. Published Application Nos. US 2011/0034422, US 2012/0003155, and US 2013/0136697.

In some embodiments, one or more active agents are covalently attached to the dendrimers. In some embodiments, the active agents are attached to the dendrimer via a linking moiety that is designed to be cleaved in vivo. The linking moiety can be designed to be cleaved hydrolytically, enzymatically, or combinations thereof, so as to provide for the sustained release of the active agents in vivo. Both the composition of the linking moiety and its point of attachment to the active agent, are selected so that cleavage of the linking moiety releases either an active agent, or a suitable prodrug thereof. The composition of the linking moiety can also be selected in view of the desired release rate of the active agents.

In some embodiments, the attachment occurs via one or more of disulfide, ester, ether, thioester, carbamate, carbonate, hydrazine, or amide linkages. In preferred embodiments, the attachment occurs via an appropriate spacer that provides an ester bond or an amide bond between the agent and the dendrimer depending on the desired release kinetics of the active agent. In some cases, an ester bond is introduced for cleavable form of active agents. In other cases, an amide bond is introduced for non-cleavable form of active agents. Exemplary synthesis routes are described in Example 4 and 5 to show introduction of non-cleavable linkages between active agents and dendrimers.

Linking moieties generally include one or more organic functional groups. Examples of suitable organic functional groups include secondary amides (—CONH—), tertiary amides (—CONR—), sulfonamide (—S(O)$_2$—NR—), secondary carbamates (—OCONH—; —NHCOO—), tertiary carbamates (—OCONR—; —NRCOO—), carbonate (—O—C(O)—O—), ureas (—NHCONH—; —NR-CONH—; —NHCONR—, —NRCONR—), carbinols (—CHOH—, —CROH—), disulfide groups, hydrazones, hydrazides, ethers (—O—), and esters (—COO—, —CH$_2$O$_2$C—, CHRO$_2$C—), wherein R is an alkyl group, an aryl group, or a heterocyclic group. In general, the identity of the one or more organic functional groups within the linking moiety can be chosen in view of the desired release rate of the active agents. In addition, the one or more organic functional groups can be chosen to facilitate the covalent attachment of the active agents to the dendrimers. In preferred embodiments, the attachment can occur via an appropriate spacer that provides a disulfide bridge between the agent and the dendrimer. The dendrimer complexes are capable of rapid release of the agent in vivo by thiol exchange reactions, under the reduced conditions found in body.

In certain embodiments, the linking moiety includes one or more of the organic functional groups described above in combination with a spacer group. The spacer group can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms. Examples of suitable spacer groups include alkyl groups, heteroalkyl groups, alkylaryl groups, oligo- and polyethylene glycol chains, and oligo- and poly(amino acid) chains. Variation of the spacer group provides additional control over the release of the anti-inflammatory agents in vivo. In embodiments where the linking moiety includes a spacer group, one or more organic functional groups will generally be used to connect the spacer group to both the anti-inflammatory agent and the dendrimers.

Reactions and strategies useful for the covalent attachment of active agents to dendrimers are known in the art. See, for example, March, "Advanced Organic Chemistry," 5th Edition, 2001, Wiley-Interscience Publication, New York) and Hermanson, "Bioconjugate Techniques," 1996, Elsevier Academic Press, U.S.A. Appropriate methods for the covalent attachment of a given active agent can be selected in view of the linking moiety desired, as well as the structure of the active agents and dendrimers as a whole as it relates to compatibility of functional groups, protecting group strategies, and the presence of labile bonds.

The optimal drug loading will necessarily depend on many factors, including the choice of drug, dendrimer structure and size, and tissues to be treated. In some embodiments, the one or more active drugs are encapsulated, associated, and/or conjugated to the dendrimer at a concentration of about 0.01% to about 45%, preferably about 0.1% to about 30%, about 0.1% to about 20%, about 0.1% to about 10%, about 1% to about 10%, about 1% to about 5%, about 3% to about 20% by weight, and about 3% to about 10% by weight. However, optimal drug loading for any given drug, dendrimer, and site of target can be identified by routine methods, such as those described.

In some embodiments, conjugation of active agents and/or linkers occurs through one or more surface and/or interior groups. Thus, in some embodiments, the conjugation of active agents/linkers occurs via about 1%, 2%, 3%, 4%, or 5% of the total available surface functional groups, preferably hydroxyl groups, of the dendrimers prior to the conjugation. In other embodiments, the conjugation of active agents/linkers occurs on less than 5%, less than 10%, less than 15%, less than 20%, less than 25%, less than 30%, less than 35%, less than 40%, less than 45%, less than 50%, less than 55%, less than 60%, less than 65%, less than 70%, less than 75% total available surface functional groups of the dendrimers prior to the conjugation. In preferred embodiments, dendrimer complexes retain an effective amount of surface functional groups for targeting to specific cell types, whilst conjugated to an effective amount of active agents for treat, prevent, and/or image the disease or disorder.

1. Dendrimer Conjugation to Active Agents Via Ether Linkages

A method to incorporate one or more active agents onto a hydroxyl-terminated dendrimer via an ether linkage, optionally via one or more linkers/spacers, has been developed.

In some embodiments, surface or terminal groups of hydroxyl-terminated dendrimers are modified via etherification reaction prior to conjugation to one or more linkers/spacers and one or more radionuclides. Etherification is the dehydration of an alcohol to form ethers. In some embodiments, one or more hydroxyl groups of hydroxyl-terminated dendrimers undergo etherification reaction prior to conjugation to one or more linking moieties and one or more active agents.

In some embodiments, ether linkage is introduced at the surface groups of hydroxyl PAMAM dendrimer by reacting with propargyl bromide in the presence of 2% sodium hydroxide solution in DMSO. In a further embodiment, etherification reaction of generation 4 hydroxyl-terminated PAMAM dendrimer, PAMAM-G4-OH, using allyl bromide, anhydrous cesium carbonate and tetrabutylammonium iodide in DMF.

In other embodiments, at dendrimer generation 3.5, alkyne functional groups are introduced using a polyethyl glycol (PEG) linker with an amine at one end and a hexyne at the other end to produce a generation 4 bifunctional dendrimer, i.e., with hydroxyl groups and ether linkages ready for further conjugation. An exemplary bifunctional dendrimer is shown as compound 1 in FIG. 11 with 7 alkyne arms and 57 hydroxyl groups on the surface.

V. Methods of Use

The dendrimer complex compositions are generally suitable for treatment of one or more diseases or disorders associated with the eye, particularly inflammatory and/or angiogenic diseases in the eye. Dendrimer compositions and methods thereof for targeted delivery of one or more active agents to the diseased tissues/cells in the eye via systemic administration with increased efficacy and reduced side effects are described, preferably via selectively targeting to affected cells/tissue including activated microglia and activated macrophage, retinal pigment epithelia (RPE) cells, and/or choroidal neovascular (CNV) lesions. Preferably dendrimer compositions and methods thereof for targeted delivery give rise to minimal dendrimer in non-injured region of optic nerve or CNS. Methods for treating back of the eye disorders are also described. In some embodiments, the dendrimer complexes are used to treat exudative form of age-related macular degeneration (AMD). The methods typically include administering a subject in a need thereof an effective amount of a composition including dendrimer and one or more active agents.

Methods of reducing and/or inhibiting the number or activities of activated microglia and macrophages in the retina and/or the choroid in the eye of a subject in need thereof are provided. In some embodiments, treatment using an effective amount of the compositions including hydroxyl-terminated dendrimer complexed, covalently conjugated or intra-molecularly dispersed or encapsulated with one or more therapeutic agents is administered to reduce and/or inhibit the number or activities of the activated microglia and macrophages in the retina and/or the choroid in the eye in need thereof. In some embodiments, the compositions are administered in a dosage and via a route to inhibit or reduce activation of microglia in the retina. In other embodiments, compositions can inhibit or reduce phagocytic activities of microglia. In other embodiments, compositions including one or more receptor tyrosine kinase inhibitors can inhibit or reduce activity and/or quantity of activated microglia and macrophages in the diseased retina and/or choroid of a subject by about 10%, 20%, 30%, 40%, 50%, 75%, 85%, 90%, 95%, or 99% compared to the activity and/or quantity of the same cells in equivalent diseased tissues of subjects that did not receive, or were not treated with the dendrimer compositions (e.g., un-conjugated active agents).

Methods of reducing and/or inhibiting the expression and/or activities of VEGF and/or VEGFR in the activated microglia, activated macrophages, and/or retinal pigment epithelial (RPE) cells in the diseased retina and/or choroid are also described. In some embodiments, the compositions are applied via systemic routes such as intravenous injections, subcutaneous injections or oral administration. In preferred embodiments, the compositions are not administered intravitreally or subchoroidally, which can result in direct damage and/or inflammation to the eye. Methods of reducing and/or inhibiting one or more pro-inflammatory cytokines secreted by the activated microglia and macrophages in the diseased retina and/or choroid are also described. In some embodiments, treatment using an effective amount of the compositions leads to a decrease in expression of one or more pro-inflammatory cytokines (e.g., TNF-α, interleukin-1β (IL-1β), or interferon-γ (IFN-γ)) secreted by the activated microglia and macrophages in the diseased retina and/or choroid by about 10%, 20%, 30%, 40%, 50%, 75%, 85%, 90%, 95%, or 99% compared to those in equivalent diseased tissues of subjects that did not receive, or were not treated with the dendrimer compositions (e.g., un-conjugated active agents).

Methods of reducing and/or inhibiting one or more pro-oxidative properties of the activated microglia and macrophages in the diseased retina and/or choroid are also described. In some embodiments, treatment using an effective amount of the compositions leads to a decrease in the oxidative stress of the activated microglia and macrophages in the diseased retina and/or choroid, for example by reducing nitric oxide (NO) production or inducible nitric oxide synthase (iNOS) activation (e.g., NOS2 expression), by about 10%, 20%, 30%, 40%, 50%, 75%, 85%, 90%, 95%, or 99% compared to those in equivalent diseased tissues of subjects that did not receive, or were not treated with the dendrimer compositions (e.g., un-conjugated active agents).

Methods of reducing and/or inhibiting abnormal vascular permeability and leakage, and/or neoangiogenesis in the eye of a subject in need thereof are also described. In some embodiments, treatment using an effective amount of the compositions leads to a decrease in vascular leakage and/or neoangiogenesis.

A. Treatment Regimen

1. Dosage and Effective Amounts

Dosage and dosing regimens are dependent on the severity and location of the disorder or injury and/or methods of administration, and are known to those skilled in the art. A therapeutically effective amount of the dendrimer composition used in the treatment of one or more eye diseases is typically sufficient to treat, inhibit, or alleviate one or more symptoms associated with the eye.

In some in vivo approaches, the dendrimer complexes are administered to a subject in a therapeutically effective amount to reduce or inhibit ocular angiogenesis, particularly retinal and choroidal neovascularization. In some embodiments, an effective amount of the composition is used to reduce or inhibit endothelial cells angiogenesis and/or vascular endothelial cell proliferation.

A pharmaceutical composition including a therapeutically effective amount of the dendrimer compositions and a pharmaceutically acceptable diluent, carrier or excipient is described. In some embodiments, the pharmaceutical composition includes an effective amount of hydroxyl-terminated dendrimers conjugated to a VEGF receptor tyrosine kinase inhibitor. In some particular embodiments, dosage ranges suitable for parenteral use are between about 0.1 mg/kg and about 200 mg/kg, inclusive; between about 0.5 mg/kg and about 100 mg/kg, inclusive; between about 1.0 mg/kg and about 40 mg/kg, inclusive; and between about 2.0 mg/kg and about 20 mg/kg, inclusive. Higher doses may be given initially to load the patient with drug and maximize uptake in the diseased tissues (e.g. eye). After the loading dose, patients may receive a maintenance dose. Loading doses may range from 10 to 100 mg/kg of body weight and maintenance doses may range from 0.1 to <10 mg/kg of body weight. When administered enterally, the dose required for treatment may be up to 10 fold greater than the effective parenteral dose. The optimal dose is selected from the safety and efficacy results of each tested dose for each drug in patients.

Dosage forms of the pharmaceutical composition including the dendrimer compositions are also provided. "Dosage form" refers to the physical form of a dose of a therapeutic compound, such as a capsule or vial, intended to be administered to a patient. The term "dosage unit" as used herein refers to the amount of the therapeutic compounds to be administered to a patient in a single dose. In some embodiments, the dosage unit suitable for use are (assuming the weight of an average patient being 70 kg) between 5 mg/dosage unit and about 14,000 mg/dosage unit, inclusive; between about 35 mg/dosage unit and about 7,000 mg/dosage unit, inclusive; and between about 70 mg/dosage unit and about 2,800 mg/dosage unit, inclusive; and between about 140 mg/dosage unit and about 1,400 mg/dosage unit, inclusive.

The actual effective amounts of dendrimer complex can vary according to factors including the specific active agent administered, the particular composition formulated, the mode of administration, and the age, weight, condition of the subject being treated, as well as the route of administration and the disease or disorder.

Preferably the dendrimer compositions including one or more active agents, for example sunitinib, are delivered to cells in and around the diseases or injured tissues, (e.g. microglia). For example, dendrimer complex compositions can be in an amount effective to deliver one or more active agents to cells at or nearby the site of inflammation, particularly inflammation of the eye. Therefore, in some embodiments, the dendrimer complex compositions including one or more active agent are in an amount effective to ameliorate inflammation in a subject. In a preferred embodiment, the effective amount of dendrimer complex compositions does not induce significant cytotoxicity in the cells of a subject compared to an untreated control subject. Preferably, the amount of dendrimer complex compositions is effective to prevent or reduce inflammation and/or further associated symptoms of a disease or disorder in a subject compared to an untreated control.

In general, the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

In some embodiments, dosages are administered once, twice, or three times daily, or less frequently, for example, every other day, two days, three days, four days, five days, or six days to a human. In some embodiments, dosages are administered only about once or twice every week, every two weeks, every three weeks, or every four weeks. In some embodiments, dosages are administered about once or twice every month, every two months, every three months, every four months, every five months, or every six months, or less frequent. In a preferred embodiment, dosages are administered once every four weeks or less frequent.

It will be understood by those of ordinary skill that a dosing regimen can be any length of time sufficient to treat the disorder in the subject. In some embodiments, the regimen includes one or more cycles of a round of therapy followed by a drug holiday (e.g., no drug). The round of the therapy can be, for example, and of the administrations discussed above. Likewise, the drug holiday can be 1, 2, 3, 4, 5, 6, or 7 days; or 1, 2, 3, 4 weeks, or 1, 2, 3, 4, 5, or 6 months.

2. Controls

The therapeutic result of the dendrimer complex compositions including one or more active agents can be compared to a control. Suitable controls are known in the art and include, for example, untreated cells or an untreated subject. A typical control is a comparison of a condition or symptom of a subject prior to and after administration of the targeted agent. The condition or symptom can be a biochemical, molecular, physiological, or pathological readout. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art.

B. Subjects to be Treated

The compositions and methods are suitable for treatment one or more diseases or disorders of the eye. The compositions and methods are suitable for alleviating one or more symptoms associated with one or more diseases or disorder of the eye, for example, discomfort, pain, dryness, excessive tearing, injuries, infections, burns, and gradual loss of vision.

In some embodiments, the eye disorder to be treated is a back of the eye disease such as diabetic eye disease, symptomatic vitreomacular adhesion/vitreomacular traction (sVMA/VMT), and wet (neovascular) or dry AMD (age-related macular degeneration). In some embodiments, the eye disorder to be treated is one or more retinal and choroidal vascular diseases (e.g., AMD, retinopathy of prematurity, diabetic macular edema, retinal vein occlusion, retinopathy associated with toxicity of chemotherapy e.g., MEK retinopathy). In preferred embodiments, the eye disorder to be treated is age-related macular degeneration (AMD). Age-related macular degeneration (AMD) is a neurodegenerative, neuroinflammatory disease of the macula, which is responsible for central vision loss. The pathogenesis of age-related macular degeneration involves chronic neuroinflammation in the choroid (a blood vessel layer under the retina), the retinal pigment epithelium (RPE), a cell layer under the neurosensory retina, Bruch's membrane and the neurosensory retina, itself.

In other embodiments, the eye disorder to be treated is an inflammatory disease of the eye, i.e., diseases of the eye associated with inflammation of the tissues of the eye, including, for example, AMD, retinitis pigmentosa, optic neuritis, sarcoid, retinal detachment, temporal arteritis, retinal ischemia, arteriosclerotic retinopathy, hypertensive retinopathy, retinal artery blockage, retinal vein blockage, diabetic retinopathy, macular edema, Stargardt disease (also known as Stargardt macular dystrophy or juvenile macular degeneration), geographic atrophy, neuromyelitis optica, and also including angiogenic diseases including, for example, retinal neovascularization and choroidal neovascularization. Other conditions can also result in inflammation and/or angiogenesis in the eye, for example, infection, sickle cell disease, hypotension, etc.

Further examples of eye disorders that may be treated include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, meibomian gland dysfunction, anterior and posterior blepharitis, conjunctival hyperemia, conjunctival necrosis, cicatrical scaring and fibrosis, punctate epithelial keratopathy, filamentary keratitis, corneal erosions, thinning, ulcerations and perforations, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, inflammatory disease of the vitreous or retina, endophthalmitis prophylaxis and treatment, macular edema, macular degeneration, age-related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof. Other disorders include injury, burn, or abrasion of the cornea, cataracts and age related degeneration of the eye or vision associated therewith.

The dendrimer complexes can be administered in combination with one or more additional therapeutically active agents, which are known to be capable of treating conditions or diseases discussed above.

The present invention will be further understood by reference to the following non-limiting examples.

EXAMPLES

Example 1: Targeted Sustained Intracellular Delivery to Choroidal Neovascular Lesions after a Single Systemic Administration as Demonstrated by Imaging Methods Hydroxyl dendrimers (~14000 Da) were covalently conjugated to 2-3 indocyanine green (ICG) molecules (D-ICG) per dendrimer via non-cleavable linkages. Hydroxyl dendrimers (~14000 Da) were covalently conjugated to 2-3 tetramethylrhodamine (TRITC) molecules (D-TRITC) per dendrimer via non-cleavable linkages.

Two studies were conducted in C57BL/6 mice (n=5/group) administered intravenously 100 µL of D-ICG or vehicle control. In the first study, mice were administered D-ICG or vehicle control at 1, 3, 7, or 14 days post-laser and eyes were analyzed by optical coherence tomography (OCT) with ICG imaging at 4 or 24 hr post-dose. Flat-mounts of the sclera-choroid/retinal pigment epithelial (RPE) complexes were stained by fluorescently tagged isolectin and IBA-1.

The second study evaluated the localization and persistence of dendrimer conjugates in the CNV lesion. In the second study, mice were administered intravenously 100 µL of D-ICG and 100 µL of D-TRITC (1 hr after D-ICG) or vehicle control at 24 hr post-laser. Mice analyzed and sacrificed at 4, 7, 14, 21, and 28 days post-dose (n=5/group). For control group, free ICG (1.23 mg/mL), 100 µL, IV dosed 24 hr post-laser and mice analyzed and sacrificed at 2, 4, 7, and 14 days post-dose (n=5/group). Eyes analyzed by optical coherence tomography (OCT) with ICG imaging. Flat-mounts of the sclera-choroid/retinal pigment epithelial (RPE) complexes were stained by fluorescently tagged IBA-1 alone.

Results

No significant release of ICG or TRITC was observed from dendrimers under in vitro release when was evaluated at 37° C. in PBS, pH 7.4 or citrate buffer, pH 5.5 with esterase.

The ability of hydroxyl dendrimers labelled with indocyanine green (ICG) was evaluated to target choroidal neovascular (CNV) lesions, and further into macrophages and the retinal pigment epithelium, after systemic administration in a mouse model of laser-induced CNV.

Figure 2A:
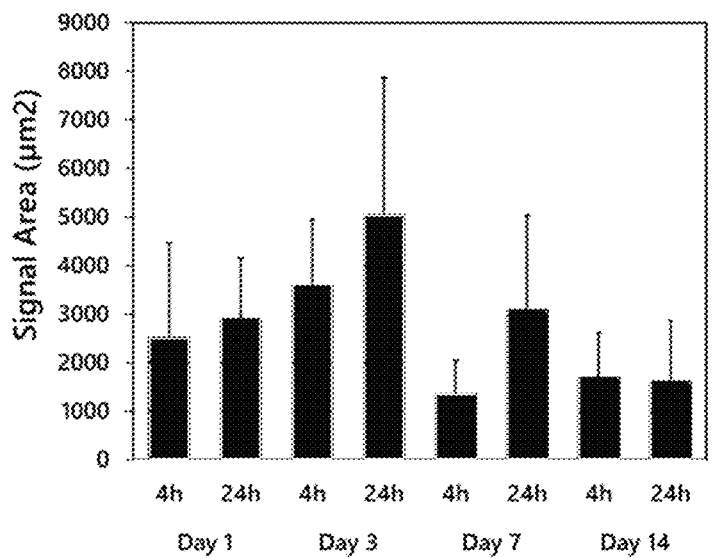
FIGS. 2A and 2B are bar graphs showing levels of isolectin (FIG. 2A), and IBA-1 (FIG. 2B), showing signal area ($\mu m^2$) for each of 4 hours (4 h) and 24 hours (24 h), at day 1, 3, 7 and 14 post-laser, respectively, as analyzed by optical coherence tomography with ICG imaging at 4 or 24 hr post-dose with D-ICG.
Figure 2B:
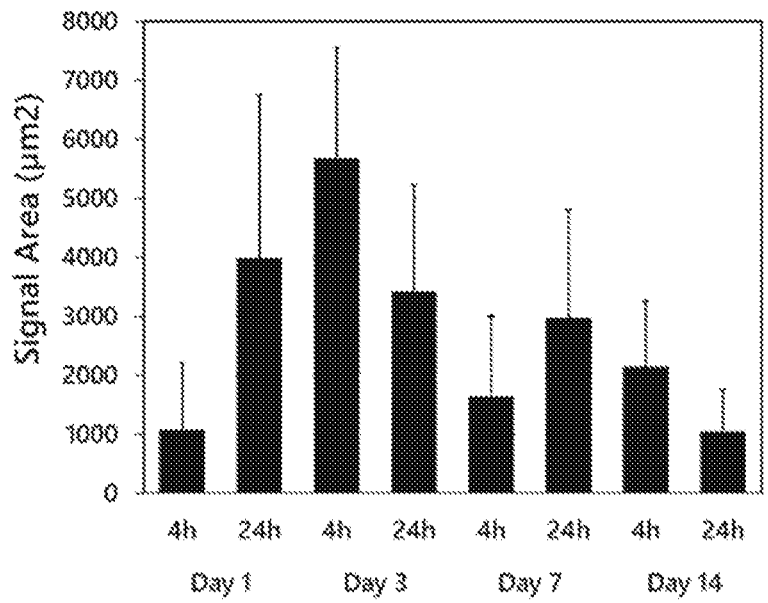
Figure 2C:
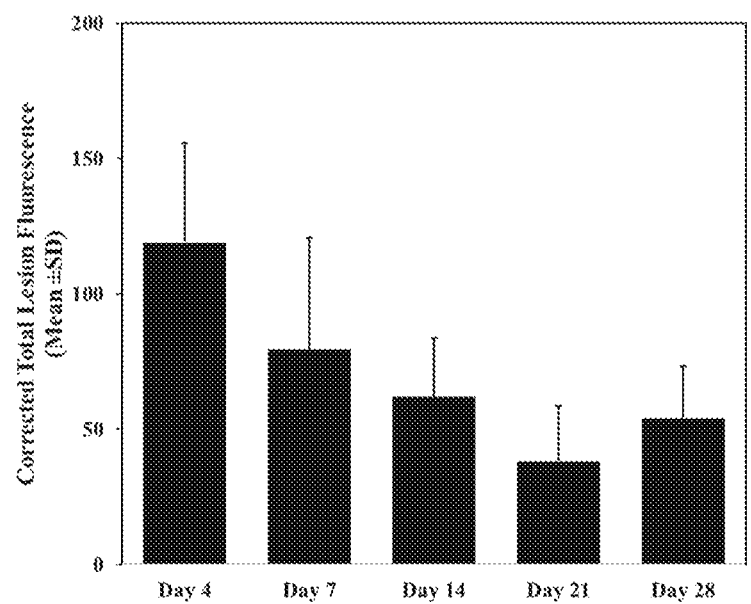
FIG. 2C is a bar graph showing corrected total lesion fluorescence over a period of 28 days after a single systemic dendrimer-indocyanine green (D-ICG) dose given 24 hr after laser injury localized to the choroidal neovascularization (CNV) lesion in C57BL/6 mice.

Systemically administered D-ICG was selectively taken up by cells within the CNV lesions within 24 hr after dosing, whereas the free ICG distributes non-specifically and is typically cleared within hours. Reactive macrophage and microglia endocytosed dendrimer conjugates 24 hr post-laser and lesion showed greater uptake during early stage of CNV, consistent with efficacy studies (24 hr post-laser). Dendrimer conjugates localized in macrophages in CNV lesions as shown by co-localization with IBA-1 positive cells (data not shown). Free ICG control groups showed that free ICG no longer present in the lesions between 7-14 days post-laser. IBA-1 signal increased up to 24-48 hr after laser injury and isolectin increases slightly later at the 48 h post-laser (FIGS. 1A and 2B). A single systemic D-ICG dose given 24 hr after laser injury localized to the CNV lesion and significant D-ICG was still present at the last time point, i.e., 28 days (FIG. 2C).

Hydroxyl dendrimers co-localized with reactive macrophages in choroids, microglia/macrophages in retina, and RPE cells at the site of inflammation/neovascularization. D-ICG and D-TRITC appeared to be intracellular and focused in regions of IBA-1 signal consistent with previous studies demonstrating hydroxyl dendrimer uptake in reactive microglia, macrophage, and RPE cells.

Hydroxyl dendrimers (D-ICG) selectively target to CNV lesions after systemic administration and persist for at least 28 days post-dose, despite the hydroxyl dendrimers are systemically cleared within 48 hr. Thus, the hydroxyl dendrimer provided a prolonged localization at the CNV lesions suitable for sustained and targeted therapies, for example, once per month systemic (subcutaneous or oral) treatment for retinal diseases with minimal systemic exposure.

Example 2: Suppression of Murine Choroidal Neovascularization after Systemic Administration of a Targeted Anti-VEGF Therapy Methods Hydroxyl dendrimers (~14000 Da), which selectively target inflammation, were covalently conjugated to analogs of sunitinib, an FDA-approved potent VEGF receptor tyrosine kinase inhibitor. Conjugates were made with a cleavable sunitinib analog (D-CSA, compound 6 in FIG. 1A) or a non-cleavable sunitinib analog (D-NSA, compound 3 in FIG. 1B) and drug release was evaluated at 37° C. in PBS, pH 7.4 or citrate buffer, pH 5.5 with esterase. Laser-induced rupture of Bruch's membrane was performed in both eyes of C57BL/6 mice (n=8/group) 24 hr prior to dose administration. Mice were administered intravenously (IV, 100 µL) vehicle, D-CSA (5.25 (low) or 26.25 (high) mg/kg sunitinib equivalent), D-NSA (6.3 (low) or 15.75 (high) mg/kg sunitinib equivalent), or free sunitinib (32.5 mg/kg). As a positive control group, a cohort of mice were administered aflibercept (EYLEA®) intravitreally (IVT; 1 µL, 40 µg). The CNV area was measured 7 days after laser treatment by both fluorescein angiography and flat-mounts of the sclera-choroid/RPE complexes stained with isolectin IB4.

Results

The efficacy of hydroxyl dendrimers covalently conjugated with analogs of sunitinib was evaluated in a mouse model of laser-induced choroidal neovascularization (CNV).

D-CSA was prepared with 5 sunitinib analogs per dendrimer (10.5% w/w) and D-NSA was prepared with 7 sunitinib analogs per dendrimer (12.6% w/w). Over 6 days in vitro, D-CSA released ~65% of the sunitinib at pH 5.5 with esterase (intracellular conditions) and ~15% release of sunitinib occurred over 24 hr at pH 7.4 (plasma conditions). Release of the sunitinib analog from D-NSA conjugate is minimal.

Figure 3:
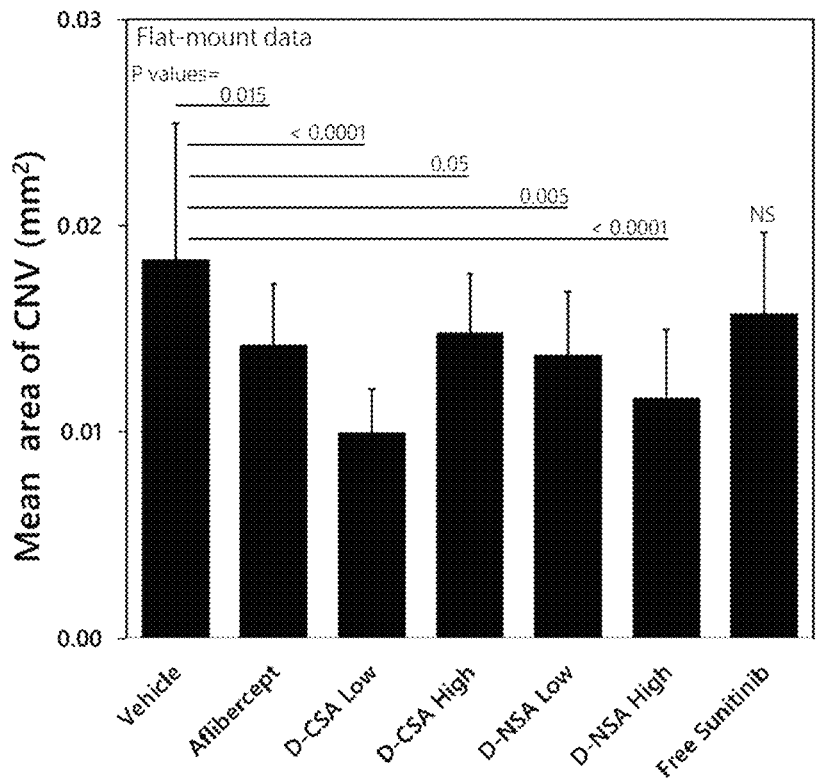
FIG. 3 is a bar graph showing mean area of choroidal neovascularization (CNV) ($mm^2$) in the eyes of mice treated with vehicle, aflibercept, a cleavable sunitinib analog (D-CSA) at a low dose (D-CSA low) or a high dose (D-CSA high), a non-cleavable sunitinib analog (D-NSA) at a low dose (D-NSA low) or a high dose (D-NSA high), and free sunitinib administered 24 hr after laser-induced rupture of Bruch's membrane in the eyes of C57BL/6 mice (n=8/group for all except D-NSA High where n=6). P values are indicated as compared to the vehicle control.

Statistically significant reductions in the CNV area were observed for IVT aflibercept and both IV dose levels of D-CSA and D-NSA but not free sunitinib (even at 5-fold higher doses compared to low dose D-CSA), compared with vehicle control (FIG. 3).

Binding affinity (Kd) to VEGFR2 was assessed with free sunitinib malate (0.13 nM), sunitinib analog attached via a non-cleavable PEG linker (1 nM) and D-NSA (27 nM). The binding affinity data indicated that high binding affinity was retained in D-NSA. Thus, it has been demonstrated that conjugation of a sunitinib analog to hydroxyl dendrimers maintains nanomolar potency for VEGF RTK.

Single doses of D-CSA/D-NSA administered in laser-induced CNV mouse model demonstrated efficacy comparable to aflibercept administered intravitreally. The non-cleavable sunitinib analog efficacy in CNV area reduction suggests that sunitinib release from the dendrimer may not be required. Previous studies have shown hydroxyl dendrimers and dendrimer-drug conjugates are retained in CNV lesions >28 days and systemically cleared intact within 24 hr in mice and humans without detectable liver or other off-target toxicity.

Example 3: Duration of Efficacy and Drug Systemic Clearance

Methods

Conjugates were made with a cleavable sunitinib analog (D-CSA, compound 6 in FIG. 1A) or a non-cleavable sunitinib analog (D-NSA, compound 3 in FIG. 1B). Laser-induced rupture of Bruch's membrane was performed in both eyes of C57BL/6 mice (n=8/group) 24 hr prior to dose administration. Mice were administered a single intraperitoneal injection (IP, 100 µL) vehicle, D-CSA (5.25 mg/kg sunitinib equivalent), D-NSA (6.3 mg/kg sunitinib equivalent), or free sunitinib (6.5 mg/kg). As a positive control group, a cohort of mice were administered aflibercept (EYLEA®) intravitreally (IVT; 1 µL, 40 µg). The CNV area was measured 7 days and 14 days after laser treatment by both fluorescein angiography and flat-mounts of the sclera-choroid/RPE complexes stained with isolectin IB4. For plasma pharmacokinetics study, the same dendrimer labeled with Cy5 administered via a single IP injection was monitored by plasma collection up to 72 hours after IP administration.

Results

The therapeutic duration and clearance of hydroxyl dendrimers covalently conjugated with analogs of sunitinib was evaluated in a mouse model of laser-induced choroidal neovascularization (CNV).

Figure 4A:
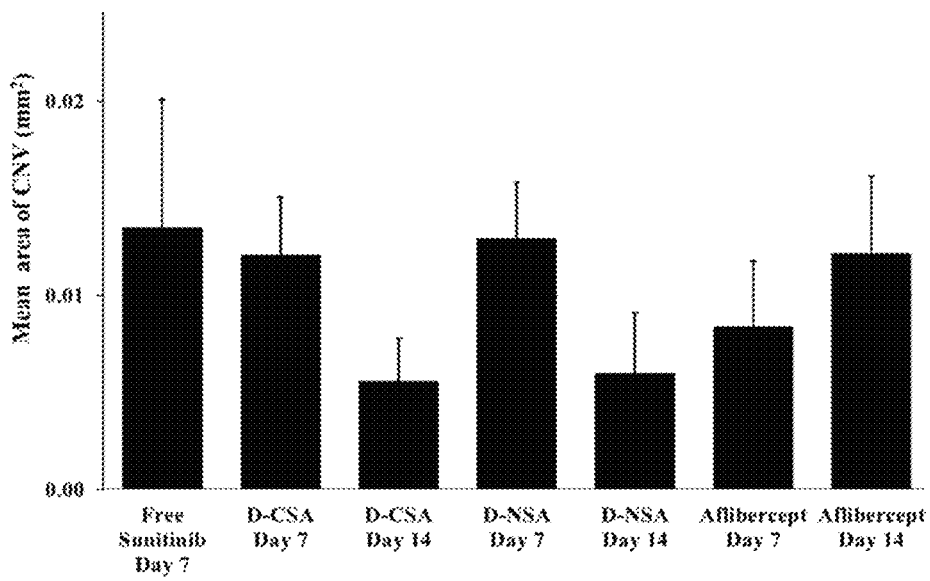
FIG. 4A is a bar graph showing mean area of choroidal neovascularization (CNV) ($mm^2$) in the eyes of mice treated with free sunitinib, a cleavable sunitinib analog (D-CSA), a non-cleavable sunitinib analog (D-NSA), and aflibercept administered 24 hr after laser-induced rupture of Bruch's membrane in the eyes of C57BL/6 mice (n=8/group) at day 7 and day 14 post-treatment, respectively.

Dendrimer conjugated sunitinib analog, D-CSA and D-NSA, demonstrated a durable response from a single IP dose with a reduction in the CNV area at day 7 post-treatment and a further reductions in the CNV area at day 14 post-treatment. Significant reduction in the CNV area was observed for IVT aflibercept at day 7 post-treatment but the reduction was not sustained at day 14 post-treatment (FIG. 4A).

Figure 4B:
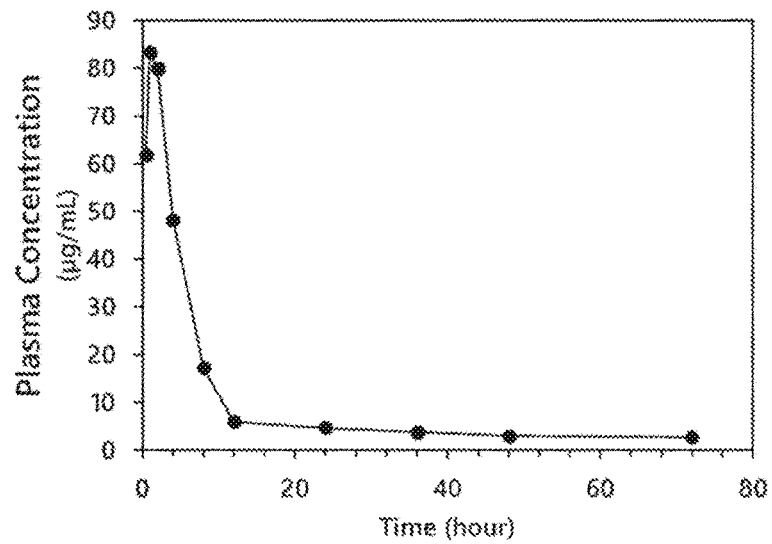
FIG. 4B is a line plot showing plasma concentration (µg/ml) of dendrimer sunitinib analog conjugates over time for a period of 0-72 hours.

In the serum, both D-CSA and D-NSA were cleared within 2 days post-treatment (FIG. 4B). Thus, the dendrimer conjugated sunitinib analog D-CSA and D-NSA provided a prolonged local effect on CNV lesions with the lesion size continued to decrease at day 14 post-treatment.

Figure 5:
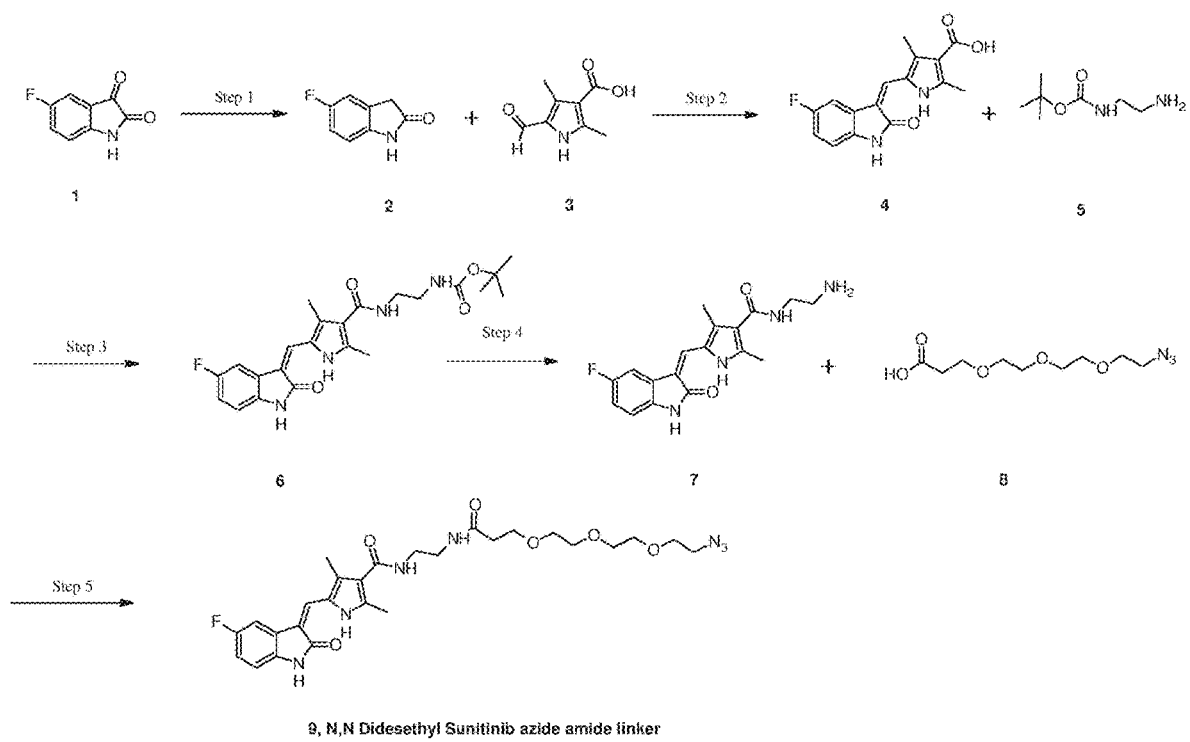
FIG. 5 is a reaction scheme showing one synthesis strategy of N,N-didesethyl sunitinib azide with an amide linkage.

Example 4: Synthesis and Characterization of N,N-Didesethyl Sunitinib Amide Azide The design and synthesis of dendrimer-didesethyl sunitinib conjugate is described in Examples 4 and 5. Overexpression of vascular endothelial growth factor (VEGF) has been implicated in a number of diseases associated with angiogenesis. Sunitinib is a receptor tyrosine kinase inhibitor that blocks VEGF receptors and has excellent antiangiogenic activity and is approved by the FDA for use in different types of cancers. Didesethyl sunitinib is an active metabolite of sunitinib. Despite the excellent therapeutic value of sunitinib and its analogues, their clinical development is hampered by the associated toxicity. The dendrimer-didesethyl sunitinib conjugates aim to overcome the dose related toxicities of sunitinib by attaching it to a hydroxyl terminated dendrimer. The synthesis scheme is outline in FIG. 5 and a generation 4 PAMAM is used as an exemplary hydroxyl terminated dendrimer.

Step 1: Synthesis of 5-fluoro-2,3-dihydro-1H-indol-2-one (Compound 2)

To a stirred solution of 5-fluoro-2,3-dihydro-1H-indole-2,3-dione (6.0 gm, 1.0 eq.) in n-butanol (10V) was added triethyl amine (6.12 mL, 1.2 eq.) and followed by hydrazine hydrate (3.56 mL, 2.0 eq.) was added at room temperature. The resulting solution was stirred for 16 hrs at 100° C. Reaction progress was monitored by TLC (50% ethylacetate in Hexanes). Once the reaction was judged to completion, reaction mass was as such evaporated to dryness under vacuum at 45° C. to obtain dark brown solid. The obtained solid was quenched with water (20 V) and extracted with ethyl acetate (30V) and organic layer was given water wash. Organic layer was concentrated to dryness on rotary evaporator. The crude product was purified by recrystallization using ethyl acetate to get grey color fluffy solid. (4.0 g, 72% yield.) The compound 2 shown in FIG. 5 was confirmed by $^1$H NMR, liquid chromatography, and mass spectrometry.

Step 2: Synthesis of 5-{[(3Z)-5-fluoro-2-oxo-2,3-dihydro-1H-indol-3-ylidene]methyl}-2,4-dimethyl-1H-pyrrole-3-carboxylic acid (Compound 4)

To a stirred solution of 5-fluoro-2,3-dihydro-1H-indol-2-one (compound 2) (4.0 gm, 1.0 eq.) and 5-formyl-2,4-dimethyl-1H-pyrrole-3-carboxylic acid (compound 3) (4.41 gm, 1.0 eq.) in ethanol (10V) was added pyrrolidine (4.42 mL, 2.0 eq.) at room temperature. The resulting solution was stirred for 3 hrs at 80° C. Reaction progress was monitored by TLC (10% Methanol in DCM). Once the reaction was judged to completion, reaction mass was cooled to room temperature added 2M HCl solution to pH=3. A brownish-red precipitate was formed and filtered. The obtained solid was washed with ethanol (20 V) followed by hexanes (30 V) and filtered to get reddish-orange solid. (6.6 g, 82% yield.) The compound 4 shown in FIG. 5 was confirmed by $^1$H NMR.

Step 3: Synthesis of tert-butyl N-{2-[(5-{[(3Z)-5-fluoro-2-oxo-2,3-dihydro-1H-indol-3-ylidene]methyl}-2,4-dimethyl-1H-pyrrol-3-yl)formamido]ethyl}carbamate (Compound 6)

To a solution of 5-{[(3Z)-5-fluoro-2-oxo-2,3-dihydro-1H-indol-3-ylidene]methyl}-2,4-dimethyl-1H-pyrrole-3-carboxylic acid (compound 4) (6.5 g, 1.0 eq.) in DMF were added triethyl amine (6.08 mL, 2.0 eq.) EDC·HCl ((8.68 g, 2.1 eq.), HOBT (3.94 g, 1.35 eq.) and tert-butyl N-(2-aminoethyl) carbamate (4.16 g, 1.2 eq.) and at 0° C. Reaction was stirred at room temperature for 16 hrs. Reaction mixture was diluted with water (20.0 V), stirred for 10 min. to precipitate and filtered to get brown solid. The obtained solid was washed with ethyl acetate (15.0 V), followed by hexanes (15.0V), filtered and dried to get brownish-orange solid as a tert-butyl N-{2-[(5-{[(3Z)-5-fluoro-2-oxo-2,3-dihydro-1H-indol-3-ylidene]methyl}-2,4-dimethyl-1H-pyrrol-3-yl)formamido]ethyl}carbamate (compound 6) (7.5 g, 78% yield). The compound 6 shown in FIG. 5 was confirmed by $^1$H NMR.

Step 4: Synthesis of N-(2-aminoethyl)-5-{[(3Z)-5-fluoro-2-oxo-2,3-dihydro-1H-indol-3-ylidene]methyl}-2,4-dimethyl-1H-pyrrole-3-carboxamide (Compound 7)

To a solution of tert-butyl N-{2-[(5-{[(3Z)-5-fluoro-2-oxo-2,3-dihydro-1H-indol-3-ylidene]methyl}-2,4-dimethyl-1H-pyrrol-3-yl)formamido]ethyl}carbamate (compound 6) (9.0 g, 1.0 eq.) in DCM (10.0 V) was added trifluoro acetic acid (3.0 V) at 0-5° C. Reaction was stirred at room temperature for 12 hrs. Reaction mass was as such evaporated to dryness under vacuum at 45° C. to obtain dark brown solid. The obtained solid was washed with diethyl ether (15.0 V) filtered and dried to get orange-yellow solid (6.0 g crude). The compound 7 shown in FIG. 5 was confirmed by $^1$H NMR, liquid chromatography, and mass spectrometry.

Step 5: Synthesis of N-{2-[(5-{[(3Z)-5-fluoro-2-oxo-2,3-dihydro-1H-indol-3-ylidene]methyl}-2,4-dimethyl-1H-pyrrol-3-yl)formamido]ethyl}-3-[2-(2-propoxyethoxy)ethoxy]propanamide (Compound 9)

To a solution of 3-[2-(2-propoxyethoxy)ethoxy]propanoic acid (8) (5.95 g, 1.0 eq.) in DMF (10.0 V) were added DIPEA (8.40 mL, 2.0 eq.) EDC·HCl (6.90 g, 1.5 eq.), HOBT (0.65 g, 0.2 eq.), N-(2-aminoethyl)-5-{[(3Z)-5-fluoro-2-oxo-2,3-dihydro-1H-indol-3-ylidene]methyl}-2,4-dimethyl-1H-pyrrole-3-carboxamide (compound 7) (11.0 g, 1.0 eq.) and DMAP (0.294 g, 0.1 eq.) at 0-5° C. Reaction was stirred at room temperature for 3 hrs. Reaction progress was monitored by TLC (10% MeOH in DCM). Reaction mixture was diluted with water (20.0 V) stirred for 10 min. to form brown precipitate and filtered. The obtained solid purified by reverse phase column chromatography to obtain N,N-didesethyl sunitinib amide azide as an orange solid (5.2 g, 37% yield). The compound 9 was confirmed by $^1$H NMR, liquid chromatography, and mass spectrometry.

Example 5: Synthesis and Characterization of Dendrimer-Didesethyl Sunitinib Conjugate (D-4517)

Methods
Synthesis and Characterization of Intermediates and Dendrimer Conjugate:
Synthesis of Dendrimer Hexyne (Compound 2 of FIG. 6A):

Took a dried round bottom flask (250 mL) and recorded its empty weight. Poured the desired amount of the methanolic solution of G4-OH in the round bottom and evaporated at 60° C. for 2 hours. Shifted the flask on the high vacuum assembly for 1 hour. Recorded the amount of G4-OH in the flask. Once the weight of G4-OH was recorded, added 50-60 mL of anhydrous DMF to the flask and evaporated under reduced pressure to remove any trace of methanol present in the dendrimer which could impact the efficiency of Steglich esterification. After the evaporation of DMF, the flask was brought under nitrogen environment. Added anhydrous DMF (10 mL/gram) to the flask and shifted the solution on sonication bath and sonicated the reaction mixture until clear solution was achieved. 5-Hexynoic acid was dissolved in 2 ml of DMF and added to the stirring solution. After 10 minutes, EDC·HCl and DMAP were added to the stirring solution and the solution was left on stirring at room temperature for 48 hours. On completion, DMF dialysis was started in 1 kDa molecular weight cut-off dialysis bag. DMF dialysis was performed for 8 h, replacing DMF once. After 8 h, 30 mL of D.I. water was added to the solution in the bag and was dialysed against water for overnight. The reaction mixture was diluted with HPLC water and the final volume was made 300-350 mL. TFF was performed in D.I water using 3 kDa TFF cartridge. The TFF cycle was performed 6-7 times and the final retentate volume was around 100 mL which was lyophilized to obtained sticky solid. The product yield was around 5.5 g (74%). The $^1$H NMR was recorded at 500 MHz instrument in deuterated DMSO where ~10 mg of compound was used for sample preparation. The loading of hexynoic acid was calculated by proton integration method. The internal amide peak of dendrimer between δ8.11-7.70 ppm was the reference peak. The peak at δ4.0 ppm corresponding to ester linked protons and peak at δ1.6 ppm is the CH$_2$ from hexynoic acid. Proton integration method suggested the attachment of 9-10 molecules of hexynoic acid per dendrimer. The HPLC purity was >99%.

TABLE 1

Figure 6A:
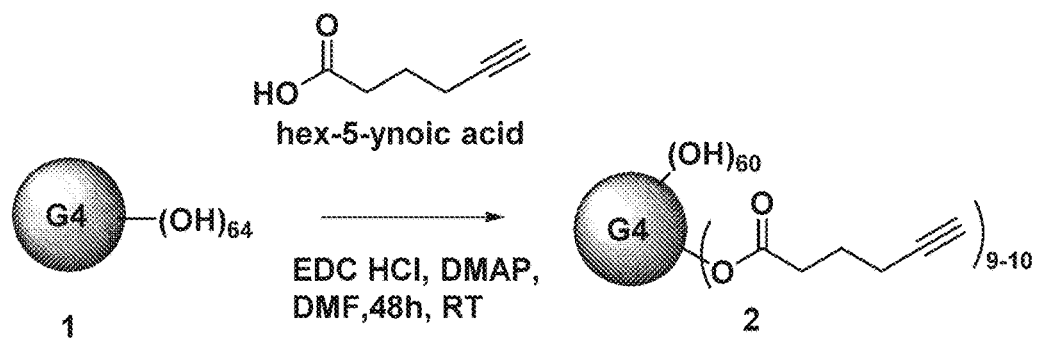
FIGS. 6A and 6B are schemes showing chemical reaction steps for the synthesis of an exemplary dendrimer-sunitinib conjugate via first synthesizing dendrimer-hexynoic-acid conjugate (FIG. 6A), prior to the step of synthesizing dendrimer-didesethyl-sunitinib amide-conjugate (FIG. 6B). G4 PAMAM dendrimer is used as an exemplary dendrimer.

Reagents for Synthesis of dendrimer hexyne (Compound 2 of FIG. 6A)

|  | G4-OH | 5-Hexynoic acid | EDC•HCl | DMAP |
|---|---|---|---|---|
| M.W | 14279 | 112.13 | 191.7 | 122.17 |
| Amount | 10.5 g | 1.15 g | 3.52 g | 1.79 g |
| Millimoles: | 0.73 | 10.3 | 18.4 | 14.7 |
| Equivalents | 1 | 14 | 25 | 20 |

Synthesis of Dendrimer-Didesethyl Sunitinib Conjugate (Compound 3 in FIG. 6B):

Placed dendrimer hexyne (compound 2 of FIG. 6A) in the 250 mL round bottom flask. Dissolved the compound in 40 mL anhydrous DMF by sonication. The sunitinib-azide solution was added in the reaction mixture by dissolving it in 20 mL DMF and solution was stirred. It was followed by the addition of 10 mL of water to the reaction mixture to stop the precipitation of copper salt in reaction mixture. After 10 minutes of stirring, copper sulfate pentahydrate (dissolved in 3 mL of water) was added dropwise to the reaction flask. The stirring solution turned blue in color. After 5 minutes, sodium ascorbate (dissolved in 3 mL of water) was added dropwise to the reaction mixture and the reaction vial was shifted over oil bath which was set at 40° C. The reaction mixture was stirred and heated for 24 h. On completion, the DMF was evaporated and the reaction mixture was diluted with 300 mL of 10% DMAc in water. To this solution, EDTA (500 microliter, 0.5M) solution was added for copper salt removal by chelation. TFF was performed on the reaction mixture in water using 3 kDa TFF cartridge. 8-10 Diavolumes were performed in 10% DMAc in water, followed by 5-6 cycles in water as buffer to remove the solvent traces. The final retentate volume was around 150 mL which was lyophilized to obtain off yellow solid. The product yield was 5.5 g. The $^1$H NMR was recorded at 500 MHz instrument in deuterated DMSO and deuterated water and around 10 mg of compound was used for sample preparation. 100 scans were made for the $^1$H NMR. The $^1$H NMR indicated the formation of product and 6-7 arms of sunitinib molecule were attached (FIG. 4). The drug loading is calculated by proton integration method where peaks corresponding to dendrimer and drug are compared. The CH$_2$ peak at 1.8 ppm corresponding to hexynoic acid and ester linked CH$_2$ at 4.0 ppm is locked as the reference peak from dendrimer side. After the triazole formation, the new peak in $^1$H NMR corresponding to CH$_2$ peak protons next to triazole ring at δ 4.4 ppm, 2 aromatic protons from sunitinib in between 6.92-6.80 ppm and 2 NH protons at 10.9 and 13.6 ppm were used to calculate the loading of drug molecules. After the click reaction, there is formation of 1-4 triazole and the signature proton peak corresponding to triazole appears in between δ 7.5-8.0 ppm which is suppressed by the presence of internal amide protons. For confirmation of sunitinib attachment, the $^1$H NMR was recorded in D$_2$O where the disappearance of internal amide peaks and presence of triazole peak at δ 7.7 ppm were observed. The HPLC purity was >99%.

TABLE 2

Reagents for Synthesis of Dendrimer-didesethyl Sunitinib Conjugate (D-4517)

|  | Compound 2 | Desethyl sunitinib-azide | CuSO$_4$•5H$_2$O | Na ascorbate |
|---|---|---|---|---|
| M.W | ~15000 | 571.6 | 249.69 | 168 mg |
| Amount | 5.1 g | 1.65 g | 170 mg | 250 mg |
| Millimoles: | 0.340 | 2.89 | 0.68 | 0.85 |
| Equivalents | 1 | 8.5 | 2 | 2.5 |

Protocol for the In Vitro Kinase Binding Assay

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK® (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SEABLOCK®, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1× PBS, 0.05% Tween 20). The beads were then re-suspended in elution buffer (1× PBS, 0.05% Tween 20, 0.5 μM non-biotinylated affinity ligand) and incubated at room temperature with shaking for 30 minutes. The kinase concentration in the eluates was measured by qPCR.

Sample Preparation:

Sunitinib malate, sunitinib ester amide linker and D4-sunitinib conjugate were dissolved in aqueous DMSO to form solution at free drug (sunitinib) concentration of 10 mM. Each sample solution was further diluted to 10 μM, 3.33 μM, 1.11 μM, 0.37 μM, 0.123 μM, 41.2 nM, 13.7 nM, 4.57 nM, 1.52 nM, 0.508 nM and 0.169 nM in DMSO respectively.

Results

Figure 6B:
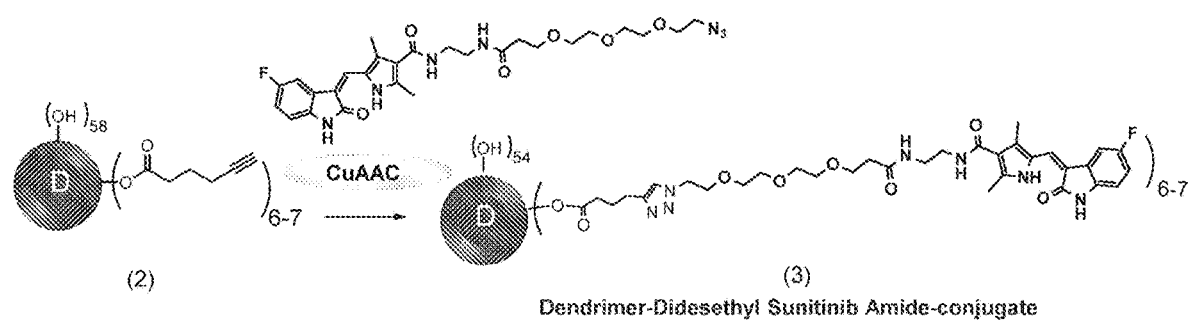

Synthesis and Characterization:

The synthesis of dendrimer-didesethyl sunitinib analogue is achieved in 3 steps via copper(I) catalysed alkyne-azide click reaction (FIGS. 6A and 6B). The first step involves the partial modification of the dendrimer surface hydroxyl groups by attaching a few hexynoic acid linker arms by esterification to bring alkyne surface groups. Second step is the introduction of a linker arm on the didesethyl sunitinib with azide terminal. Third step involves the click reaction of both parts. For the synthesis of dendrimer hexynoic acid, the as-received ethylenediamine core hydroxyl polyamidoamine dendrimer (G4-OH, Pharma grade>95% HPLC purity) was used. Partial esterification of the OH terminated dendrimer (compound 1) was first performed (FIG. 6A) with 5-hexynoic acid using the EDC·HCl and DMAP in anhydrous N,N-dimethylformamide to yield compound 2. $^1$H NMR was used for the confirmation of the compound. The loading of the hexyne linker was calculated by proton integration method by comparing the linker protons to the internal amide protons of the dendrimer between δ8.11-7.70 ppm. The peak at δ4.0 ppm corresponding to ester linked protons and peak at δ1.6 ppm refers the $CH_2$ from hexynoic acid. Proton integration method suggested the attachment of 8-10 molecules of alkyne linker per dendrimer. The purity of the construct was evaluated using HPLC and it was found to be >99%. Linker 3-[2-(2-propoxyethoxy)ethoxy]propanoic acid was attached to didesethyl sunitinib using EDC·HCl, DMAP, DIPEA, HOBt in anhydrous DMF to bring azide to participate in click reaction. The drug is connected through the linker with an amide linkage. The dendrimer hexyne (2) and didesethyl sunitinib PEG azide were used for performing click reaction. Copper catalysed click reaction is one of the most efficient chemical transformation which has brought revolution in the field of drug discovery and is an excellent tool for conjugation of small or big molecules to macromolecules, polymers and antibodies. It is known for its easy execution, milder reaction conditions, compatibility with different functional groups, regio-selective, enhanced reaction rates, produce cleaner products with great yields. Copper (II) sulphate pentahydrate and sodium ascorbate were used for the click reaction in the presence of DMF:$H_2O$ (1:1). The reaction was carried out at room temperature for overnight followed by the purification by tangential flow filtration. The formation of product (3) was confirmed by $^1$H NMR. The $^1$H NMR spectrum of the conjugate clearly shows the peaks corresponding to the dendrimer, drug and linkers attached to it, and the drug loading was calculated by comparing these peaks with the help of proton integration method. The internal amide protons from the dendrimer are present in between δ 8.5-7.5 ppm when spectrum is recorded in deuterated DMSO. These amide peaks are a reference standard for the rest of the peaks. The —NH peaks from drug appear at δ 13.6 and 10.8 ppm. There are 4 protons from the drug and one triazole proton which is formed after the click reaction merged with internal amide peaks and comes in between δ 8.5-7.5 ppm. Additionally, two aromatic protons from sunitinib situated next to the fluorine group appear at δ 6.95-6.85 ppm. A sharp triazole peak at δ 7.7 ppm which is a signature peak for the click transformation is observed when the NMR solvent is switched from deuterated DMSO to $CD_3OD$. After the click, the $CH_2$ present next to the azide downshielded and can be observed at δ 4.4 ppm. The comparison of proton NMR spectra of drug linker, dendrimer intermediate and the final conjugate was confirmed by $^1$H NMR. The purity of the dendrimer drug conjugate, intermediate and drug linker was evaluated using HPLC. The final conjugate is >99% pure by HPLC. The dendrimer G4-OH and dendrimer hexyne intermediate is visible at 210 nm channel and the didesethyl sunitinib is visible at 430 nm in HPLC. The retention time of the compound 2 is around 16.9 minutes but once the hydrophobic drug molecules are attached to the dendrimer, the peak of the final conjugate shifts towards the right and comes around 27 minutes which confirms the attachment of hydrophobic drugs to the dendrimer construct. Once the drug is attached to dendrimer the peak corresponding to it at both 210 nm (dendrimer absorption wavelength) and 430 nm (drug absorption wavelength) channels was observed, which further confirms the formation of product. The drug loading of the dendrimer conjugate is around 12.6% wt/wt which corresponds to 7 molecules of drug attached per dendrimer molecule.

Binding Affinity:

The kinase comparative binding affinity of D-didesethyl-Sunitinib-conjugate (Compound D-4517), free sunitinib malate and sunitinib linker (AVT-4517) was evaluated, and the results are presented in Table 3. The binding affinity for free sunitinib is 0.13 nM. After the attachment of PEG linker, the binding affinity decreased around 8 folds to 1.0 nM. The conjugate exhibited the binding affinity of 27 nM. The results demonstrate that the conjugation of drug on the dendrimer surface retains the binding affinity of the drug to RTK domain in nanomolar range. This shows that the conjugate itself is active and can bind to the receptor without the release of the drug. It has been shown for the first time that conjugation of a small molecule inhibitor (300-400 Da) to a large dendrimer (14000 Da) can still retain nanomolar binding of the small molecule inhibitor.

TABLE 3

D-didesethyl-Sunitinib-conjugate Kinase (VGEFR2) binding assay study:

| Compounds | Structure | Gene Symbol | Kd (nM) |
|---|---|---|---|
| Sunitinib Malate | 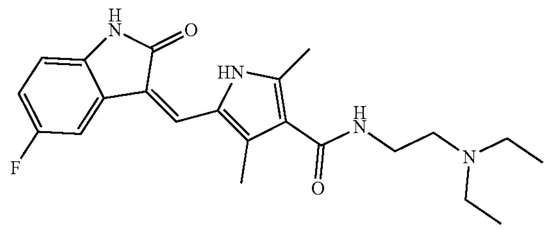 [SMILES: CCN(CC)CCNC(=O)c1c(C)[nH]c(/C=C2\C(=O)Nc3ccc(F)cc32)c1C] | VEGFR2 | 0.13 |
| Sunitinib ester amide linker (AVT-4517) | 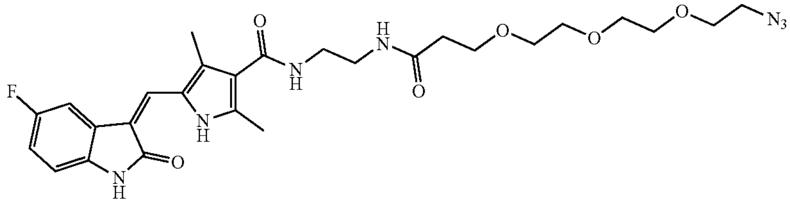 [SMILES: Cc1[nH]c(/C=C2\C(=O)Nc3ccc(F)cc32)c(C)c1C(=O)NCCNC(=O)CCOCCOCCOCCN=[N+]=[N-]] | VEGFR2 | 1.0 |
| D-didesethyl-Sunitinib-conjugate (D-4517) | 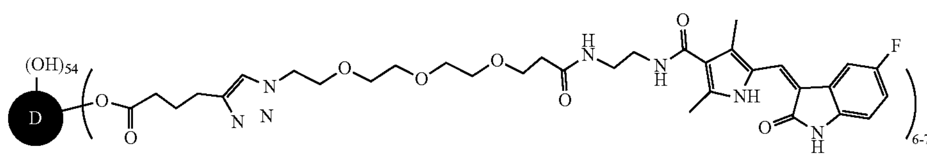 | VEGFR2 | 27 |

Stability Studies in Human and Rat Plasma:

In vitro stability of D-didesethyl sunitinib (D-4517) in human and rat plasma was further evaluated at physiological conditions. The results presented in Table 4 suggest that the conjugate D4517 is very stable with 2% (weight percentage) release in human plasma, and 4% (weight percentage) release in rat plasma) after 48 h.

TABLE 4

In vitro stability study of drug release percentage of D-didesethyl sunitinib (D-4517) by weight in human and rat plasma at 37° C.

| Time point (hours) | Release percentage in human plasma (%) | Release percentage in rat plasma (%) |
|---|---|---|
| 0.5 | 0.13 | 0.15 |
| 1 | 0.12 | 0.17 |
| 2 | 0.16 | 0.31 |
| 4 | 0.2 | 0.59 |
| 6 | 0.28 | 0.81 |
| 8 | 0.54 | 1.42 |
| 24 | 0.76 | 1.97 |
| 48 | 2.01 | 3.98 |

Figure 7:
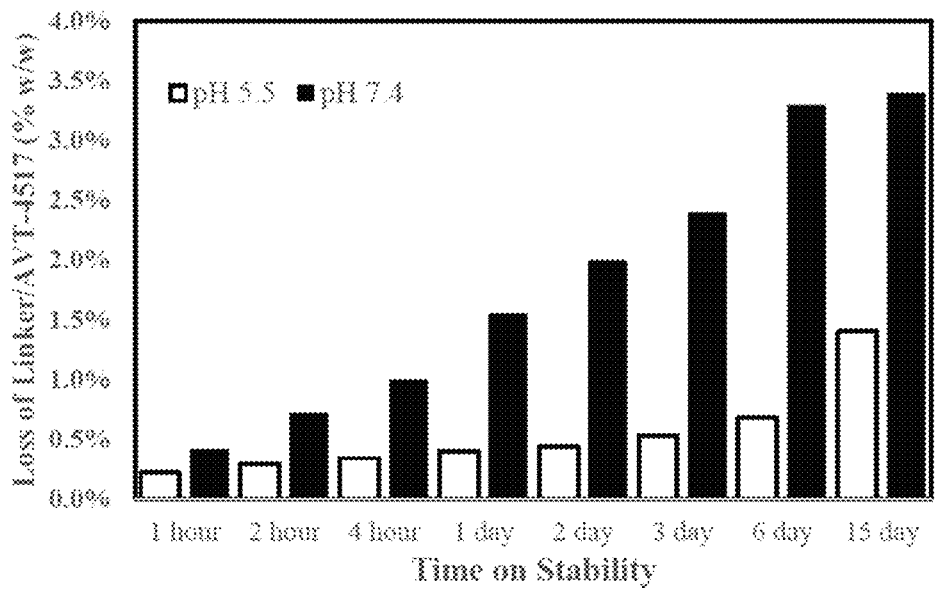
FIG. 7 is a line graph showing in vitro release profile (loss of linker with AVT-4517% w/w) of D-didesethyl sunitinib conjugate (D-4517) pH 7.4 and pH 5.5 over a period of 15 days with esterases at 37° C. mimicking plasma and intracellular conditions respectively.

In Vitro Drug Release Study:

In vitro drug release study was carried out at pH 7.4 and pH 5.5 with esterases at 37° C. mimicking plasma and intracellular conditions respectively. The release study was carried out in duplicates. The results are presented in FIG. 7. At intracellular conditions, less than 2 wt % drug arm is being released in 15 days. At plasma conditions, ~2% is being released in 24 h and around ~4% in 15 days. The ester bond between the dendrimer and the linker resulted in a loss of the linker with AVT-4517 over time in D-4517. At both conditions, the conjugate demonstrated good stability.

Example 6: In Vivo Pharmacokinetics of Dendrimer-Didesethyl Sunitinib Conjugate (D-4517)

Figure 8:
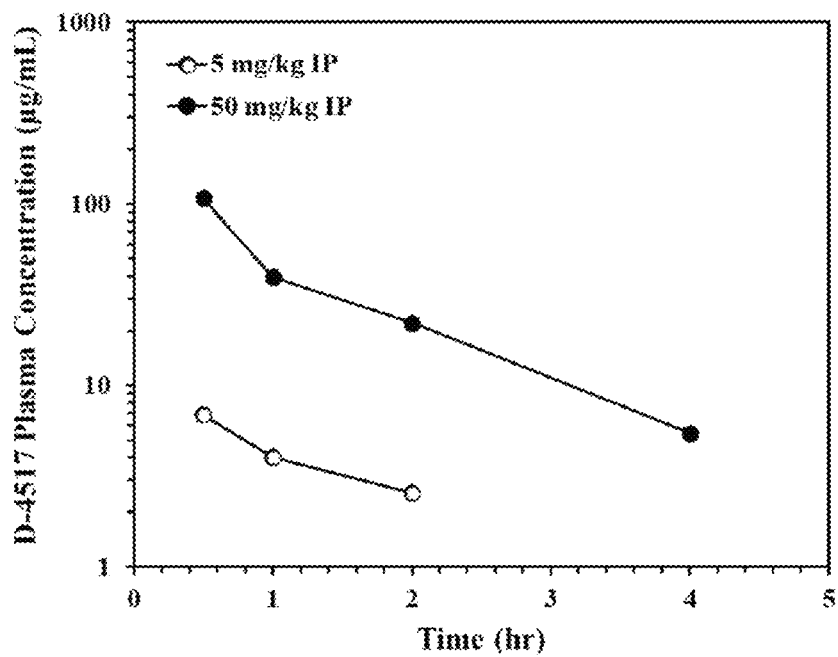
FIG. 8 is a line graph showing plasma concentration in μg/mL over time in Female C57/Bl6 mice injected IP with 5 or 50 mg/kg D-4517.

D-4517 Pharmacokinetics were evaluated in vivo in mice. Female C57/Bl6 mice were injected I.P. with 5 or 50 mg/kg D-4517 and blood samples were collected for determination of plasma D-4517 concentrations. Peak plasma concentrations were observed at the first time point sampled, 0.5 h. Exposure based on Cmax and AUC was dose related and approximately dose proportional. The terminal elimination, $T_{1/2}$, was about 1 hour following both dose levels. PK parameters estimated by noncompartmental methods are shown in Table 5 below and mean plasma concentrations versus time are shown in FIG. 8.

TABLE 5

Plasma D-4517 Concentrations Following IP Injection in Mice.

| Dose mg/kg | Cmax (µg/mL) | Tmax (h) | AUC0-t (h*µg/mL) | AUCINF (h*µg/mL) | CL/F (mL/h/kg) | Vz/F (mL/kg) | T½ (h) |
|---|---|---|---|---|---|---|---|
| 5.0 | 6.86 | 0.50 | 7.70 | 11.7 | 426 | 675 | 1.10 |
| 5.0 | 108 | 0.50 | 122 | 130 | 384 | 578 | 1.04 |

Toxicokinetic data was collected in rats. Sprague-Dawley rats received daily I.P. injections of 12 mg/kg or a single dose of 168 mg/kg D-4517 or a daily oral dose of 30 mg/kg sunitinib (40.21 mg/kg of sunitinib malate). Blood samples were collected, and plasma drug concentrations were determined. Noncompartmental toxicokinetic parameters were estimated.

Figure 9A:
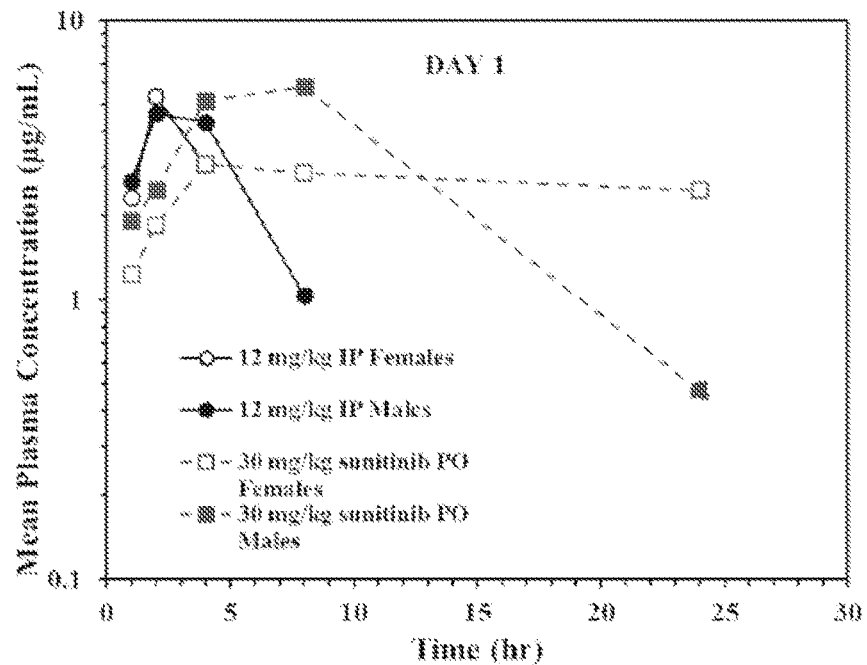
FIGS. 9A and 9B are line graphs showing plasma concentration in μg/mL over time (0-24 hours) for male and female groups of Sprague-Dawley rats that received daily IP injections of 12 mg/kg D-4517 and daily oral dose of 30 mg/kg sunitinib (40.21 mg/kg of sunitinib malate) on Day 1 (FIG. 9A), and Day 14 (FIG. 9B), respectively.
Figure 9B:
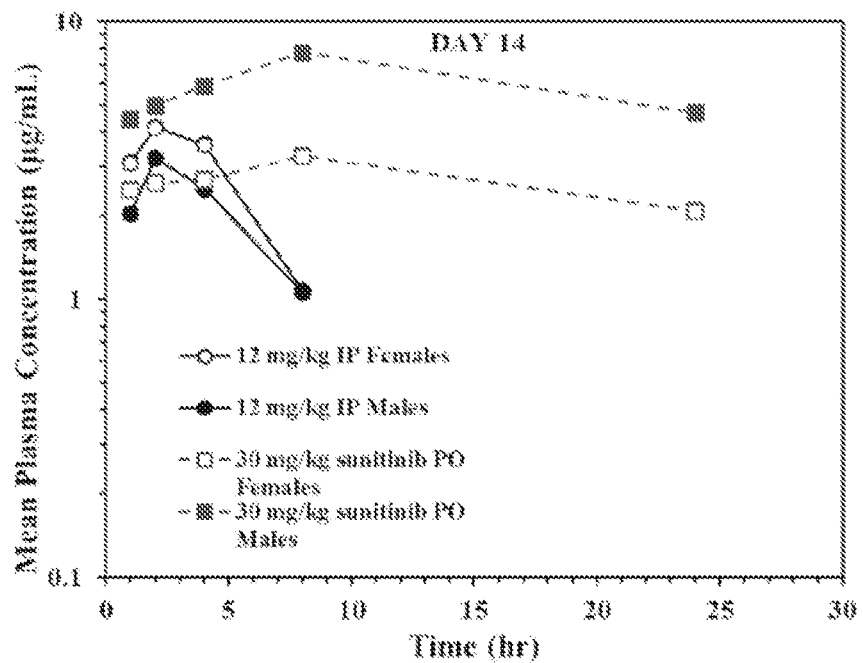

FIGS. 9A and 9B show plasma concentration versus time profiles on Day 1 and Day 14 for the 12 mg/kg D-4517 and sunitinib groups. There did not appear to be an obvious gender difference in D-4517 plasma concentrations, but for sunitinib, males had higher concentrations than females except at the 24 h time point on day 1. D-4517 plasma concentrations showed a faster decline than sunitinib. Terminal half-lives could not be reliably estimated because there were not enough time points in the terminal phase. Sunitinib was measurable 24 hours after dosing but D-4517 was not measurable beyond 8 hours post-dosing. Consequently, AUC estimates were higher for sunitinib compared to D-4517. Following a single dose of 168 mg/kg D4517, plasma concentrations were high at 1 h post dosing but at the next time point sampled, 24 h, only one animals had a measurable concentration.

The pharmacokinetic results indicate that the dose of D-4517 resulted in comparable maximum concentrations with lower total exposure compared to sunitinib. Separate rats received sunitinib malate orally for 14 days at a dose of 40.21 mg/kg. D-4517 was associated with no mortality nor effects upon clinical observations, body weights, food consumption or clinical pathology parameters (hematology, clinical chemistry and urinalysis). D-4517-related gross necropsy findings were limited to yellow discoloration of adipose tissue and mesentery in males and females at 12 mg/kg and/or 168 mg/kg, which correlated with subacute/chronic inflammation associated with intraperitoneal administration of test article. Organ weight changes included statistically significant decreases in spleen weights in males at 168 mg/kg though this observation had no microscopic correlate. Non-adverse microscopic findings included of minimal focal pigment in the choroid of the eyes and subacute/chronic inflammation in the abdominal fat/mesentery in males and females at 12 mg/kg and 168 mg/kg. Inflammation was likely secondary to intraperitoneal injection of test article and was observed secondarily along the serosal surfaces of the stomach, liver, and spleen.

Overall, D-4571 was well tolerated following single or repeated IP dosing. These observations were in contrast to sunitinib malate which was associated with various clinical and pathological changes in addition to mortality in female rats.

Example 7: Single Subcutaneous Dosing Study of Dendrimer-Didesethyl Sunitinib Conjugate (D-4517)

Figure 10:
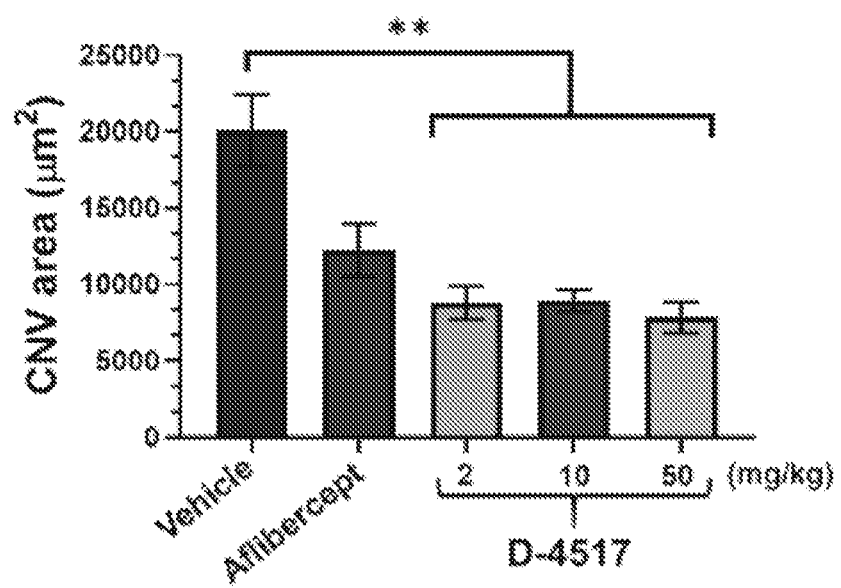
FIG. 10 is a bar graph showing mean area of choroidal neovascularization (CNV) ($\mu m^2$) in the eyes of mice treated with vehicle, aflibercept (40 μg), and three dose levels of D-didesethyl sunitinib conjugate (D-4517) at 2, 10 and 50 mg/kg in a single subcutaneous dose administered 24 hr after laser-induced rupture of Bruch's membrane in the eyes of C57BL/6 mice at day 14 post-treatment.

To evaluate the preferred route of dosing in humans, a single subcutaneous dosing study of D-4517 was conducted in the laser-induced CNV mouse model. Control mice (n=8/group) were injected intravitreally with either vehicle or aflibercept (40 µg) one day after laser treatment. Three dose levels of D-4517 (2, 10 and 50 mg/kg; n=8/group) was administered as a single subcutaneous dose one day after laser treatment. After 14 days, mice were sacrificed and flat mounts of the sclera-choroid/RPE complexes were stained with DAPI and isolectin IB4. CNV area was measured with fluorescent microscopy and imaging software. As shown in FIG. 10, all three doses of D-4517 given as a single subcutaneous dose reduced CNV lesion area significantly. The responses in the D-4517 treated animals were more consistent than those observed in the aflibercept treated animals. This study demonstrates significant efficacy observed from subcutaneously administered D-4517 in CNV models.

Example 8: Conjugation of Didesethyl Sunitinib Via a Non-Cleavable Ether Linkage on Dendrimer Methods
Synthesis of Dendrimer Conjugate via a Non-Cleavable Ether Linkage on Dendrimer The synthesis began by the construction of a bifunctional dendrimer. At dendrimer generation 3.5, 7 alkyne functional groups were introduced using a polyethyl glycol (PEG) linker with an amine at one end and a hexyne at the other end to produce a generation 4 bifunctional dendrimer (compound 1 in FIG. 11) with 7 alkyne arms and 57 hydroxyl groups on the surface. The structure of the dendrimer was confirmed by 1H NMR spectroscopy.

Figure 11:
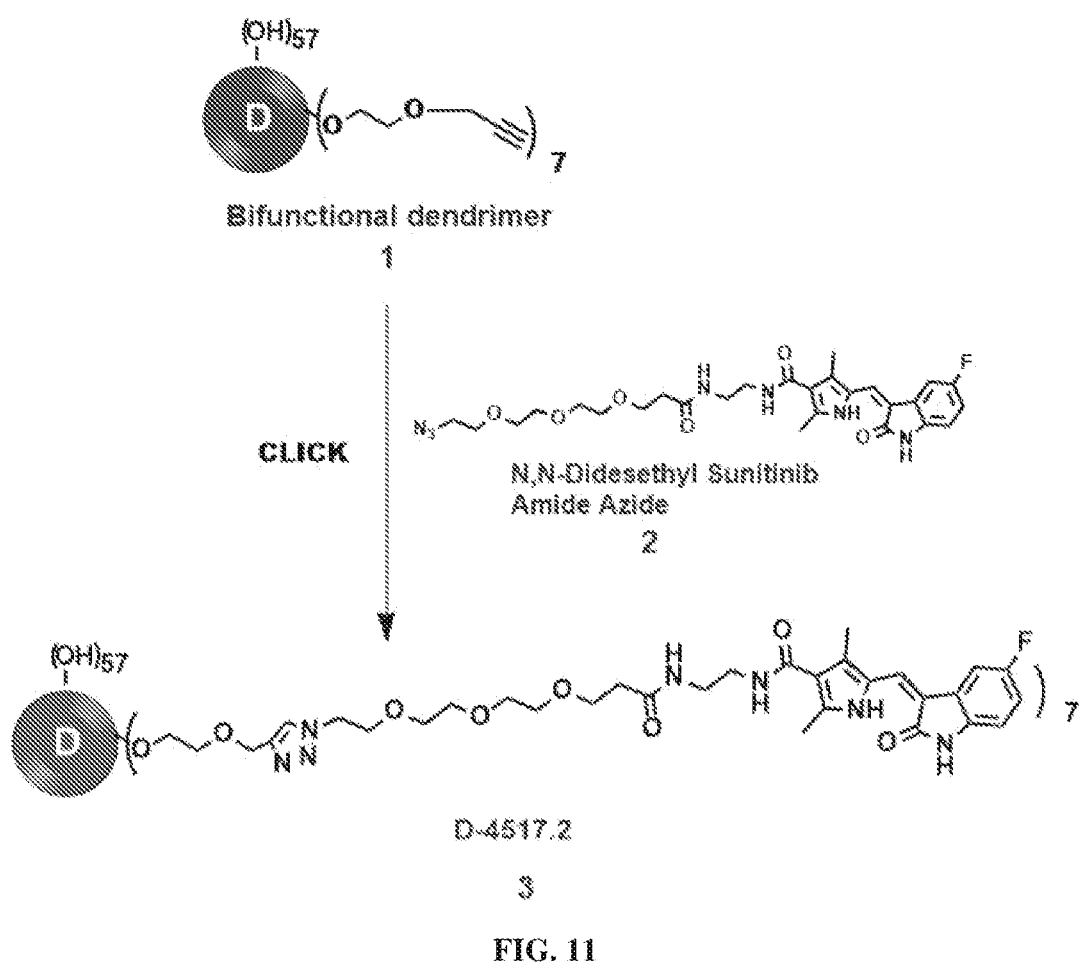
FIG. 11 is a scheme showing the synthesis of an exemplary dendrimer-conjugate (D-4517.2) in which N,N-didesethyl sunitinib is conjugated to a dendrimer with ether linkages for enhanced in vivo stability.

The clickable didesethyl sunitinib analog (compound 2 in FIG. 11, a.k.a. AVT-4517), including of didesethyl sunitinib, a three ethylene glycol (PEG3) spacer and a terminal azide, was synthesized to participate in the click reaction with alkyne groups on the surface of the dendrimer. The active agent, compound 2, is manufactured using a 5-step synthesis shown in FIG. 5.

Figure 12:
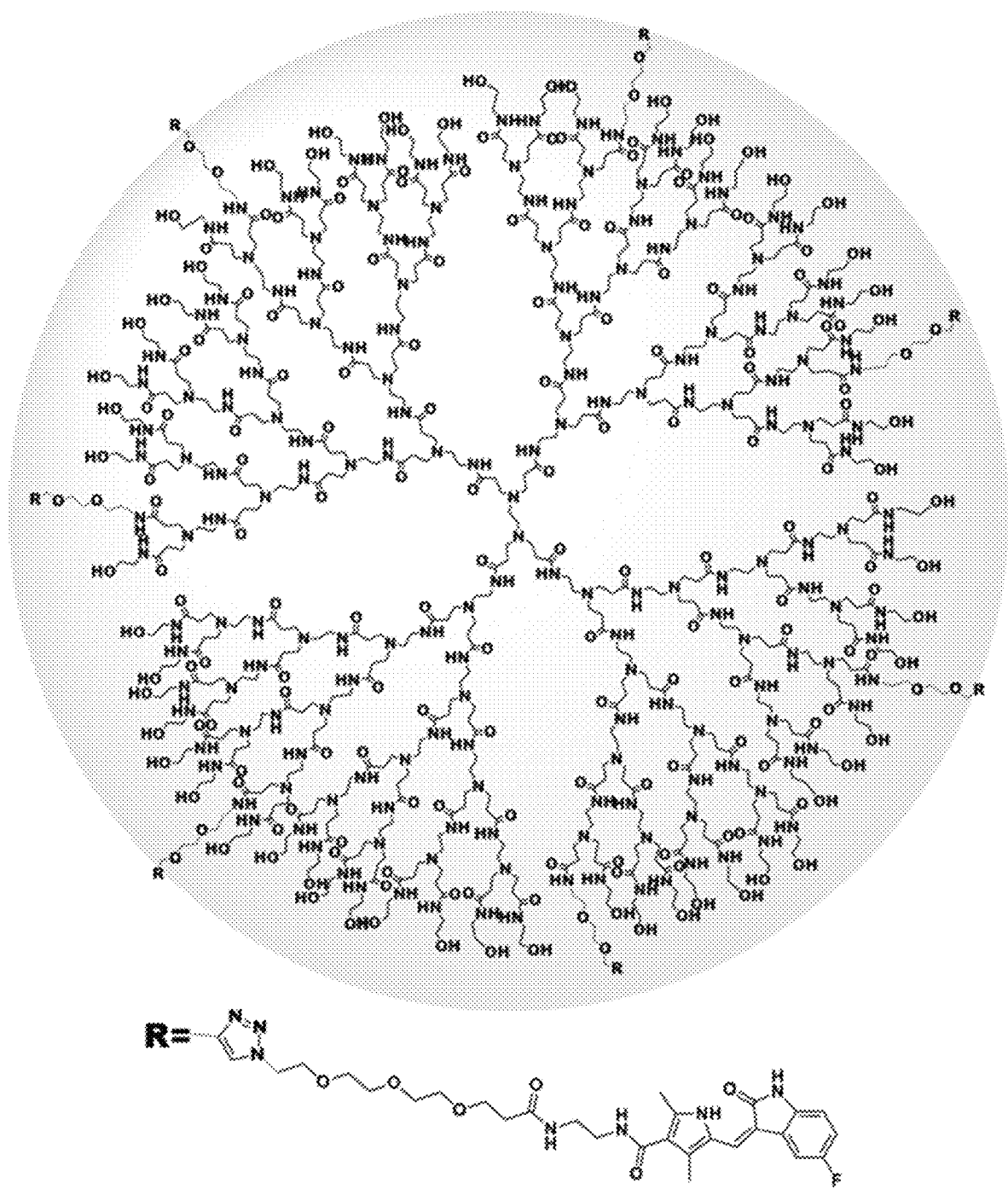
FIG. 12 is a schematic showing the chemical structure of compound D-4517.2.

AVT-4517 (compound 2 in FIG. 11) is finally reacted with the bifunctional dendrimer (compound 1 in FIG. 11) with hexyne groups by copper (I) catalyzed alkyne-azide click chemistry to yield D-4517.2 (compound 3 in FIG. 11) with the full structure shown in FIG. 12. After conjugation of the analog to the dendrimer, the D-4517.2 is purified by tangential flow filtration (TFF) to remove any impurities and enable purification into the final formulation.

$^1$H-NMR Analysis of D-4517.2 Conjugates

The formation of product D-4517.2 is confirmed by 1H NMR. The 1H NMR spectrum of the conjugate clearly shows the peaks corresponding to the dendrimer, drug and linkers attached to it, and the drug loading was calculated by comparing these peaks with the help of proton integration method. The internal amide protons from the dendrimer are present in between $\delta$ 8.5-7.5 ppm when spectrum is recorded in deuterated DMSO. These amide peaks are a reference standard for the rest of the peaks. The —NH peaks from drug appear at $\delta$ 13.6 and 10.8 ppm. There are 4 protons from the drug and one triazole proton which is formed after the click reaction merged with internal amide peaks and comes in between $\delta$ 8.5-7.5 ppm. Additionally, 2 aromatic protons from sunitinib situated next to the fluorine group appear at $\delta$ 6.95-6.85 ppm. A sharp triazole peak at $\delta$ 7.7 ppm which is a signature peak for the click transformation is observed when the NMR solvent is switched from deuterated DMSO to CD$_3$OD. After the click, the CH$_2$ present next to the azide down shielded and can be observed at $\delta$ 4.4 ppm. NMR is also used to quantitate the number of drug molecules conjugated to the hydroxyl dendrimer. The drug loading was calculated by proton integration method by comparing the protons of dendrimer internal amide protons to drug protons.

HPLC Analysis for Assessment of Purity of D-4517.2

The purity of the dendrimer drug conjugate, intermediate and drug linker was evaluated using HPLC. The final conjugate is >99% pure by HPLC. The dendrimer G4-OH and dendrimer hexyne intermediate is visible at 210 nm channel and the didesethyl sunitinib is visible at 430 nm in HPLC. The retention time of the compound 2 is around 16.9 minutes but once the hydrophobic drug molecules are attached to the dendrimer, the peak of the final conjugate shifts towards the right and comes around 27 minutes, which confirms the attachment of hydrophobic drugs to the dendrimer construct. Once the drug is attached to dendrimer the peak corresponding to it can be observed at both 210 nm (dendrimer absorption wavelength) and 430 nm (drug absorption wavelength) channels, which further confirms the formation of product. The drug loading of the dendrimer conjugate is around 12.6% wt/wt which corresponds to 7 molecules of drug attached per dendrimer molecule.

Size and Zeta Potential

The size and the zeta potential distribution of the D-4517.2 are determined using a Zetasizer Nano ZS instrument. For the size measurement, the sample was prepared by dissolving the dendrimer in deionized water (18.2Ω) to make a solution with a final concentration of 0.5 mg/mL. The solution was then filtered through 0.2 μm syringe filters (Pall Corporation, 0.2 μm HT Tuffryn membrane) directly into the cell (UV transparent disposable cuvette, Dimensions: 12.5×12.5×45 mm). For zeta potential measurement, the sample was prepared at a concentration of 0.2 mg/mL in 10 mM NaCl using above mentioned procedure. Malvern Zetasizer Nanoseries disposable folded capillary cell was used for the measurements. The size of D-4517 was 5.5±0.5 nm and zeta potential was slightly positive (+5.4±0.4 mV).

Size Exclusion Chromatography Multiple-Angle Laser Scattering (SEC-MALS)

The molar mass of D-4517.2 will be determined by size exclusion chromatography multipleangle laser scattering (SEC-MALS).

Results

D-4517 has nanomolar affinity for VEGFR2 and does not require the release of the active drug, AVT-4517. To further increase the stability of the conjugate under physiological conditions and further reduce the release of the drug from the conjugate as observed in D-4517 buffer and plasma stability studies, the cleavable ester linkages on the dendrimer surface were replaced with non-cleavable linkages as demonstrated in the structure of D-4517.2 (FIG. 12). There are no cleavable bonds in the structure of D-4517.2.

D-4517.2 is a covalent conjugate of generation-4, hydroxyl-terminated PAMAM dendrimers, containing an ethylene diamine (EDA) core, amidoamine repeating units [$CH_2CH_2CONHCH_2CH_2N$]), and 64 hydroxyl end groups (chemical formula: $C_{622}H_{1184}N_{186}O_{188}$) with didesethyl sunitinib analog (AVT-4517) conjugated to the dendrimer by a highly efficient click chemistry approach. The hydroxyl, generation-4, PAMAM dendrimers are mono-disperse and produced with high compositional purity (>95%). For the preparation of D-4517.2, seven of the 64 hydroxyl groups on the dendrimer are modified to attach AVT-4517 (~12.6% of total mass).

Stability Studies in Human, Mouse and Rat Plasma

Figure 13:
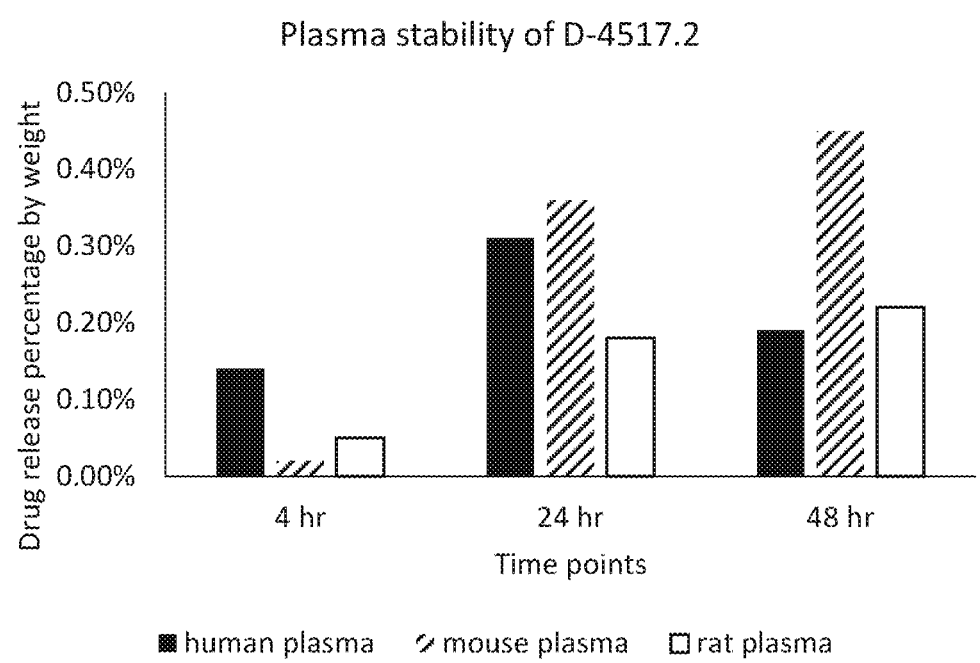
FIG. 13 is a bar graph showing drug release percentage by weight (0.0%-0.50%) of D-didesethyl sunitinib conjugate, D-4517.2, in human, mouse, and rat plasma conditions over time points for each of 4, 24 and 48 hours, respectively.

In vitro stability of dendrimer didesethyl sunitinib conjugates, D-4517 and D-4517.2, in human, mouse and rat plasma was evaluated at physiological conditions. The results presented in FIG. 13. Compared with D4517 (2% (weight percentage) release in human plasma, and 4% (weight percentage) release in rat plasma), the plasma stability of D4517.2 is improved significantly. At 48 hrs, in all three plasma, less than 0.5% drug (by weight) was released from dendrimer drug conjugates.

Binding Affinity

The kinase comparative binding affinity of D-4517 and D-4517.2 was evaluated, and the results are presented in Table 6.

TABLE 6

Dendrimer didesethyl sunitinib conjugates, D-4517 and D-4517.2 binding assay study

| Compound Name | Gene Symbol | Modifier | Kd (nM) |
| --- | --- | --- | --- |
| D4517 | VEGFR2 | = | 27 |
| D4517 | VEGFR1 | = | 1100 |
| D4517 | CSF1R | = | 82 |
| D4517 | KIT | = | 3.4 |
| D4517 | PDGFRA | = | 16 |
| D4517 | PDGFRB | = | 11 |
| D-4517.2 | CSF1R | = | 41 |
| D-4517.2 | VEGFR1 | = | 890 |
| D-4517.2 | KIT | = | 3 |
| D-4517.2 | PDGFRA | = | 11 |
| D-4517.2 | PDGFRB | = | 7.5 |
| D-4517.2 | VEGFR2 | = | 14 |

The IC50 results of D-4517.2 is lower than D-4517 on all tested assay, which indicates the stronger binding between D4517.2 and tyrosine kinase receptor.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating a disease or disorder of the eye in a subject in need thereof, the method comprising:
   administering to the subject an effective amount of a composition comprising a dendrimer conjugated to one or more receptor tyrosine kinase inhibitors,
   wherein the dendrimer comprises a plurality of terminal hydroxyl groups and at least one terminal group forming an ether bond between the dendrimer and a receptor tyrosine kinase inhibitor conjugated thereto.

2. The method of claim 1, wherein the receptor tyrosine kinase inhibitor is a vascular endothelial growth factor receptor (VEGFR) inhibitor.

3. The method of claim 2, wherein the VEGFR inhibitor is selected from the group consisting of sunitinib, dasatinib, sorafenib, pazopanib, vandetanib, axitinib, cediranib, vatalanib, nintedanib, motesanib, and analogues thereof.

4. The method of claim 3, wherein the VEGFR inhibitor is sunitinib or N,N-didesethyl sunitinib.

5. The method of claim 1, wherein the dendrimer is conjugated to the receptor tyrosine kinase inhibitor through a linker attached to the at least one terminal group.

6. The method of claim 5, wherein the linker comprises polyethylene glycol.

7. The method of claim 5, wherein an amide bond is formed between the linker and the receptor tyrosine kinase inhibitor.

8. The method of claim 7, wherein the linker-receptor tyrosine kinase inhibitor comprises a structure of the following formula:

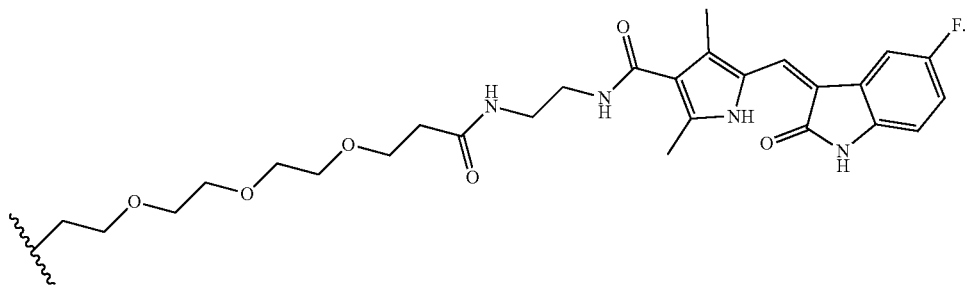 [SMILES: *CCOCCOCCOCCC(=O)NCCNC(=O)c1c(C)[nH]c(/C=C2\C(=O)Nc3ccc(F)cc32)c1C]

9. The method of claim 1, wherein the one or more receptor tyrosine kinase inhibitors are at a concentration of between about 5% and about 20% by weight of the conjugated dendrimer.

10. The method of claim 1, wherein the one or more receptor tyrosine kinase inhibitors are conjugated to less than 20% of all terminal groups on the dendrimer.

11. The method of claim 1, wherein the dendrimer is a generation 4, generation 5, or generation 6 poly(amidoamine) dendrimer.

12. The method of claim 1, wherein the composition is administered to the subject systemically.

13. The method of claim 1, wherein the composition is administered to the subject intravenously, subcutaneously, or orally.

14. The method of claim 1, wherein the disease or disorder of the eye is an inflammatory or angiogenic disease of the eye.

15. The method of claim 1, wherein the disease or disorder of the eye is selected from the group consisting of age-related macular degeneration (AMD), retinitis pigmentosa, optic neuritis, uveitis, retinal detachment, temporal arteritis, retinal ischemia, arteriosclerotic retinopathy, hypertensive retinopathy, retinal artery blockage, retinal vein blockage, diabetic retinopathy, macular edema, retinal neovascularization, and choroidal neovascularization.

16. The method of claim 15, wherein the disease or disorder of the eye is wet AMD.

17. The method of claim 1, wherein the disease or disorder of the eye is associated with activated microglia, activated macrophages, and/or retinal pigment epithelial (RPE) cells in the eye.

18. The method of claim 17, wherein the composition is in an amount effective to target activated microglia, activated macrophages, and/or RPE cells in the eye.

19. The method of claim 17, wherein the composition is in an amount effective to reduce the number and/or activity of activated microglia and/or activated macrophages in the eye.

20. The method of claim 15, wherein the disease or disorder of the eye is diabetic macular edema.

* * * * *